US009295697B2

(12) United States Patent
Yu

(10) Patent No.: US 9,295,697 B2
(45) Date of Patent: Mar. 29, 2016

(54) EPISOMAL REPROGRAMMING WITH CHEMICALS

(75) Inventor: Junying Yu, Middleton, WI (US)

(73) Assignee: Cellular Dynamics International, Inc., Madison, WI (US)

( * ) Notice: Subject to any disclaimer, the term of this patent is extended or adjusted under 35 U.S.C. 154(b) by 1163 days.

(21) Appl. No.: 12/939,454

(22) Filed: Nov. 4, 2010

(65) Prior Publication Data

US 2011/0104125 A1     May 5, 2011

Related U.S. Application Data

(60) Provisional application No. 61/258,120, filed on Nov. 4, 2009.

(51) Int. Cl.
| | |
|---|---|
| *C12N 5/10* | (2006.01) |
| *C12N 5/071* | (2010.01) |
| *A61K 35/545* | (2015.01) |
| *A61P 25/00* | (2006.01) |

(52) U.S. Cl.
CPC ......... *A61K 35/545* (2013.01); *C12N 2501/115* (2013.01); *C12N 2501/15* (2013.01); *C12N 2501/235* (2013.01); *C12N 2501/60* (2013.01); *C12N 2501/70* (2013.01); *C12N 2510/00* (2013.01)

(58) Field of Classification Search
USPC ................................. 435/377, 366; 424/93.7
See application file for complete search history.

(56) References Cited

U.S. PATENT DOCUMENTS

| | | | |
|---|---|---|---|
| 8,298,825 B1 | 10/2012 | Hochedlinger et al. | |
| 8,546,140 B2 * | 10/2013 | Mack et al. .................... | 435/377 |
| 2005/0260564 A1 * | 11/2005 | Sugden et al. ................... | 435/5 |
| 2008/0014638 A1 | 1/2008 | Smith et al. | |
| 2008/0171385 A1 * | 7/2008 | Bergendahl et al. .......... | 435/366 |
| 2008/0233610 A1 | 9/2008 | Thomson et al. ............... | 435/29 |
| 2009/0203545 A1 * | 8/2009 | Lindner et al. .................. | 506/14 |
| 2010/0041137 A1 | 2/2010 | Smith et al. | |
| 2010/0310525 A1 | 12/2010 | Chevalier et al. | |
| 2011/0110899 A1 * | 5/2011 | Shi et al. ....................... | 424/93.7 |
| 2012/0129172 A1 | 5/2012 | Okano et al. | |
| 2012/0196360 A1 | 8/2012 | Okita et al. | |
| 2012/0264218 A1 * | 10/2012 | Lin et al. ....................... | 435/455 |

FOREIGN PATENT DOCUMENTS

| | | |
|---|---|---|
| WO | WO 2009/006422 | 1/2009 |
| WO | WO 2009/007852 | 1/2009 |
| WO | WO 2009/101407 | 8/2009 |
| WO | WO 2009/117439 | 9/2009 |
| WO | WO 2010/077955 | 7/2010 |
| WO | WO 2010/124143 | 10/2010 |

OTHER PUBLICATIONS

Lannon et al. (A defined, feeder-independent medium for human embryonic stem cell culture, 2008, Cell Research, vol. 18. s34, 1 page).*
Ren et al. (Establishment and applications of Epstein-Barr Virus-based episomal vectors in human embryonic stem cells, 2006, Stem Cells, vol. 24, pp. 1338-1347).*
Claassen et al., "ROCK inhibition enhances the recovery and growth of cryopreserved human embryonic stem cells and human induced pluripotent stem cells," *Molecular Reproduction and Development*, 76(8):722-732, 2009.
Extended European Search Report issued in European Patent Application No. 10829086.7, dated May 14, 2013.
Feng et al., "Molecules that promote or enhance reprogramming of somatic cells to induced pluripotent stem cells," *Cell Stem Cell*, 4(4):301-312, 2009.
Vallier et al., "Signaling pathways controlling pluripotency and early cell fate decisions of human induced pluripotent stem cells," *Stem Cells*, 27(11):2655-2666, 2009.
Yamanaka, "Elite and stochastic models for induced pluripotent stem cell generation," *Nature*, 460(7251):49-52, 2009.
Buehr et al., "Capture of authentic embryonic stem cells from rat blastocysts," *Cell*, 135:1287-98, 2008.
Chen and Lin, "Current progress and prospects of induced pluripotent stem cells," *Science in China Series C: Life Sciences*, 52(7):622-636, 2009.
Chen et al., "Actin-myosin contractility is responsible for the reduced viability of dissociated human embryonic stem cells," *Cell Stem Cell*, 7:240-248, 2010.
Huangfu et al., "Induction of pluripotent stem cells by defined factors is greatly improved by small-molecule compounds," *Nature Biotechnology*, 26(7):795-797, 2008.
Ichida et al., "A small-molecule inhibitor of Tgf-beta signaling replaces Sox2 in reprogramming by inducing *Nanog*," *Cell Stem Cell*, 5:491-503, 2009.
Lai et al., "ROCK inhibition facilitates the generation of human-induced pluripotent stem cells in a defined, fedder-, and serum-free system," *Cellular Reprogramming*, 12(6):641-653, 2010.
Leight and Sugden, "Establishment of an oriP replicon is dependent upon an infrequent, epigenetic event," *Mol. Cell. Bio.*, 21:4149-61, 2001.
Li et al., "Generation of iPSCs from mouse fibroblasts with a single gene, Oct. 4, and small molecules," *Cell Research*, 21:196-204, 2011. Published online Oct. 19, 2010.
Li et al., "Generation of rat and human induced poluripotent stem cells by combining genetic reprogramming and chemical inhibitors," *Cell Stem Cell*, 4:16-19:2009.

(Continued)

*Primary Examiner* — Sharmila G. Landau
*Assistant Examiner* — Shannon Janssen
(74) *Attorney, Agent, or Firm* — Parker Highlander PLLC

(57) ABSTRACT

Methods and composition of induction of pluripotent stem cells are disclosed. For example, in certain aspects methods for generating essentially vector-free induced pluripotent stem cells with cell signaling regulators are described. Furthermore, certain aspects of the invention provide novel compositions comprising induced pluripotent stem cells essentially free of exogenous retroviral vector elements in the presence of a medium comprising signaling inhibitors. In certain aspects, feeder-free episomal reprogramming methods may be provided.

28 Claims, 14 Drawing Sheets

(56) References Cited

OTHER PUBLICATIONS

Li et al., "Germline competent embryonic stem cells derived from rat blastocysts," *Cell*, 135:1299-310, 2008.

Lin et al., "A chemical platform for improved induction of human iPSCs," *Nature Methods*, 6(11):805-808, 2009.

Lindner and Sugden, "The plasmid replicon of Epstein-Barr virus: mechanistic insights into efficient, licensed, extrachromosomal replication in human cells," *Plasmid*, 58:1-12, 2007.

Lyssiotis et al., "Reprogramming of murine fibroblasts to induced pluripotent stem cells with chemical complementation of KIF4," *PNAS*, 106:22:8912-9817, 2009.

Maherali and Hochedlinger, "Tgf-beta signal inhibition cooperates in the induction of iPSCs and replaces Sox2 and cMyc," *Current Biology*, 19:1718-1723, 2009.

Nanbo et al., "The coupling of synthesis and partitioning of EBV's plasmid replicon is revealed in live cells," *EMBO. J...*, 19:4252-62, 2007.

Richards et al., "The transcriptome profile of human embryonic stem cells as defined by SAGE," *Stem Cells*, 22:51-64, 2004.

Scheper and Copray, "The molecular mechanism of induced pluripotency: A two stage switch," *Stem Cell Rev. And Resp.*, 5:204-223, 2009.

Shi et al., "A combined chemical and genetic approach for the generation of induced pluripotent stem cells," *Cell Stem Cell*, 2:525-528, 2008.

Silva et al., "Promotion of reprogramming to ground state pluripotency by signal inhibition," *PLoS Biol.*, 6:e253, pp. 2237-2247, 2008.

Wantabe et al., "A ROCK inhibitor permits survival of dissociated human embryonic stem cells," *Nat. Biotechnol.*, 25:681-686, 2007.

Ying et al., "The ground state of embryonic stem cell self-renewal," *Nature*, 453:519-23, 2008.

Yu et al., "Human induced pluripotent stem cells free of vector and transgene sequences," *Science*, 324:797-801, 2009.

Yu et al., Supporting online material for "Human induced pluripotent stem cells free of vector and transgene sequences," *Science Express*, available online at: http://www.sciencemag.org/cgi/content/full/1172482/DC1, 17 pages, published Mar. 26, 2009.

Zhu et al., "Reprogramming of human primary somatic cells by Oct. 4 and chemical compounds," *Cell Stem Cell.*, 7:651-655, 2010.

Office Communication issued in Chinese Patent Application No. 201080049958.X, dated Feb. 16, 2013. (English translation of Chinese text).

Tolonchi el al "Feeder-and serum-free establishment and expansion of human induced pluripotent stein cells," *Int. J. Dcv. Biol.*, 54(5):877-886, 2010.

PCT International Search Report and Written Opinion issued in International application No. PCT/US2010/05544, dated Jul. 13, 2011.

Takahashi et al., "Induction of pluripotent stem cells from adult human fibroblasts by defined factors," *Cell*, 131:1-12, 2007.

Fusaki et al., "Efficient induction of transgene-free human pluripotent stem cells using a vector based on Sendai virus, an RNA virus that does not integrate into the host genome," *Proc. Jpn. Acad. Ser. B*, 85(8):348-362, 2009.

Nakagawa et al., "Promotion of direct reprogramming by transformation-deficient Myc," *PNAS*, 107(32):14152-14157, 2010.

Office Action issued in Japanese Application No. 2012-537223, mailed Dec. 15, 2014, and English language translation thereof.

\* cited by examiner

SEQUENCE LISTING

```
<160> NUMBER OF SEQ ID NOS: 58

<210> SEQ ID NO 1
<211> LENGTH: 19
<212> TYPE: DNA
<213> ORGANISM: Artificial Sequence
<220> FEATURE:
<223> OTHER INFORMATION: Synthetic primer

<400> SEQUENCE: 1
cagtgcccga aacccacac                                                   19

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
ggagacccag cagcctcaaa                                                  20

<210> SEQ ID NO 3
<211> LENGTH: 20
<212> TYPE: DNA
<213> ORGANISM: Artificial Sequence
```

```
<220> FEATURE:
<223> OTHER INFORMATION: Synthetic primer

<400> SEQUENCE: 3
agtttgtgcc agggtttttg                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4 acttcaccttt ccctccaacc                                             20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
cagaaggcct cagcacctac                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
attgttccag gtctggttgc                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
tttggaagct gctggggaag                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
gatgggagga ggggagagga                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
agtctccaag cgacgaaaaa                                              20
```

```
<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
tttcacgttt gcaactgtcc                                                    20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
agtggcctgg atagggaagt                                                    20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
cttggctcca tgaatctggt                                                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
gtggacctga cctgccgtct                                                    20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
ggaggagtgg gtgtcgctgt                                                    20

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
agtgagaggc aacctggaga                                                    20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 16
aggaactgct tccttcacga                                          20

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
cagaaggcct cagcacctac                                          20

<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
aggaactgct tccttcacga                                          20

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
cccacacagg tgagaaacct                                          20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
aggaactgct tccttcacga                                          20

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
tggctctcct caagcgtatt                                          20

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
gtggagaaag atgggagcag                                          20

<210> SEQ ID NO 23
```

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
tggggagaag aacatggaag                                           20

<210> SEQ ID NO 24
<211> LENGTH: 20
<212> TYPE: DNA
<213> ORGANISM: Artificial Sequence
<220> FEATURE:
<223> OTHER INFORMATION: Synthetic primer

<400> SEQUENCE: 24
aggaactgct tccttcacga                                           20

<210> SEQ ID NO 25
<211> LENGTH: 20
<212> TYPE: DNA
<213> ORGANISM: Artificial Sequence
<220> FEATURE:
<223> OTHER INFORMATION: Synthetic primer

<400> SEQUENCE: 25
tggctctcct caagcgtatt                                           20

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
gcttagcctc gtcgatgaac                                           20

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
tggctctcct caagcgtatt                                           20

<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
gcaaactgct ggttggacac                                           20

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
```

```
tggctctcct caagcgtatt                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic primer

<400> SEQUENCE: 30
caccgagtcg tagtcgaggt                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic primer

<400> SEQUENCE: 31
agtttgtgcc agggttttg                                               20

<210> SEQ ID NO 32
<211> LENGTH: 20
<212> TYPE: DNA
<213> ORGANISM: Artificial Sequence
<220> FEATURE:
<223> OTHER INFORMATION: Synthetic primer

<400> SEQUENCE: 32
acttcacctt ccctccaacc                                              20

<210> SEQ ID NO 33
<211> LENGTH: 20
<212> TYPE: DNA
<213> ORGANISM: Artificial Sequence
<220> FEATURE:
<223> OTHER INFORMATION: Synthetic primer

<400> SEQUENCE: 33
gtggacctga cctgccgtct                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic primer

<400> SEQUENCE: 34
ggaggagtgg gtgtcgctgt                                              20

<210> SEQ ID NO 35
<211> LENGTH: 20
<212> TYPE: DNA
<213> ORGANISM: Artificial Sequence
<220> FEATURE:
<223> OTHER INFORMATION: Synthetic primer

<400> SEQUENCE: 35
agtgagaggc aacctggaga                                              20

<210> SEQ ID NO 36
<211> LENGTH: 20
<212> TYPE: DNA
```

```
<213> ORGANISM: Artificial Sequence
<220> FEATURE:
<223> OTHER INFORMATION: Synthetic primer

<400> SEQUENCE: 36
aggaactgct tccttcacga                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic primer

<400> SEQUENCE: 37
cagaaggcct cagcacctac                                              20

<210> SEQ ID NO 38
<211> LENGTH: 20
<212> TYPE: DNA
<213> ORGANISM: Artificial Sequence
<220> FEATURE:
<223> OTHER INFORMATION: Synthetic primer

<400> SEQUENCE: 38
aggaactgct tccttcacga                                              20

<210> SEQ ID NO 39
<211> LENGTH: 20
<212> TYPE: DNA
<213> ORGANISM: Artificial Sequence
<220> FEATURE:
<223> OTHER INFORMATION: Synthetic primer

<400> SEQUENCE: 39
cccacacagg tgagaaacct                                              20

<210> SEQ ID NO 40
<211> LENGTH: 20
<212> TYPE: DNA
<213> ORGANISM: Artificial Sequence
<220> FEATURE:
<223> OTHER INFORMATION: Synthetic primer

<400> SEQUENCE: 40
aggaactgct tccttcacga                                              20

<210> SEQ ID NO 41
<211> LENGTH: 20
<212> TYPE: DNA
<213> ORGANISM: Artificial Sequence
<220> FEATURE:
<223> OTHER INFORMATION: Synthetic primer

<400> SEQUENCE: 41
cccacacagg tgagaaacct                                              20

<210> SEQ ID NO 42
<211> LENGTH: 20
<212> TYPE: DNA
<213> ORGANISM: Artificial Sequence
<220> FEATURE:
<223> OTHER INFORMATION: Synthetic primer

<400> SEQUENCE: 42
cccactgaac ctgaaacata                                              20
```

```
<210> SEQ ID NO 43
<211> LENGTH: 20
<212> TYPE: DNA
<213> ORGANISM: Artificial Sequence
<220> FEATURE:
<223> OTHER INFORMATION: Synthetic primer

<400> SEQUENCE: 43
tggggagaag aacatggaag                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic primer

<400> SEQUENCE: 44
aggaactgct tccttcacga                                               20

<210> SEQ ID NO 45
<211> LENGTH: 20
<212> TYPE: DNA
<213> ORGANISM: Artificial Sequence
<220> FEATURE:
<223> OTHER INFORMATION: Synthetic primer

<400> SEQUENCE: 45
accagctcgc agacctacat                                               20

<210> SEQ ID NO 46
<211> LENGTH: 20
<212> TYPE: DNA
<213> ORGANISM: Artificial Sequence
<220> FEATURE:
<223> OTHER INFORMATION: Synthetic primer

<400> SEQUENCE: 46 cccccctgaac ctgaaacata                                              20

<210> SEQ ID NO 47
<211> LENGTH: 20
<212> TYPE: DNA
<213> ORGANISM: Artificial Sequence
<220> FEATURE:
<223> OTHER INFORMATION: Synthetic primer

<400> SEQUENCE: 47
aagcgcagat caaaaggaga                                               20

<210> SEQ ID NO 48
<211> LENGTH: 20
<212> TYPE: DNA
<213> ORGANISM: Artificial Sequence
<220> FEATURE:
<223> OTHER INFORMATION: Synthetic primer

<400> SEQUENCE: 48 cccccctgaac ctgaaacata                                              20

<210> SEQ ID NO 49
<211> LENGTH: 20
<212> TYPE: DNA
<213> ORGANISM: Artificial Sequence
<220> FEATURE:
```

<223> OTHER INFORMATION: Synthetic primer

<400> SEQUENCE: 49
tcaagaggcg aacacacaac                                          20

<210> SEQ ID NO 50
<211> LENGTH: 20
<212> TYPE: DNA
<213> ORGANISM: Artificial Sequence
<220> FEATURE:
<223> OTHER INFORMATION: Synthetic primer

<400> SEQUENCE: 50
caacagatgg ctggcaacta                                          20

<210> SEQ ID NO 51
<211> LENGTH: 20
<212> TYPE: DNA
<213> ORGANISM: Artificial Sequence
<220> FEATURE:
<223> OTHER INFORMATION: Synthetic primer

<400> SEQUENCE: 51
agtttgtgcc agggttttg                                           20

<210> SEQ ID NO 52
<211> LENGTH: 20
<212> TYPE: DNA
<213> ORGANISM: Artificial Sequence
<220> FEATURE:
<223> OTHER INFORMATION: Synthetic primer

<400> SEQUENCE: 52
acttcacctt ccctccaacc                                          20

<210> SEQ ID NO 53
<211> LENGTH: 25
<212> TYPE: DNA
<213> ORGANISM: Artificial Sequence
<220> FEATURE:
<223> OTHER INFORMATION: Synthetic primer

<400> SEQUENCE: 53
atttgttttt tgggtagtta aaggt                                    25

<210> SEQ ID NO 54
<211> LENGTH: 27
<212> TYPE: DNA
<213> ORGANISM: Artificial Sequence
<220> FEATURE:
<223> OTHER INFORMATION: Synthetic primer

<400> SEQUENCE: 54
ccaactatct tcatcttaat aacatcc                                  27

<210> SEQ ID NO 55
<211> LENGTH: 25
<212> TYPE: DNA
<213> ORGANISM: Artificial Sequence
<220> FEATURE:
<223> OTHER INFORMATION: Synthetic primer

<400> SEQUENCE: 55
ttaatttatt gggattatag gggtg                                    25

```
<210> SEQ ID NO 56
<211> LENGTH: 24
<212> TYPE: DNA
<213> ORGANISM: Artificial Sequence
<220> FEATURE:
<223> OTHER INFORMATION: Synthetic primer

<400> SEQUENCE: 56
aaacctaaaa acaaacccaa caac                                              24

<210> SEQ ID NO 57
<211> LENGTH: 26
<212> TYPE: DNA
<213> ORGANISM: Artificial Sequence
<220> FEATURE:
<223> OTHER INFORMATION: Synthetic primer

<400> SEQUENCE: 57
ggttggtttt aaatttttga ttttag                                            26

<210> SEQ ID NO 58
<211> LENGTH: 25
<212> TYPE: DNA
<213> ORGANISM: Artificial Sequence
<220> FEATURE:
<223> OTHER INFORMATION: Synthetic primer

<400> SEQUENCE: 58
accaatctca ccaaaaccat tataa                                             25
```

EPISOMAL REPROGRAMMING WITH CHEMICALS

The present application claims the priority benefit of U.S. provisional application No. 61/258,120, filed Nov. 4, 2009, the entire contents of which are incorporated herein by reference.

BACKGROUND OF THE INVENTION

1. Field of the Invention

The present invention relates generally to the field of stem cell development. More particularly, it concerns the generation of pluripotent stem cells.

2. Description of Related Art

The unlimited proliferation capability and pluripotent potential of human embryonic stem (ES) cells have offered unprecedented access to all cell types of the human body. Human induced pluripotent stem (iPS) cells derived directly from patient somatic cells with desired genetic background share these two key properties of human ES cells, which made these cells excellent candidates for disease models, drug screening, toxicity testing and transplantation therapies. Initial derivation of human iPS cells employed genome-integrating retroviral or lentiviral vectors to deliver reprogramming transgenes (Lowry et al., 2008; Park et al., 2008; Takahashi et al., 2007; Yu et al., 2007). Such vectors can produce insertional mutations that interfere with the normal functions of human iPS cells and their derivatives, and residual transgene expression that can influence differentiation into specific lineages (Yu et al., 2007), or even result in tumorigenesis (Okita et al., 2007).

iPS cells free of exogenous genetic elements have been derived from mouse embryonic fibroblasts with repeated plasmid transfections (Okita et al., 2008), from mouse liver cells and human fibroblasts with non-integrating adenoviral vectors (Stadtfeld et al., 2008; Zhou and Freed, 2009), from somatic cells with piggyback transposons (Woltjen et al., 2009), from human fibroblasts with oriP/EBNA-1-based episomal vectors (Yu et al., 2009) and protein transduction. Despite these rapid advances, major hurdles remain to prevent the wide use of any single technology that produce high-quality human iPS cells free of exogenous genetic elements. For example, all the current technologies (except the piggyback transposon approach) that allow generation of human iPS cells free of exogenous genetic elements yielded very low reprogramming efficiency. This low efficiency makes it difficult to obtain iPS cells consistently from a variety of easily accessible human somatic cell types, and from cells with different genetic background and donor age. The piggyback transposon approach offers reasonable reprogramming efficiency. However, the removal of transposons from iPS cells can be quite labor-intensive when many donor cell lines are involved.

In addition, despite the high similarity of human iPS cells to human ES cells, there exist significant clone-to-clone variations both in gene expression/epigenetic modifications and in the lineage-specific differentiation potential of human iPS cells. In particular, compared to human ES cells, most human iPS cells exhibit significantly lower neural differentiation potential and no response to LIF (leukemia inhibitory factor), which routinely supports mouse ES cell culture. Moreover, due to the lack of good easily assayable markers for high-quality human iPS cells, selection of high-quality human iPS cell clone can be labor-intensive and time-consuming.

Genetic reprogramming of human somatic cells to induced pluripotent stem cells (iPSCs) could offer replenishable cell sources for transplantation therapies. To fulfill their promise, human iPSCs will ideally be derived and cultured in chemically defined media free of feeder cells, and be free of exogenous DNA (footprint-free). Currently, there is not a simple and efficient feeder-free nonviral method for the generation of footprint-free human iPSCs. Previously efforts of footprint-free human iPSCs by employing episomal vectors for transgene delivery were inefficient and required feeder cells.

Therefore, there remains a need to address the inefficiency or other problems in preparing induced pluripotent stem cells essentially free of exogenous genetic components.

SUMMARY OF THE INVENTION

Aspects of the present invention overcome a major deficiency in the art by providing novel methods for preparing induced pluripotent stem cells essentially free of exogenous vector elements, and thus provide particular advantages in terms of iPS cell applications.

In addition, using small molecules, certain exemplary aspects of the present invention greatly improved the episomal reprogramming efficiency (>70 fold; >300 fold if using transformation-deficient MYC such as LMYC), and established a feeder-free reprogramming condition using chemically defined media for the derivation of footprint-free human iPSCs. These improvements enabled the routine derivation of footprint-free human iPSCs from skin fibroblasts and likely many other cell types, thus making the technology easily adaptable to the clinical-grade production of human iPSCs.

Accordingly, in a first embodiment there is provided a composition comprising a population of iPS cells essentially free of exogenous retroviral elements and a medium comprising externally added signaling inhibitors. In certain aspects, these iPS cells may be substantially free, or preferably essentially free of, exogenous vector or genetic elements. For example, these iPS cells may be derived from one or more human cells. In a further aspect, cells of the population may comprise the genome of a selected human individual, such as a human patient.

In certain aspects, the human cells are primary human cells, which are cells directly obtained from a living human subject, and may exclude the use of an established or immortalized cell line. Some embodiments may include the use of terminally differentiated human cells. Non-limiting examples of the primary human cell include a fibroblast, a keratinocyte, a hematopoietic cell, a mesenchymal cell, an adipose cell, an endothelial cell, a neural cell, a muscle cell, a mammary cell, a liver cell, a kidney cell, a skin cell, a digestive tract cell, a cumulus cell, a gland cell, or a pancreatic islet cell. More specifically, the primary human cell may be a hematopoietic progenitor cell, such as a $CD34^+$ cell. The primary human cell may be obtained from a blood sample, a hair sample, a skin sample, or any sources known to a person of ordinary skill in the art.

The signaling inhibitors may be one or more selected from the group consisting of a glycogen synthase kinase 3 (GSK-3) inhibitor, a mitogen-activated protein kinase kinase (MEK) inhibitor, a transforming growth factor beta (TGF-β) receptor inhibitor, leukemia inhibitory factor (LIF), and a combination thereof. Particularly, the composition comprises the cell population and a combination of GSK-3 inhibitor, MEK inhibitor, TGF-β receptor inhibitor, and optionally, LIF. The medium may further comprise externally added ROCK inhibitor or Myosin II inhibitor. The ROCK inhibitor may be HA-100. The medium may further comprises externally added FGF. In certain aspects, the composition may further comprise a chemically defined medium. Non-limiting examples of a chemically defined medium include TeSR medium, human embryonic cell culture medium, N2B27 medium and derivatives thereof.

The composition may also comprise a matrix component to replace feeder cells to support culture of the cell population. The matrix component for cell adhesion can be any material intended to attach stem cells or feeder cells (if used). Non-limiting examples of the matrix component include collagen, gelatin, poly-L-lysine, poly-D-lysine, vitronectin, laminin, and fibronectin and mixtures thereof, for example, Matrigel™ and lysed cell membrane preparations.

In certain embodiments, the invention involves a method for producing a population of iPS cells, comprising: a) obtaining somatic cells comprising an extra-chromosomal genetic element that expresses one or more reprogramming factors; and b) culturing the somatic cell and/or progeny cells thereof in a reprogramming condition comprising externally added one or more signaling inhibitors such as a GSK-3 inhibitor, a MEK inhibitor, and/or a TGF-β receptor inhibitor, thereby producing a population of iPS cells. In certain aspects, the reprogramming medium may comprise a combination of a GSK-3 inhibitor, a MEK inhibitor, a TGF-β receptor inhibitor, and optionally, LIF.

In further aspects, the reprogramming condition may be essentially free of feeder cells, like irradiated mouse embryonic fibroblast (MEF) feeder cells. The reprogramming condition may comprise a matrix component, such as Matrigel™.

The somatic cell may be a human cell or a primary cell, such as a primary human cell. Examples of the somatic cell may include, be not be limited to, a fibroblast, a keratinocyte, a hematopoietic cell, a mesenchymal cell, an adipose cell, an endothelial cell, a neural cell, a muscle cell, a mammary cell, a liver cell, a kidney cell, a skin cell, a digestive tract cell, a cumulus cell, a gland cell, a pancreatic islet cell. The hematopoietic cell may include any blood cells, such as a hematopoietic progenitor cell (e.g., a $CD34^+$ cell), a T cell, a B cell, or a combination thereof.

In certain aspects, the extra-chromosomal genetic element may be further defined as an episomal vector. For example, the episomal vector may comprise a replication origin and one or more expression cassettes for expression of reprogramming factors. Such one or more of the expression cassettes may further comprise a nucleotide sequence encoding a trans-acting factor that binds to the replication origin to replicate an extra-chromosomal template. Alternatively, the somatic cell may express such a trans-acting factor. The extra-chromosomal genetic element may be any genetic material or nucleic acids, such as DNA or RNA.

Such episomal vectors may be essentially free of bacterial elements. The bacterial elements may be components of the vector backbone that is required for plasmid propagation in bacteria, such as bacterial origin of replication, e.g., the pUC replication origin, and bacterial selection cassette, e.g., Ampicillin selection cassette.

In exemplary embodiments, the replication origin may be a replication origin of a lymphotrophic herpes virus or a gamma herpesvirus, an adenovirus, SV40, a bovine papilloma virus, or a yeast, such as a replication origin of a lymphotrophic herpes virus or a gamma herpesvirus corresponding to oriP of EBV. In a further aspect, the lymphotrophic herpes virus may be Epstein Barr virus (EBV), Kaposi's sarcoma herpes virus (KSHV), Herpes virus saimiri (HS), or Marek's disease virus (MDV).

For replication and transient maintenance of extra-chromosomal genetic elements, the trans-acting factor may be a polypeptide corresponding to, or a derivative of, a wild-type protein of EBNA-1 (EBV nuclear antigen 1) of EBV, preferably in the presence of a replication origin corresponding to OriP of EBV. The derivative may have a reduced ability to activate transcription from an integrated template as compared to wild-type EBNA-1 and thus reduced chances to ectopically activate chromosome genes to cause oncogenic transformation. Meanwhile, the derivative may activate transcription at least 5% that of the corresponding wild-type protein from an extra-chromosomal template after the derivative binds the replication origin.

For reprogramming of somatic cells, certain aspects of the present methods may involve using the reprogramming factors that may comprise one or more selected from the group consisting of Sox, Oct, Nanog, Lin-28, Klf4, c-Myc, and SV40LT, for example, a set of Sox, Oct, Nanog, and optionally Lin-28, a set of Sox, Oct, Klf4, and optionally c-Myc, or a combination of these six factors. In certain aspects, to reduce the possible toxic effect of c-Myc expression, the SV40 large T gene (SV40LT) may be included with c-Myc. In certain aspects to further improve reprogramming efficiency, Myc mutants, variants or homologs that are deficient in transformation may be used. Non-limiting examples include a Myc proto-oncogene family member such as LMYC (NM_001033081), MYC with 41 amino acid deleted at the N-terminus (dN2MYC), or MYC with mutation at amino acid 136 (W136E) (Nakagawa et al. 2010).

In certain aspects, the cells may be cultured in a reprogramming condition having a reprogramming medium comprising signaling inhibitors as described above for at least or about 1, 2, 3, 4, 6, 7, 8, 9, 10, 11, 12, 13, 14, 15, 16, 17, 18, 19, 20 days, or any range derivable therein. The reprogramming condition may last a period including at least from about one day to five days after introduction of the extra-chromosomal element into the somatic cells. The starting and ending time points may be selected from the 1, 2, 3, 4, 6, 7, 8, 9, 10, 11, 12, 13, 14, 15, 16, 17, 18, 19, 20 days, or any range derivable therein after the introduction, for example, from about one day to fifteen days post-transfection of the genetic elements.

After reprogramming, the cells may be transferred to an expansion condition having an expansion medium. The expansion medium may be essentially free of externally added GSK-3 inhibitor, MEK inhibitor, and TGF-β receptor inhibitor. In certain aspects, the expansion medium may have one or more of the signaling inhibitors and/or LIF. In certain aspects, by using this expansion condition, for example, a normal ES cell culture medium or TeSR medium, human iPS cells similar to human ES cells may be obtained.

In certain aspects, the methods may further comprise selecting the iPS cells, for example, based on one or more embryonic cell characteristics, such as an ES cell-like morphology. In a further aspect, the methods may comprise culturing the selected iPS cells in the expansion medium.

As an additional advantage, the culture conditions described herein, such as the reprogramming condition or expansion condition, may be essentially free of feeder cells. The feeder-free condition may improve the industrial and therapeutic application by reducing variability and side effects from feeder cells. For example, a matrix component may be used in place of feeder cells. To increase episomal reprogramming in feeder-free conditions, signaling inhibitors and/or FGF may be added to the reprogramming medium.

In order to increase the cloning efficiency of pluripotent stem cells, the reprogramming medium, the first, or the second expansion medium may further comprise a Rho-associated kinase (ROCK) inhibitor or myosin II inhibitor, such as HA-100 or blebbistatin. To further benefit episomal reprogramming and/or enhance proliferation of reprogrammed cells, in some aspects, fibroblast growth factor (FGF) may be added to the reprogramming medium. Externally added FGF or signaling inhibitors may be at an amount of at least, about or at most 0.1, 1, 5, 10, 15, 20, 25, 30, 35, 40, 45, 50, 55, 60, 65, 70, 75, 80, 90, 100, 150, 200 ng/ml, at least, about, or at most 0.05, 0.1, 0.2, 0.2, 0.3, 0.4, 0.5, 0.6, 0.7, 0.8, 0.9, 1, 1.5, 2, 2.5, 3, 4, 5, 6, 7, 8, 9, 10 µM, or any range derivable therein, or any concentration effective for improving episomal reprogramming. In specific embodiments, high concentration of FGF may be used, for example, about 40 to 200 ng/ml, or more particularly, about 100 ng/ml.

In some aspects, the reprogramming medium or the expansion medium may be chemically defined, such as TeSR medium, human embryonic cell culture medium, or N2B27 medium. In certain aspects, the reprogramming medium may be a medium essentially free of TGFβ, such as N2B27 medium. The expansion medium may be TeSR medium or mTeSR medium.

For example, the GSK-3 inhibitor may be CHIR99021; the MEK inhibitor may be PD0325901; the TGF-β receptor inhibitor may be A-83-01. A population of iPS cells produced according to the above methods may also be provided.

In certain aspects, starting cells for the present methods may comprise at least or about $10^4$, $10^5$ $10^6$, $10^7$, $10^8$, $10^9$, $10^{10}$, $10^{11}$, $10^{12}$, $10^{13}$ cells or any range derivable therein. The starting cell population may have a seeding density of at least or about 10, $10^1$, $10^2$, $10^3$, $10^4$, $10^5$, $10^6$, $10^7$, $10^8$ cells/ml, or any range derivable therein.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. Episomal reprogramming vectors. pEF: the eukaryotic elongation factor 1α promoter; pCMV: the cytomegalovirus immediate-early promoter. Transgenes and other features of vectors are indicated by different colors as shown. FIG. 1B. Effects of different combinations of chemical compounds on episomal reprogramming efficiency. FF medium: human foreskin fibroblast culture medium; CM: human ES cell culture medium previously conditioned with irradiated mouse embryonic fibroblast feeder cells. bFGF was used at 100 ng/ml final concentration. B: BIX01294 (1 µM); P: PD0325901 (0.5 µM); C: CHIR99021 (3 µM); A: A-83-01 (0.5 µM). Total: total # of alkaline phosphatase positive iPS cell colonies; Large: # of large-size good undifferentiated alkaline phosphatase positive iPS cell colonies. FIG. 1C. Images of a good iPS cell colony obtained by episomal reprogramming in the presence of chemical compounds. Left: bright-field; right: alkaline phosphatase staining.

FIG. 2A. Effects of bFGF and different combinations of chemical compounds on episomal reprogramming efficiency. FF medium: human foreskin fibroblast culture medium; CM: human ES cell culture medium previously conditioned with irradiated mouse embryonic fibroblast feeder cells. bFGF was used at 100 ng/ml final concentration. H: HA-100 (10 µM); B: BIX01294 (1 µM); P: PD0325901 (0.5 µM); C: CHIR99021 (3 µM); A: A-83-01 (0.5 µM); L: hLIF (10 ng/ml). Total: total # of alkaline phosphatase positive iPS cell colonies; Large: # of large-size good undifferentiated alkaline phosphatase positive iPS cell colonies. FIG. 2B. Timing of chemical compound treatment on episomal reprogramming efficiency. CM supplemented with bFGF (100 ng/ml) and HA-100 (10 µM) was used in reprogramming culture.

FIG. 3A. Images of differentiated human H1 ES cells (p44) and normal human ES cell-like iPS cells (p20, derived from human foreskin fibroblasts by episomal reprogramming in the absence of chemical treatment) following 5 day-culture in CM (human ES cell culture medium previously conditioned with irradiated mouse embryonic fibroblast feeder cells) supplemented with PD0325901 (0.5 µM), CHIR99021 (3 µM), A-83-01 (0.5 µM) and hLIF (10 ng/ml). FIG. 3B. Bright-field image of normal human ES cell-like iPS cells derived from a 42-year old adult skin biopsy with episomal reprogramming in the presence of PD0325901 (0.5 µM), CHIR99021 (3 µM) and A-83-01 (0.5 µM). Chemical compounds were removed 3 days prior to colony picking (day 23 post nucleofection). iPS cell colonies were picked and expanded on irradiated mouse embryonic fibroblast (MEF) feeder cells in human ES cell culture medium supplemented with bFGF (100 ng/ml) in the absence of chemical compounds. FIG. 3C. Bright-field image of an intermediate stage of iPS (piPSC for partially reprogrammed iPSCs) cells derived from human foreskin fibroblasts with episomal reprogramming in the presence of PD0325901 (0.5 µM), CHIR99021 (3 µM), A-83-01 (0.5 µM) and hLIF (10 ng/ml).

Chemical compounds were present throughout the reprogramming culture. piPS cell colonies were picked and expanded on MEF feeder cells in CM supplemented with PD0325901 (0.5 µM), CHIR99021 (3 µM), A-83-01 (0.5 µM) and hLIF (10 ng/ml). FIG. 3D. Bright-field image of a rosette cluster (neural differentiation) from piPS cells cultured in human ES cell culture medium supplemented with bFGF (100 ng/ml) following withdrawal of chemical compounds.

FIG. 4A. Effect of different culture medium on episomal reprogramming in the presence of PD0325901 (0.5 µM), CHIR99021 (3 µM), A-83-01 (0.5 µM) and hLIF (10 ng/ml). FF medium: human foreskin fibroblast culture medium; CM: human ES cell culture medium previously conditioned with irradiated mouse embryonic fibroblast feeder cells. bFGF was used at 100 ng/ml final concentration. H: HA-100 (10 µM); B: BIX01294 (1 µM); P: PD0325901 (0.5 µM); C: CHIR99021 (3 µM); A: A-83-01 (0.5 µM); L: hLIF (10 ng/ml). Total: total # of alkaline phosphatase positive iPS cell colonies; Large: # of large-size good undifferentiated alkaline phosphatase positive iPS cell colonies. FIG. 4B. Sketch of the three-step reprogramming process for the derivation of normal human ES cell-like iPS cells and piPS cells.

FIG. 5A. Effects of PD0325901 (P, 0.5 µM), CHIR99021(C, 3 µM), A-83-01(A, 0.5 µM), hLIF (L, 1000 U/ml) and HA-100 (H, 10 µM) on episomal reprogramming. FIG. 5B Temporal requirement of small molecule treatment for improved episomal reprogramming. Transfected human foreskin fibroblasts were plated to MEF feeder cells. MEF-conditioned human ESC medium supplemented with 100 ng/ml bFGF (CM100) and small molecules was used to support reprogramming. Alkaline phosphatase positive iPSC colonies were counted on day 22-23 post-transfection. The number of iPSC colonies was from ~0.33×10$^6$ input cells. Data shown are mean±standard error (s.e.m.) (n=3). FIG. 5C. Differentiation of the newly derived iPSCs (p3) in the presence of small molecules. When picked and expanded in human ESC medium or MEF-conditioned human ESC medium supplemented with small molecules on MEF feeder cells, the iPSCs derived with the continuous presence of small molecules exhibited extensive differentiation. The addition of bFGF in the culture medium had no effect. Black arrow: undifferentiated iPSC colonies; white arrows: differentiated colonies. Scale bars: 100 µm.

FIG. 6A. Effects of MEF feeder cells, Matrigel™ and culture media on episomal reprogramming. Transfected human foreskin fibroblasts (p6) were plated to MEF feeder cell-seeded or Matrigel™-coated 10-cm dishes, and subjected to different reprogramming culture conditions. Alkaline phosphatase positive (AP$^+$) colonies were counted on day 18-21 post-transfection. The number of AP+ colonies was from ~0.33×10$^6$ input cells. Data shown are mean±s.e.m. (n=3). N2B27: DMEM/F12 medium supplemented with N-2 and B-27; N2B27-100: N2B27 medium supplemented with 100 ng/ml bFGF. *marks piPSCs. FIG. 6B. Bright-field images of a piPSC colony from test 2 and a human ESC-like iPSC colony from test 1, 3 and 4. Scale bars: 100 µm. FIG. 6C. Quantitative RT-PCR analysis of OCT4 and NANOG expression in piPSC clone 1 to 4 (p3). Total: both endogenous and transgene expression. Human H1 ESCs (H1ESC, p32) were used as a control. Data shown are mean±s.e.m. (n=3). FIG. 6D. Temporal requirement of small molecule treatment for feeder-free episomal reprogramming using defined culture media. Transfected human foreskin fibroblasts (p7) were plated to Matrigel™-coated 10-cm dishes. N2B27-100 medium supplemented with PCALH was used to support reprogramming for different time windows (stage 2) followed by mTeSR1 for expansion. Alkaline phosphatase positive iPSC colonies were counted on day 22 post-transfection. The number of iPSC colonies was from ~0.33×10$^6$ input cells. Data shown are mean±s.e.m. (n=3).

FIG. 7A. Bright-field image of iPSCs derived from human adult skin fibroblasts (iPS(SK46) clone 2). Scale bar: 100 µm. FIG. 7B. G-banding chromosome analysis of iPS(SK46) clone 2 (p17). FIG. 7C. PCR analysis of reprogramming vectors in iPSCs. E: episomal DNA; G: genomic DNA; NF: neonatal foreskin fibroblasts (p5); iPSF7 clone 1 to 3: iPSCs derived from neonatal foreskin fibroblasts (p26); AF: adult skin fibroblasts (p6); iPS(SK46) clone 1 to 3: iPSCs derived from adult skin fibroblasts (p22). piPSC derived from human foreskin fibroblasts (p4) were used as controls. T-OCT4: transgene OCT4; T-SOX2: transgene SOX2; T-NANOG: transgene NANOG; T-LIN28: transgene LIN28; T-c-MYC: transgene c-MYC; T1-KLF4: transgene KLF4 (1); T2-KLF4: transgene KLF4 (2); T-SV40LT: transgene SV40LT; OCT4: endogenous OCT4. 32 PCR cycles were used for all primer sets. FIG. 7D. Quantitative RT-PCR analysis of the endogenous OCT4, NANOG, SOX2 and LIN28 expression in iPSC clones. Data shown are mean±s.e.m. (n=3). FIG. 7E. Bisulfite-sequencing analysis of the methylation status of the OCT4 and NANOG promoters in iPSC clones. Open circles indicate unmethylated, and filled circles indicate methylated CpG dinucleotides. FIG. 7F. Hematoxylin and eosin staining of teratoma sections of iPSC (SK46) clone 2. Teratomas were obtained from all iPSC clones. Left panel: neural tissue (ectoderm); middle panel: cartilage (mesoderm), right panel: gut epithelium (endoderm). Scale bars: 100 µm.

FIG. 8A. Reprogramming human foreskin fibroblasts with episomal vectors. Transfected human foreskin fibroblasts (HFFs, p6) were plated to Matrigel™-coated 10-cm dishes in foreskin fibroblast culture medium. N2B27-100 medium supplemented with PD0325901 (P, 0.5 µM), CHIR99021(C, 3 µM), A-83-01(A, 0.5 µM), hLIF (L, 1000 U/ml) and HA-100 (H, 10 µM) (PCALH) was used to support reprogramming between day 1 and 13 post-transfection, followed by mTeSR1 between day 14 and 21 post-transfection. The number of iPSC colonies was from ~0.33×10$^6$ input cells. Data shown are mean±standard error (s.e.m.) (n=3). 7F-1 (pEP4EO2SCK2MEN2L and pEP4EO2SET2K); 7F-2 (pEP4EO2SEN2K, pCEP4-M2L and pEP4EO2SET2K); 5F (pEP4EO2SEN2L and pEP4EO2SET2N). All vector maps are shown in FIG. 12. FIG. 8B. Reprogramming adipose tissue-derived stem cells (AdSCs) with episomal vectors. AdSCs (Zenbio, Research Triangle Park, NC) were cultured in MesenCult®-XF culture medium (STEMCELL Technologies Inc., Vancouver, BC, V5Z 1B3, Canada) supplemented with 1× Glutamax (Invitrogen) on 10-cm dishes coated with human collagen I (60 µg per 10-cm dish, STEMCELL Technologies Inc.) and fibronectin (18 µg per 10-cm dish, Invitrogen). Transfected AdSCs (p9, Amaxa VPE-1001 with program A-33) were plated to Matrigel™-coated 10-cm dishes in AdSC culture medium. N2B27-100 medium supplemented with PCALH was used to support reprogramming between day 2 and 13 post-transfection, followed by mTeSR1 between day 13 and 21 post-transfection. The number of iPSC colonies was from ~0.35×10$^6$ input cells. Data shown are mean±standard error (s.e.m.) (n=2). FIG. 8C. Reprogramming cord blood (CB)-derived CD34+ cells with episomal vectors. Prior to transfection, CB-derived CD34+ cells (STEMCELL Technologies Inc.) were cultured for 4 days on a fibronectin-coated 6-well plate in CB CD34+ cell expansion medium: StemSpan SFEM (STEMCELL Technologies Inc.) supplemented with 1× ExCyte medium supplement (Millipore, Billerica, Mass.), 1× Glutamax, 250 ng/ml SCF (Peprotech, Rocky Hill, N.J.), 250 ng/ml FLT3L (Peprotech), 100 ng/ml TPO (Peprotech), 20 ng/ml IL-3 (Peprotech), 50 ng/ml IL-6 (Peprotech) and 10 ng/ml sIL6-R (Peprotech). Transfected CB cells (Amaxa VPA-1003 with program T-16) were plated to fibronectin/Matrigel™-coated 6-well plate in CB CD34+ cell expansion medium. N2B27-100 medium supplemented with PCALH was used to support reprogramming between day 2 and 11 post-transfection, followed by mTeSR1 between day 11 and 17 post-transfection. The number of iPSC colonies was from ~0.33×10$^6$ input cells (after 4 day culture). Data shown are mean±standard error (s.e.m.) (n=3).

FIG. 10A. Flow cytometry expression analysis of human ESC-specific cell surface markers (SSEA-3, SSEA-4, Tra-1-60 and Tra-1-81) and a fibroblast marker CD44 in piPSCs (p6). Unfilled: isotype control; filled: antigen staining. FIG. 10B. PCR analysis of reprogramming vectors in the episomal DNA isolated from piPSCs (p7). Lane 1: transgene OCT4 (T-OCT4); Lane 2: transgene NANOG (T-NANOG); Lane 3: transgene KLF4 (1) (T1-KLF4); Lane 4: transgene KLF4 (2) (T2-KLF4); Lane 5: transgene SV40LT (T-SV40LT); Lane 6: transgene SOX2 (T-SOX2); Lane 7: transgene LIN28 (T-LIN28); Lane 8: transgene c-MYC (T-c-MYC); Lane 9: endogenous OCT4 (OCT4). FIG. 10C. Temporal requirement of small molecule treatment for feeder-free episomal reprogramming using mTeSR1. Transfected human foreskin fibroblasts (p7) were plated to Matrigel™-coated 10-cm dishes. mTeSR1 supplemented with small molecules (PCALH) was used to support reprogramming for different time windows (stage 2) followed by mTeSR1 without small molecules for expansion. Alkaline phosphatase positive iPSC colonies were counted on day 22 post-transfection. The number of iPSC colonies was from ~0.33×10$^6$ input cells. Data shown are mean±s.e.m. (n=3).

FIG. 11A. Brightfield image of iPSCs derived from human foreskin fibroblasts (iPSF7 clone 1). Scale bar: 100 μm. FIG. 11B. G-banding chromosome analysis of iPSF7 clone 1 (p18). FIG. 11C. RT-PCR analysis of transgene expression in iPSC clones. NF: neonatal foreskin fibroblasts (p5); iPSF7 clone 1 to 3: iPSCs derived from neonatal foreskin fibroblasts (p26); AF: adult skin fibroblasts (p6); iPS(SK46) clone 1 to 3: iPSCs derived from adult skin fibroblasts (p22). H1ESC (p32) and piPSC (p4) derived from human foreskin fibroblasts were used as controls. T-OCT4: transgene OCT4; T-50×2: transgene SOX2; T-NANOG: transgene NANOG; T-LIN28: transgene LIN28; T-c-MYC: transgene c-MYC; T1-KLF4: transgene KLF4 (1); T2-KLF4: transgene KLF4 (2); T-SV40LT: transgene SV40LT; OCT4: endogenous OCT4; GAPDH: endogenous control. 32 PCR cycles were used for all primer sets except for T-OCT4 (30 cycles). FIG. 11D. Flow cytometry expression analysis of human ESC-specific cell surface markers (SSEA-3, SSEA-4, Tra-1-60 and Tra-1-81) and the fibroblast-enriched marker CD44. Unfilled: isotype control; filled: antigen staining. FIG. 11E. Hematoxylin and eosin staining of teratoma sections of iPSF7 clone 1. Top panel: neural tissue (ectoderm); middle panel: cartilage (mesoderm); bottom panel: gut epithelium (endoderm). Scale bars: 100 μm.

DESCRIPTION OF ILLUSTRATIVE EMBODIMENTS

I. Introduction

Figure 1A:
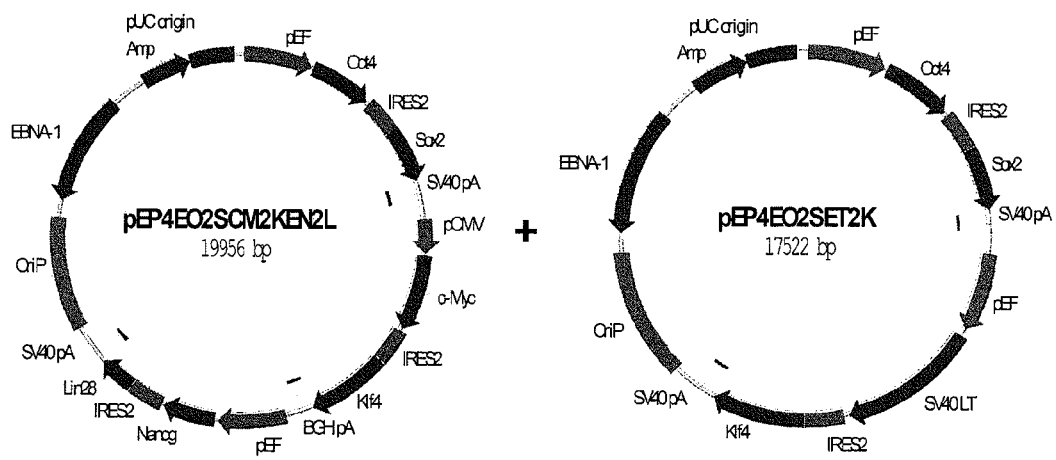
FIGS. 1A-1C. Improving episomal reprogramming of human foreskin fibroblasts with small chemical compounds.

The present invention is based, in part, on the surprising discovery that inhibitors of intracellular signaling may be used to improve episomal reprogramming efficiency and kinetics by culturing the reprogrammed cells in the presence of a GSK-3 inhibitor, a MEK inhibitor, and a TGF-β receptor inhibitor. Although it has been reported that retroviral reprogramming of human fibroblast cells was improved by using a chemical cocktail including a MEK inhibitor and a TGF-β receptor inhibitor (Lin et al., 2009), retroviral (including lentiviral) reprogramming is fundamentally different from episomal reprogramming for the genome integration of retroviral vector elements and persistent transgene expression of integrated vector elements. For example, as demonstrated in the Examples, episomal reprogramming in the presence of a combination of these three inhibitors resulted in an unexpectedly high reprogramming efficiency compared with that in the presence of a MEK inhibitor and a TGF-β receptor inhibitor, which only has minimal enhancement over the baseline The use of an episomal vector in the practice of certain aspects of the present invention has several advantages over vectors which integrate into the genome. First, it reduces the background of non-relevant phenotypic alterations occurring as a result of random integrations into DNA. Second, the episomes reduce the possibility of insertional mutagenesis, which could lead to tumor formation. Third, replication of episomal vectors can result in gradual loss of exogenous vector elements, which leave the cells with minimal exogenous genetic modification. However, the low reprogramming efficiency has hurdled the use of episomal vectors in reprogramming of somatic cells, which could be addressed by certain aspects of the present invention.

In further aspects, methods to produce iPS cells with improved industrial and clinical applications have been developed. The method may involve using a feeder-free condition to produce iPS cells essentially free of exogenous genetic elements and therefore avoid problems brought by persistence or mutagenic effects of exogenous genetic elements and variability or undesired effects of feeder cells.

Further advances in the composition and methods for production of iPS cell populations are also described below.

II. Definitions

A "primary cell," as used herein, refers to a cell directly obtained from a living organism or a progeny thereof without being established or immobilized into a cell line. A "human primary cell" refers to a primary cell obtained from a living human subject.

"Embryonic stem (ES) cells" are pluripotent stem cells derived from early embryos. An ES cell was first established in 1981, which has also been applied to production of knockout mice since 1989. In 1998, a human ES cell was established, which is currently becoming available for regenerative medicine.

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as fibroblast, a hematopoietic cell, a myocyte, a neuron, an epidermal cell, or the like, by reprogramming.

"Pluripotency" refers to a stem cell that has the potential to differentiate into all cells constituting one or more tissues or organs, or preferably, any of the three germ layers: endoderm (interior stomach lining, gastrointestinal tract, the lungs), mesoderm (muscle, bone, blood, urogenital), or ectoderm (epidermal tissues and nervous system). "Pluripotent stem cells" used herein refer to cells that can differentiate into cells derived from any of the three germ layers, for example, direct descendants of totipotent cells, embryonic stem cell, or induced pluripotent cells.

As used herein, the term "somatic cell" refers to any cell other than germ cells, such as an egg, a sperm, or the like, which does not directly transfer its DNA to the next generation. Typically, somatic cells have limited or no pluripotency. Somatic cells used herein may be naturally-occurring or genetically modified.

"Reprogramming" is a process that confers on a cell a measurably increased capacity to form progeny of at least one new cell type, either in culture or in vivo, than it would have under the same conditions without reprogramming. More specifically, reprogramming is a process that confers on a somatic cell a pluripotent potential. This means that after sufficient proliferation, a measurable proportion of progeny having phenotypic characteristics of the new cell type if essentially no such progeny could form before reprogramming; otherwise, the proportion having characteristics of the new cell type is measurably more than before reprogramming. Under certain conditions, the proportion of progeny with characteristics of the new cell type may be at least about 0.05%, 0.1%, 0.5%, 1%, 5%, 25% or more in the in order of increasing preference.

Cells are "substantially free" of exogenous genetic elements or vector elements, as used herein, when they have less that 10% of the element(s), and are "essentially free" of exogenous genetic elements or vector elements when they have less than 1% of the element(s). However, even more desirable are cell populations wherein less than 0.5% or less than 0.1% of the total cell population comprise exogenous genetic elements or vector elements. Medium are "essentially free" of certain reagents, such as MEK inhibitors, GSK inhibitors, TGF-βreceptor inhibitors, LIF, when the medium have a level of these reagents lower than a detectable level using conventional detection methods known to a person of ordinary skill in the art.

The term "exogenous," when used in relation to a protein, gene, nucleic acid, polynucleotide, genetic elements, or vector elements in a cell or organism, refers to a protein, gene, nucleic acid, polynucleotide, genetic element or vector element which has been introduced into the cell or organism by artificial or natural means, or in relation to a cell, refers to a cell which was isolated and subsequently introduced to other cells or to an organism by artificial or natural means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

An "origin of replication" ("ori") or "replication origin" is a DNA sequence, e.g., in a lymphotrophic herpes virus, that when present in a plasmid in a cell is capable of maintaining linked sequences in the plasmid, and/or a site at or near where DNA synthesis initiates. An ori for EBV includes FR sequences (20 imperfect copies of a 30 bp repeat), and preferably DS sequences, however, other sites in EBV bind EBNA-1, e.g., Rep* sequences can substitute for DS as an origin of replication (Kirchmaier and Sugden, 1998). Thus, a replication origin of EBV includes FR, DS or Rep* sequences or any functionally equivalent sequences through nucleic acid modifications or synthetic combination derived therefrom. For example, the present invention may also use genetically engineered replication origin of EBV, such as by insertion or mutation of individual elements, as specifically described in Lindner et al (2008).

A "lymphotrophic" herpes virus is a herpes virus that replicates in a lymphoblast (e.g., a human B lymphoblast) or other cell types and replicates extra-chromosomally for at least a part of its natural life-cycle. After infecting a host, these viruses latently infect the host by maintaining the viral genome as a plasmid. Herpes simplex virus (HSV) is not a "lymphotrophic" herpes virus. Exemplary lymphotropic herpes viruses include, but are not limited to EBV, Kaposi's sarcoma herpes virus (KSHV), Herpes virus saimiri (HS) and Marek's disease virus (MDV).

A "vector" or "construct" (sometimes referred to as gene delivery or gene transfer "vehicle") refers to a macromolecule or complex of molecules comprising a polynucleotide to be delivered to a host cell, either in vitro or in vivo.

A "plasmid", a common type of a vector, is an extra-chromosomal DNA molecule separate from the chromosomal DNA which is capable of replicating independently of the chromosomal DNA. In certain cases, it is circular and double-stranded.

A "template" as used herein is a DNA or RNA molecule which contains a replication origin. An "integrated template" is one which is stably maintained in the genome of the cell, e.g., integrated into a chromosome of that cell. An "extra-chromosomal template" is one which is maintained stably maintained in a cell but which is not integrated into the chromosome.

By "expression construct" or "expression cassette" is meant a nucleic acid molecule that is capable of directing transcription. An expression construct includes, at the least, a promoter or a structure functionally equivalent to a promoter. Additional elements, such as an enhancer, and/or a transcription termination signal, may also be included. A nucleic acid molecule may be DNA or RNA.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

III. iPS Cells

Induced pluripotent stem cells, commonly abbreviated as iPS cells or iPSCs, are a type of pluripotent stem cell artificially derived from a non-pluripotent cell, typically an adult somatic cell. Induced pluripotent stem cells are believed to be similar if not identical to natural pluripotent stem cells, such as embryonic stem cells in many respects, such as in terms of the expression of certain stem cell genes and proteins, chromatin methylation patterns, doubling time, embryoid body formation, teratoma formation, viable chimera formation, and potency and differentiability, but the full extent of their relation to natural pluripotent stem cells is still being assessed.

Generation of induced pluripotent cells derived from human tissue other than of embryonic origin is desired to alleviate ethical concerns regarding experimental use of embryos and embryonic tissue. The promise of therapeutic applications from induced pluripotent cells has been touted. Medical applications include treatments for Alzheimer's disease, Diabetes and Spinal cord injuries to name a few. Other applications include disease modeling and pharmaceutical drug screening.

IPS cells were first produced in 2006 (Takahashi et al., 2006) from mouse cells and in 2007 from human cells (Takahashi et al., 2007; Yu et al, 2007). This has been cited as an important advancement in stem cell research, as it may allow researchers to obtain pluripotent stem cells, which are important in research and potentially have therapeutic uses, without the controversial use of embryos. The first successful demonstration of generating induced pluripotent cells (iPS cells) from mouse or human tissue involved the use of retroviral vectors expressing a specific set of transcription factors. Research in the laboratories of James Thomson and Shinya Yamanaka has demonstrated that introduction of specific transcription factors by retroviral vectors into mouse or human fibroblasts is sufficient to reprogram those cells to undifferentiated pluripotent stems cells. The factors used by Thomson include Oct4, Sox2, Nanog and Lin28. The factors used by Yamanaka include Oct4, Sox2, Klf4 and c-Myc. Reprogramming via either gene set is accomplished by integration into the host cell genome and expression of the transcription factors. Oct4 and Sox2 appear to be essential transcription factors required for reprogramming. The efficiency of reprogramming is low with frequencies in the range of 0.01-0.02% of the starting cell population.

To improve current reprogramming methods, in certain embodiments of the invention, there are disclosed methods of reprogramming somatic cells by introducing reprogramming factors into somatic cells with extra-chromosomal genetic elements followed by culturing in a reprogramming medium comprising one or more signaling inhibitors as described above. The progeny of these cells could be identical to embryonic stem cells in various aspects as described below, but essentially free of exogenous genetic elements.

Original embryonic stem cells (ES cells) are pluripotent stem cells derived from the inner cell mass of the blastocyst, an early-stage embryo. ES cells are distinguished by two distinctive properties: their pluripotency and their capability to self-renew themselves indefinitely. ES cells are pluripotent, that is, they are able to differentiate into all derivatives of the three primary germ layers: ectoderm, endoderm, and mesoderm. Additionally, under defined conditions, embryonic stem cells are capable of propagating themselves indefinitely. This allows embryonic stem cells to be employed as useful tools for both research and regenerative medicine, because they can produce limitless numbers of themselves for continued research or clinical use.

However, there are notable differences between mouse and human ES cells. Human ES cells, when discovered by James Thomson, were found to be different than mouse ES cells in their potency and in their culture conditions, notable by being totally non-responsive to LIF (a required element in culturing mouse ES cells), which results from an inactive leukemia inhibitory factor pathway in human ES cells. Existing human IPS cells are similar to human ES cells in these regards, therefore they could termed human ES cell-like iPS cells.

IV. Extra-Chromosomal Genetic Elements for Reprogramming

Induction of pluripotent stem cells from human somatic cells has been achieved using retroviruses or lentiviral vectors for ectopic expression of reprogramming genes. Recombinant retroviruses such as the Moloney murine leukemia virus have the ability to integrate into the host genome in a stable fashion. They contain a reverse transcriptase which allows integration into the host genome. Lentiviruses are a subclass of retroviruses. They are widely adapted as vectors thanks to their ability to integrate into the genome of non-dividing as well as dividing cells. The viral genome in the form of RNA is reverse-transcribed when the virus enters the cell to produce DNA, which is then inserted into the genome at a random position by the viral integrase enzyme. Therefore, current technology of successful reprogramming is dependent on integration-based viral approaches.

However, with the present technology, targeted integration is still no routine (Bode et al., 2000) and the conventional alternative, random integration, may lead to insertional mutagenesis with unpredictable consequences in induced pluripotent stem cells. For the same reasons expression of the transgene can not be controlled since it is dependent on the chromatin context of the integration site (Baer et al., 2000). High level of expression can only be achieved at favorable genomic loci but the danger exists that integration into highly expressed sites interferes with vital cellular functions of induced pluripotent stem cells.

In addition, there is increasing evidence for the existence of cellular defense mechanisms against foreign DNA which operate by down-regulating transgenes in a process that is accompanied by DNA methylation (Bingham, 1997, Garrick et al., 1998). Furthermore, viral components may act along with other factors to transform cells. Accompanied by the continual expression from a number of viral genes, the persistence of at least part of the viral genome within the cell may cause cell transformation. These genes may interfere with a cell's signaling pathway causing the observed phenotypic changes of the cell, leading to a transformed cell showing increased cell division, which is favorable to the virus.

Therefore, in certain embodiments, the present invention develops novel methods to generate induced pluripotent stem cells essentially free of exogenous genetic elements, such as from retroviral or lentiviral vector elements used in the previous methods. These methods in the present invention make use of extra-chromosomally replicating vectors, or vectors capable of replicating episomally (see U.S. application Ser. No. 12/478,154, incorporated herein by reference), in combination with culturing reprogrammed cells in the presence of cellular signaling inhibitors to achieve optimal reprogramming efficiency and kinetics.

A number of DNA viruses, such as adenoviruses, Simian vacuolating virus 40 (SV40), bovine papilloma virus (BPV), or budding yeast ARS (Autonomously Replicating Sequences)-containing plasmids replicate extra-chromosomally in mammalian cells. These episomal plasmids are intrinsically free from all these disadvantages (Bode et al., 2001) associated with integrating vectors. A lymphotrophic herpes virus-based system including Epstein Barr Virus (EBV) may also replicate extra-chromosomally and help deliver reprogramming genes to somatic cells.

For example, the episomal vector-based approach used in the invention extracts robust elements necessary for the successful replication and maintenance of an EBV element-based system without compromising the system's tractability in a clinical setting as described in detail below. The useful EBV elements are OriP and EBNA-1, or their variants or functional equivalents. An additional advantage of this system is that these exogenous elements will be lost with time after being introduced into cells, leading to self-sustained iPS cells essentially free of these elements.

A. Epstein-Barr Virus

The Epstein-Barr Virus (EBV), also called Human herpesvirus 4 (HHV-4), is a virus of the herpes family (which includes Herpes simplex virus and Cytomegalovirus), and is one of the most common viruses in humans. EBV maintains its genome extra-chromosomally and works in collaboration with host cell machinery for efficient replication and maintenance (Lindner and Sugden, 2007), relying solely on two essential features for its replication and its retention within cells during cell division (Yates et al. 1985; Yates et al. 1984). One element, commonly referred to as oriP, exists in cis and serves as the origin of replication. The other factor, EBNA-1, functions in trans by binding to sequences within oriP to promote replication and maintenance of the plasmid DNA. As a non-limiting example, certain aspects of the invention extract these two features and use them in the context of a vector to shuttle the genes necessary for reprogramming somatic cells to facilitate the replication and sustained expression of these genes over conventional plasmids.

B. Replication Origin

In certain aspects, a replication origin of EBV, OriP, may be used. OriP is the site at or near which DNA replication initiates and is composed of two cis-acting sequences approximately 1 kilobase pair apart known as the family of repeats (FR) and the dyad symmetry (DS).

FR is composed of 21 imperfect copies of a 30 bp repeat and contains 20 high affinity EBNA-1-binding sites. When FR is bound by EBNA-1, it both serves as a transcriptional enhancer of promoters in cis up to 10 kb away (Reisman and Sugden, 1986; Yates, 1988; Sugden and Warren, 1989; Wysokenski and Yates, 1989; Gahn and Sugden, 1995; Kennedy and Sugden, 2003; Altmann et al., 2006), and contributes to the nuclear retention and faithful maintenance of FR containing plasmids (Langle-Rouault et al., 1998; Kirchmaier and Sugden, 1995; Wang et al., 2006; Nanbo and Sugden, 2007). The efficient partitioning of oriP plasmids is also likely attributable to FR. While the virus has evolved to maintain 20 EBNA-1-binding sites in FR, efficient plasmid maintenance requires only seven of these sites, and can be reconstituted by a polymer of three copies of DS, having a total of 12 EBNA-1-binding sites (Wysokenski and Yates, 1989).

The dyad symmetry element (DS) is sufficient for initiation of DNA synthesis in the presence of EBNA-1 (Aiyar et al., 1998; Yates et al., 2000), and initiation occurs either at or near DS (Gahn and Schildkraut, 1989; Niller et al., 1995). Termination of viral DNA synthesis is thought to occur at FR, because when FR is bound by EBNA-1 it functions as a replication fork barrier as observed by 2D gel electrophoresis (Gahn and Schildkraut, 1989; Ermakova et al., 1996; Wang et al., 2006). Initiation of DNA synthesis from DS is licensed to once-per-cell-cycle (Adams, 1987; Yates and Guan, 1991), and is regulated by the components of the cellular replication system (Chaudhuri et al., 2001; Ritzi et al., 2003; Dhar et al., 2001; Schepers et al., 2001; Zhou et al., 2005; Julien et al., 2004). DS contains four EBNA-1-binding sites, albeit with lower affinity than those found in FR (Reisman et al., 1985). The topology of DS is such that the four binding sites are arranged as two pairs of sites, with 21 bp center-to-center spacing between each pair and 33 bp center-to-center spacing between the two non-paired internal binding sites (Baer et al., 1984; Rawlins et al., 1985).

The functional roles of the elements within DS have been confirmed by studies of another region of EBV's genome, termed Rep*, which was identified as an element that can substitute for DS inefficiently (Kirchmaier and Sugden, 1998). Polymerizing Rep* eight times yielded an element as efficient as DS in its support of replication (Wang et al., 2006). Biochemical dissection of Rep* identified a pair of EBNA-1-binding sites with a 21 bp center-to-center spacing critical for its replicative function (ibid). The minimal replicator of Rep* was found to be the pair of EBNA-1-binding sites, as replicative function was retained even after all flanking sequences in the polymer were replaced with sequences derived from lambda phage. Comparisons of DS and Rep* have revealed a common mechanism: these replicators support the initiation of DNA synthesis by recruiting the cellular replicative machinery via a pair of appropriately spaced sites, bent and bound by EBNA-1.

There are other extra-chromosomal, licensed plasmids that replicate in mammalian cells that are unrelated to EBV and in some ways appear similar to the zone of initiation within the Raji strain of EBV. Hans Lipps and his colleagues have developed and studied plasmids that contain "nuclear scaffold/matrix attachment regions" (S/MARs) and a robust transcriptional unit (Piechaczek et al., 1999; Jenke et al., 2004). Their S/MAR is derived from the human interferon-beta gene, is A/T rich, and operationally defined by its association with the nuclear matrix and its preferential unwinding at low ionic strength or when embedded in supercoiled DNA (Bode et al., 1992). These plasmids replicate semiconservatively, bind ORC proteins, and support the initiation of DNA synthesis effectively randomly throughout their DNA (Schaarschmidt et al., 2004). They are efficiently maintained in proliferating hamster and human cells without drug selection and when introduced into swine embryos can support expression of GFP in most tissues of fetal animals (Manzini et al., 2006).

C. Trans-Acting Factor

A particular example of the trans-acting factor could be Epstein Barr nuclear antigen 1 (EBNA-1), which is a DNA-binding protein that binds to FR and DS of oriP or Rep* to facilitate replication and faithful partitioning of the EBV-based vector to daughter cells independent of, but in concert with, cell chromosomes during each cell division.

The 641 amino acids (AA) of EBNA-1 have been categorized into domains associated with its varied functions by mutational and deletional analyses. Two regions, between AA40-89 and AA329-378 are capable of linking two DNA elements in cis or in trans when bound by EBNA-1, and have thus been termed Linking Region 1 and 2 (LR1, LR2) (Middleton and Sugden, 1992; Frappier and O'Donnell, 1991; Su et al., 1991; Mackey et al., 1995). Fusing these domains of EBNA-1 to GFP homes the GFP to mitotic chromosomes (Marechal et al., 1999; Kanda et al., 2001). LR1 and LR2 are functionally redundant for replication; a deletion of either one yields a derivative of EBNA-1 capable of supporting DNA replication (Mackey and Sugden, 1999; Sears et al., 2004). LR1 and LR2 are rich in arginine and glycine residues, and resemble the AT-hook motifs that bind A/T rich DNA (Aravind and Landsman, 1998), (Sears et al., 2004). An in vitro analysis of LR1 and LR2 of EBNA-1 has demonstrated their ability to bind to A/T rich DNA (Sears et al., 2004). When LR1, containing one such AT-hook, was fused to the DNA-binding and dimerization domain of EBNA-1, it was found to be sufficient for DNA replication of oriP plasmids, albeit less efficiently than the wild-type EBNA-1 (ibid).

LR1 and LR2 do differ, though. The C-terminal half of LR1 is composed of amino acids other than the repeated Arg-Gly of the N-terminal half, and is termed unique region 1 (UR1). UR1 is necessary for EBNA-1 to activate transcription efficiently from transfected and integrated reporter DNAs containing FR (Wu et al., 2002; Kennedy and Sugden, 2003; Altmann et al., 2006). UR1 is also essential for the efficient transformation of B-cells infected by EBV. When a derivative of EBNA-1 lacking this domain replaces the wild-type protein in the context of the whole virus, these derivative viruses have 0.1% of the transforming ability of the wild-type virus (Altmann et al., 2006).

LR2 is not required for EBNA-1's support of oriP replication (Shire et al., 1999; Mackey and Sugden, 1999; Sears et al., 2004). Additionally, the N-terminal half of EBNA-1 can be replaced with cellular proteins containing AT-hook motifs, such as HMGA1a, and still retain replicative function (Hung et al., 2001; Sears et al., 2003; Altmann et al., 2006). These findings indicate that it likely is the AT-hook activities of LR1 and LR2 that are required for the maintenance of oriP in human cells.

A third of EBNA-1's residues (AA91-328) consist of glycine-glycine-alanine (GGA) repeats, implicated in EBNA-1's ability to evade the host immune response by inhibiting proteosomal degradation and presentation (Levitskaya et al., 1995; Levitskaya et al., 1997). These repeats have also been found to inhibit translation of EBNA-1 in vitro and in vivo (Yin et al., 2003). However, the deletion of much of this domain has no apparent effect on functions of EBNA-1 in cell culture, making the role that this domain plays difficult to elucidate.

A nuclear localization signal (NLS) is encoded by AA379-386, which also associates with the cellular nuclear importation machinery (Kim et al., 1997; Fischer et al., 1997). Sequences within the Arg-Gly rich regions of LR1 and LR2 may also function as NLSs due to their highly basic content.

Lastly, the C-terminus (AA458-607) encodes the overlapping DNA-binding and dimerization domains of EBNA-1. The structure of these domains bound to DNA has been solved by X-ray crystallography, and was found to be similar to the DNA-binding domain of the E2 protein of papillomaviruses (Hegde et al., 1992; Kim et al., 2000; Bochkarev et al., 1996).

In specific embodiments of the invention, a reprogramming vector will contain both oriP and an abbreviated sequence encoding a version of EBNA-1 competent to support plasmid replication and its proper maintenance during cell division. The highly repetitive sequence within the amino-terminal one-third of wild-type EBNA-1 and removal of a 25 amino-acid region that has demonstrated toxicity in various cells are dispensable for EBNA-1's trans-acting function associated with oriP (Yates et al. 1985; Kennedy et al. 2003). Therefore, the abbreviated form of EBNA-1, known as deltaUR1, could be used alongside oriP within this episomal vector-based system in one embodiment.

In certain aspects, a derivative of EBNA-1 that may be used in the invention is a polypeptide which, relative to a corresponding wild-type polypeptide, has a modified amino acid sequence. The modifications include the deletion, insertion or substitution of at least one amino acid residue in a region corresponding to the unique region (residues about 65 to about 89) of LR1 (residues about 40 to about 89) in EBNA-1, and may include a deletion, insertion and/or substitution of one or more amino acid residues in regions corresponding to other residues of EBNA-1, e.g., about residue 1 to about residue 40, residues about 90 to about 328 ("Gly-Gly-Ala" repeat region), residues about 329 to about 377 (LR2), residues about 379 to about 386 (NLS), residues about 451 to about 608 (DNA binding and dimerization), or residues about 609 to about 641, so long as the resulting derivative has the desired properties, e.g., dimerizes and binds DNA containing an ori corresponding to oriP, localizes to the nucleus, is not cytotoxic, and activates transcription from an extra-chromosomal but does not substantially active transcription from an integrated template.

D. Residue-Free Feature

Importantly, the replication and maintenance of oriP-based episomal vector is imperfect and is lost precipitously (25% per cell division) from cells within the first two weeks of its being introduced into cells; however, those cells that retain the plasmid lose it less frequently (3% per cell division) (Leight and Sugden, 2001; Nanbo and Sugden, 2007). Once selection for cells harboring the plasmid is removed, plasmids will be lost during each cell division until all of them have been eliminated over time without leaving a footprint of its former existence within the resulting daughter cells. Certain aspects of the invention make use of this footprint-less feature of the oriP-based system as an alternative to the current viral-associated approach to deliver genes to generate iPS cells. Other extra-chromosomal vectors will also be lost during replication and propagation of host cells and could also be employed in the present invention.

E. Reprogramming Factors

The generation of iPS cells is crucial on the genes used for the induction. The following factors or combination thereof could be used in the vector system disclosed in the present invention. In certain aspects, nucleic acids encoding Sox and Oct (preferably Oct3/4) will be included into the reprogramming vector. For example, a reprogramming vector may comprise expression cassettes encoding Sox2, Oct4, Nanog and optionally Lin-28, or expression cassettes encoding Sox2, Oct4, Klf4 and optionally c-myc. Nucleic acids encoding these reprogramming factors may be comprised in the same expression cassette, different expression cassettes, the same reprogramming vector, or different reprogramming vectors.

Oct-3/4 and certain members of the Sox gene family (Sox1, Sox2, Sox3, and Sox15) have been identified as crucial transcriptional regulators involved in the induction process whose absence makes induction impossible. Additional genes, however, including certain members of the Klf family (KM, Klf2, Klf4, and Klf5), the Myc family (C-myc, L-myc, and N-myc), Nanog, and LIN28, have been identified to increase the induction efficiency.

Oct-3/4 (Pou5f1) is one of the family of octamer ("Oct") transcription factors, and plays a crucial role in maintaining pluripotency. The absence of Oct-3/4 in Oct-3/4+ cells, such as blastomeres and embryonic stem cells, leads to spontaneous trophoblast differentiation, and presence of Oct-3/4 thus gives rise to the pluripotency and differentiation potential of embryonic stem cells. Various other genes in the "Oct" family, including Oct-3/4's close relatives, Oct1 and Oct6, fail to elicit induction.

The Sox family of genes is associated with maintaining pluripotency similar to Oct-3/4, although it is associated with multipotent and unipotent stem cells in contrast with Oct-3/4, which is exclusively expressed in pluripotent stem cells. While Sox2 was the initial gene used for induction by Takahashi et al. (2006), Wernig et al. (2007), and Yu et al. (2007), other genes in the Sox family have been found to work as well in the induction process. Sox1 yields iPS cells with a similar efficiency as Sox2, and genes Sox3, Sox15, and Sox18 also generate iPS cells, although with decreased efficiency.

Nanog is a transcription factor critically involved with self-renewal of undifferentiated embryonic stem cells. In humans, this protein is encoded by the NANOG gene. Nanog is a gene expressed in embryonic stem cells (ESCs) and is thought to be a key factor in maintaining pluripotency. NANOG is thought to function in concert with other factors such as Oct4 (POU5F1) and Sox2 to establish ESC identity.

LIN28 is an mRNA binding protein expressed in embryonic stem cells and embryonic carcinoma cells associated with differentiation and proliferation. Yu et al. (2007) demonstrated it is a factor in iPS generation, although it is not essential.

Klf4 of the Klf family of genes was initially identified by Takahashi et al. (2006) and confirmed by Wernig et al. (2007) as a factor for the generation of mouse iPS cells and was demonstrated by Takahashi et al. (2007) as a factor for generation of human iPS cells. However, Yu et al. (2007) reported that Klf4 was not essential for generation of human iPS cells. Klf2 and Klf4 were found to be factors capable of generating iPS cells, and related genes Klf1 and Klf5 did as well, although with reduced efficiency.

The Myc family of genes are proto-oncogenes implicated in cancer. Takahashi et al. (2006) and Wernig et al. (2007) demonstrated that c-myc is a factor implicated in the generation of mouse iPS cells and Yamanaka et al. demonstrated it was a factor implicated in the generation of human iPS cells. However, Yu et al. (2007) and Takahashi et al. (2007) reported that c-myc was unnecessary for generation of human iPS cells. Usage of the "myc" family of genes in induction of iPS cells is troubling for the eventuality of iPS cells as clinical therapies, as 25% of mice transplanted with c-myc-induced iPS cells developed lethal teratomas. N-myc and L-myc have been identified to induce pluripotency instead of c-myc with similar efficiency. In certain aspects, Myc mutants, variants, homologs, or derivatives may be used, such as mutants that have reduced transformation of cells. Examples include LMYC (NM_001033081), MYC with 41 amino acids deleted at the N-terminus (dN2MYC), or MYC with mutation at amino acid position 136 (e.g., W136E).

V. Cellular Signaling Inhibitors

In certain aspects of the invention, during at least part of the reprogramming process, the cell may be maintained in the presence of one or more signaling inhibitors which inhibit a signal transducer involved in a signaling cascade, e.g., in the presence of a MEK inhibitor, a GSK3 inhibitor, a TGF-β receptor inhibitor, both a MEK inhibitor and a GSK3 inhibitor, both a GSK3 inhibitor and a TGF-β receptor inhibitor, both a MEK inhibitor and a TGF-β receptor inhibitor, a combination of all three inhibitors, or inhibitor of other signal transducers within these same pathways. In certain aspects, ROCK inhibitors, such as HA-100, or Myosin II inhibitor, such as blebbistatin, may be used to facilitate clonal expansion of reprogrammed cells and resulting iPS cells. High concentration of FGF, in combination with specific reprogramming medium such as conditioned human ES cell culture medium or a chemically defined medium such as serum-free defined N2B27 medium, may also be used to increase reprogramming efficiency.

In certain embodiments, in addition to introducing the cells with one or more reprogramming factors (e.g. two, three or more, as described herein) by extra-chromosome genetic elements, the cells are treated with a reprogramming medium comprising: a MEK inhibitor, a TGF-β receptor inhibitor, a GSK3 inhibitor, and optionally LIF, with the advantages such as improving reprogramming efficiency and kinetics and facilitating iPS cell identification in the primary reprogramming culture, thus preserving iPS cell clonality.

It will be understood that in these aspects and embodiments, other signaling inhibitors which inhibit a signaling component of the same signaling pathway (e.g. ERK1 or ERK2 cascade) may be substituted where desired for the MEK inhibitor. This may include inhibition of an upstream stimulus of the MAPK pathway, in particular through the FGF receptor (Ying, 2008). Likewise, the GSK3 inhibitor may be substituted where desired for other inhibitors of GSK3-related signaling pathways, such as insulin synthesis and Wnt/β-catenin signaling; the LIF may be substituted where desired for other activators of Stat3 or gp130 signaling.

Such a signaling inhibitor, e.g., a MEK inhibitor, a GSK3 inhibitor, a TGF-β receptor inhibitor, may be used at an effective concentration of at least or about 0.02, 0.05, 0.1, 0.2, 0.5, 1, 2, 3, 4, 5, 10, 15, 20, 25, 30, 35, 40, 45, 50, 100, 150, 200, 500 to about 1000 µM, or any range derivable therein.

Inhibitors may be provided or obtained by those skilled in the art by conventional means or from conventional sources (see also WO2007113505).

A. Glycogen Synthase Kinase 3 Inhibitor

Glycogen synthase kinase 3 (GSK-3) is a serine/threonine protein kinase that mediates the addition of phosphate molecules on certain serine and threonine amino acids in particular cellular substrates. The phosphorylation of these other proteins by GSK-3 usually inhibits the target protein (also called the "substrate"). As mentioned, GSK-3 is known for phosphorylating and thus inactivating glycogen synthase. It has also been implicated in the control of cellular response to damaged DNA and Wnt signaling. GSK-3 also phosphorylates Ci in the Hedgehog (Hh) pathway, targeting it for proteolysis to an inactive form. In addition to glycogen synthase, GSK-3 has many other substrates. However, GSK-3 is unusual among the kinases in that it usually requires a "priming kinase" to first phosphorylate a substrate.

The consequence of GSK-3 phosphorylation is usually inhibition of the substrate. For example, when GSK-3 phosphorylates another of its substrates, the NFAT family of transcription factors, these transcription factors can not translocate to the nucleus and are therefore inhibited. In addition to its important role in the Wnt signaling pathway, which is required for establishing tissue patterning during development, GSK-3 is also critical for the protein synthesis that is induced in settings such as skeletal muscle hypertrophy. Its roles as an NFAT kinase also places it as a key regulator of both differentiation and cellular proliferation.

GSK3 inhibition may refer to inhibition of one or more GSK3 enzymes. The family of GSK3 enzymes is well-known and a number of variants have been described (see e.g. Schaffer et al., 2003). In specific embodiments GSK3-β is inhibited. GSK3-α inhibitors are also suitable, and in certain aspects inhibitors for use in the invention inhibit both GSK3-α and GSK3-β.

Inhibitors of GSK3 can include antibodies that bind, dominant negative variants of, and siRNA and antisense nucleic acids that target GSK3. Examples of GSK3 inhibitors are described in Bennett et al. (2002) and in Ring et al. (2003).

Specific examples of GSK3 inhibitors include, but are not limited to, Kenpaullone, 1-Azakenpaullone, CHIR99021, CHIR98014, AR-A014418 (see, e.g., Gould et al., 2004), CT 99021 (see, e.g., Wagman, 2004), CT 20026 (see, Wagman, supra), SB415286, SB216763 (see, e.g., Martin et al., 2005), AR-A014418 (see, e.g., Noble et al., 2005), lithium (see, e.g., Gould et al., 2003), SB 415286 (see, e.g., Frame et al., 2001) and TDZD-8 (see, e.g., Chin et al., 2005). Further exemplary GSK3 inhibitors available from Calbiochem (see, e.g., Dalton et al., WO2008/094597, herein incorporated by reference), include but are not limited to BIO (2'Z,3'£)-6-Bromomdirubm-3'-oxime (GSK3 Inhibitor IX); BIO-Acetoxime (2'Z, 3'E)-6-Bromoindirubin-3'-acetoxime (GSK3 Inhibitor X); (5-Methyl-1H-pyrazol-3-yl)-(2-phenylquinazolin-4-yl) amine (GSK3-Inhibitor XIII); Pyridocarbazole-cyclopenadienylruthenium complex (GSK3 Inhibitor XV); TDZD-8 4-Benzyl-2-methyl-1,2,4-thiadiazolidine-3,5-dione (GSK3beta Inhibitor I); 2-Thio(3-iodobenzyl)-5-(1-pyridyl)-[1,3,4]-oxadiazole (GSK3beta Inhibitor II); OTDZT 2,4-Dibenzyl-5-oxothiadiazolidine-3-thione (GSK3beta Inhibitor III); alpha-4-Dibromoacetophenone (GSK3beta Inhibitor VII); AR-AO 14418 N-(4-Methoxybenzyl)-N'-(5-nitro-1,3-thiazol-2-yl)urea (GSK-3beta Inhibitor VIII); 3-(1-(3-Hydroxypropyl)-1H-pyrrolo[2,3-b]pyridin-3-yl]-4-pyrazin-2-yl-pyrrole-2,5-dione (GSK-3beta Inhibitor XI); TWS1 19 pyrrolopyrimidine compound (GSK3beta Inhibitor XII); L803 H-KEAPP APPQSpP-NH2 or its Myristoylated form (GSK3beta Inhibitor XIII); 2-Chloro-1-(4,5-dibromothiophen-2-yl)-ethanone (GSK3beta Inhibitor VI); AR-AO144-18; SB216763; and SB415286.

GSK3 inhibitors can activate, for example, the Wnt/β-catenin pathway. Many of β-catenin downstream genes co-regulate pluripotency gene networks. For example, a GSK inhibitor activates cMyc expression as well as enhances its protein stability and transcriptional activity. Thus, in some embodiments, GSK3 inhibitors can be used to stimulate endogenous Myc polypeptide expression in a cell, thereby eliminating the need for Myc expression to induce pluripotency.

In addition, the structure of the active site of GSK3-β has been characterized and key residues that interact with specific and non-specific inhibitors have been identified (Bertrand et al., 2003). This structural characterization allows additional GSK inhibitors to be readily identified.

The inhibitors used herein are preferably specific for the kinase to be targeted. The inhibitors of certain embodiments are specific for GSK3-β and GSK3-α, substantially do not inhibit erk2 and substantially do not inhibit cdc2. Preferably the inhibitors have at least 100 fold, more preferably at least 200 fold, very preferably at least 400 fold selectivity for human GSK3 over mouse erk2 and/or human cdc2, measured as ratio of $IC_{50}$ values; here, reference to GSK3 $IC_{50}$ values refers to the mean values for human GSK3-β and GSK3-α.

Good results have been obtained with CHIR99021 which is specific for GSK3. Suitable concentrations for use of CHIR99021 are in the range 0.01 to 100, preferably 0.1 to 20, more preferably 0.3 to 10 micromolar.

B. MEK Inhibitor

MEK inhibitors, which include inhibitors of mitogen-activated protein kinase kinase (MAPK/ERK kinase or MEK) or its related signaling pathways like MAPK cascade, may be used in certain aspects of the invention. Mitogen-activated protein kinase kinase (sic) is a kinase enzyme which phosphorylates mitogen-activated protein kinase. It is also known as MAP2K. Extracellular stimuli lead to activation of a MAP kinase via a signaling cascade ("MAPK cascade") composed of MAP kinase, MAP kinase kinase (MEK, MKK, MEKK, or MAP2K), and MAP kinase kinase kinase (MKKK or MAP3K).

A MEK inhibitor herein refers to MEK inhibitors in general. Thus, a MEK inhibitor refers to any inhibitor of a member of the MEK family of protein kinases, including MEK1, MEK2 and MEK5. Reference is also made to MEK1, MEK2 and MEK5 inhibitors. Examples of suitable MEK inhibitors, already known in the art, include the MEK1 inhibitors PD184352 and PD98059, inhibitors of MEK1 and MEK2 U0126 and SL327, and those discussed in Davies et al. (2000).

In particular, PD184352 and PD0325901 have been found to have a high degree of specificity and potency when compared to other known MEK inhibitors (Bain et al., 2007). Other MEK inhibitors and classes of MEK inhibitors are described in Zhang et al. (2000).

Inhibitors of MEK can include antibodies to, dominant negative variants of, and siRNA and antisense nucleic acids that suppress expression of MEK. Specific examples of MEK inhibitors include, but are not limited to, PD0325901 (see, e.g., Rinehart et al., 2004), PD98059 (available, e.g., from Cell Signaling Technology), U0126 (available, for example, from Cell Signaling Technology), SL327 (available, e.g., from Sigma-Aldrich), ARRY-162 (available, e.g., from Array Biopharma), PD184161 (see, e.g., Klein et al., 2006), PD184352 (CI-1040) (see, e.g., Mattingly et al., 2006), sunitinib (see, e.g., Voss, et al., US2008004287 incorporated herein by reference), sorafenib (see, Voss supra), Vandetanib (see, Voss supra), pazopanib (see, e.g., Voss supra), Axitinib (see, Voss supra) and PTK787 (see, Voss supra).

Currently, several MEK inhibitors are undergoing clinical trial evaluations. CI-1040 has been evaluate in Phase I and II clinical trials for cancer (see, e.g., Rinehart et al., 2004). Other MEK inhibitors being evaluated in clinical trials include PD184352 (see, e.g., English et al., 2002), BAY 43-9006 (see, e.g., Chow et al., 2001), PD-325901 (also PD0325901), GSK1 120212, ARRY-438162, RDEA1 19, AZD6244 (also ARRY-142886 or ARRY-886), R05126766, XL518 and AZD8330 (also ARRY-704).

Inhibition of MEKs can also be conveniently achieved using RNA-mediated interference (RNAi). Typically, a double-stranded RNA molecule complementary to all or part of a MEK gene is introduced into pluripotent cells, thus promoting specific degradation of MEK-encoding mRNA molecules. This post-transcriptional mechanism results in reduced or abolished expression of the targeted MEK gene. Suitable techniques and protocols for achieving MEK inhibition using RNAi are known.

A number of assays for identifying kinase inhibitors, including GSK3 inhibitors and MEK inhibitors, are known. For example, Davies et al. (2000) describes kinase assays in which a kinase is incubated in the presence of a peptide substrate and radiolabeled ATP. Phosphorylation of the substrate by the kinase results in incorporation of the label into the substrate. Aliquots of each reaction are immobilized on phosphocellulose paper and washed in phosphoric acid to remove free ATP. The activity of the substrate following incubation is then measured and provides an indication of kinase activity. The relative kinase activity in the presence and absence of candidate kinase inhibitors can be readily determined using such an assay. Downey et al. (1996) also describes assays for kinase activity which can be used to identify kinase inhibitors.

C. TGF-β Receptor Inhibitor

TGF-β receptor inhibitors may include any inhibitors of TGF signaling in general or inhibitors specific for TGF-β receptor (e.g., ALK5) inhibitors, which can include antibodies to, dominant negative variants of, and siRNA and antisense nucleic acids that suppress expression of, TGF beta receptors (e.g., ALK5). Exemplary TGFβ receptor/ALK5 inhibitors include, but are not limited to, SB431542 (see, e.g., Inman et al., 2002), A-83-01, also known as 3-(6-Methyl-2-pyridinyl)-N-phenyl-4-(4-quinolinyl)-1H-pyrazole-1-carbothioamide (see, e.g., Tojo et al., 2005, and commercially available from, e.g., Toicris Bioscience); 2-(3-(6-Methylpyridin-2-yl)-1H-pyrazol-4-yl)-1, 5-naphthyridine, Wnt3a/BIO (see, e.g., Dalton, et al., WO2008/094597, herein incorporated by reference), BMP4 (see, Dalton, supra), GW788388 (-(4-[3-(pyridin-2-yl)-1H-pyrazol-4-yl]pyridm-2-yl}-N-(tetrahydro-2H-pyran-4-yl)benzamide) (see, e.g., Gellibert et al., 2006), SM16 (see, e.g., Suzuki et al., 2007), IN-1130 (3-((5-(6-methylpyridin-2-yl)-4-(quinoxalin-6-yl)-1H-imidazol-2-yl)methyl)benzamide) (see, e.g., Kim et al., 2008), GW6604 (2-phenyl-4-(3-pyridin-2-yl-1H-pyrazol-4-yl)pyridine) (.see, e.g., de Gouville et al., 2006), SB-505124 (2-(5-benzo[1,3]dioxol-5-yl-2-tert-butyl-3H-imidazol-4-yl)-6-methylpyridine hydrochloride) (see, e.g., DaCosta et al., 2004) and pyrimidine derivatives (see, e.g., those listed in Stiefl et al., WO2008/006583, herein incorporated by reference).

Further, while an "ALK5 inhibitor" is not intended to encompass non-specific kinase inhibitors, an "ALK5 inhibitor" should be understood to encompass inhibitors that inhibit ALK4 and/or ALK7 in addition to ALK5, such as, for example, SB-431542 (see, e.g., Inman et al., 2002). Without intending to limit the scope of the invention, it is believed that ALK5 inhibitors affect the mesenchymal to epithelial conversion/transition (MET) process. TGFβ/activin pathway is a driver for epithelial to mesenchymal transition (EMT). The inventors contemplate that inhibiting the TGFβ/activin pathway can facilitate MET (i.e., reprogramming) process.

It is believed that inhibition of the TGFβ/activin pathway will have similar effects. Thus, any inhibitor (e.g., upstream or downstream) of the TGFβ/activin pathway can be used in combination with, or instead of, TGF-β/ALK5 inhibitors as described herein. Exemplary TGFβ/activin pathway inhibitors include but are not limited to: TGF beta receptor inhibitors, inhibitors of SMAD 2/3 phosphorylation, inhibitors of the interaction of SMAD 2/3 and SMAD 4, and activators/agonists of SMAD 6 and SMAD 7. Furthermore, the categorizations described herein are merely for organizational purposes and one of skill in the art would know that compounds can affect one or more points within a pathway, and thus compounds may function in more than one of the defined categories.

TGF beta receptor inhibitors can include antibodies to, dominant negative variants of, and siRNA or antisense nucleic acids that target TGF beta receptors. Specific examples of inhibitors include but are not limited to SU5416; 2-(5-benzo[1,3]dioxol-5-yl-2-tert-butyl-3H-imidazol-4-yl)-6-methylpyridine hydrochloride (SB-505124); lerdelimumb (CAT-152); metelimumab (CAT-192); GC-1008; ID1 1; AP-12009; AP-11014; LY550410; LY580276; LY364947; LY2109761; SB-505124; SB-431542; SD-208; SM16; NPC-30345; Ki26894; SB-203580; SD-093; Gleevec; 3,5,7,2',4'-pentahydroxyfiavone (Morin); activin-M108A; P144; soluble TBR2-Fc; and antisense transfected tumor cells that target TGF beta receptors (See, e.g., Wrzesinski et al., 2007; Kaminska et al., 2005; and Chang et al., 2007.)

D. ROCK Inhibitors and Myosin II ATPase Inhibitors

Pluripotent stem cells, especially human ES cells and iPS cells, are vulnerable to apoptosis upon cellular detachment and dissociation, which are important for clonal isolation or expansion and differentiation induction. Recently, a small class of molecules have been found to increase clonal efficiency and survival of dissociated pluripotent stem cells, such as Rho-associated kinase (ROCK) inhibitors, which are inhibitors for ROCK-related signaling pathways, for example, Rho-specific inhibitors, ROCK-specific inhibitors or myosin II-specific inhibitors. In certain aspects of the invention, ROCK inhibitors may be used for culturing and passaging of pluripotent stem cells and/or differentiation of the stem cells. Therefore, ROCK inhibitors could be present in any cell culture medium in which pluripotent stem cells grow, dissociate, form aggregates, or undergo differentiation, such as an adherent culture or suspension culture. Unless otherwise stated herein, myosin II inhibitors, such as blebbistatin, can substitute for the experimental use of ROCK inhibitors.

ROCK signaling pathways may include Rho family GTPases; ROCK, a major effector kinase downstream of Rho; Myosin II, the predominant effector downstream of ROCK (Harb et al., 2008); and any intermediate, upstream, or downstream signal processors. ROCK may phosphorylate and inactivate myosin phosphatase target subunit 1 (MYPT1), one of the major downstream targets of ROCK that negatively regulates myosin function through dephosphorylation of myosin regulatory light chain (MRLC).

ROCKs are serine/threonine kinases that serve as a target proteins for Rho (of which three isoforms exist—RhoA, RhoB and RhoC). Theses kinases were initially characterized as mediators of the formation of RhoA-induced stress fibers and focal adhesions. The two ROCK isoforms—ROCK1 (p160ROCK, also called ROKβ) and ROCK2 (ROKα)—are comprised of a N-terminal kinase domain, followed by a coiled-coil domain containing a Rho-binding domain and a pleckstrin-homology domain (PH). Both ROCKs are cytoskeletal regulators, mediating RhoA effects on stress fiber formation, smooth muscle contraction, cell adhesion, membrane ruffling and cell motility. ROCKs may exert their biological activity by targeting downstream molecules, such as myosin II, myosin light chain (MLC), MLC phosphatase (MLCP) and the phosphatase and tensin homolog (PTEN).

Non-limiting examples of ROCK inhibitors include HA-100, Y-27632, H-1152, Fasudil (also referred to as HA1077), Y-30141 (described in U.S. Pat. No. 5,478,838), Wf-536, HA-1077, hydroxyl-HA-1077, GSK269962A, SB-772077-B, and derivatives thereof, and antisense nucleic acid for ROCK, RNA interference inducing nucleic acid (for example, siRNA), competitive peptides, antagonist peptides, inhibitory antibodies, antibody-ScFV fragments, dominant negative variants and expression vectors thereof. Further, since other low molecular compounds are known as ROCK inhibitors, such compounds or derivatives thereof can be also used in embodiments (for example, refer to U.S. Patent Publication Nos. 20050209261, 20050192304, 20040014755, 20040002508, 20040002507, 20030125344 and 20030087919, and International Patent Publication Nos.

2003/062227, 2003/059913, 2003/062225, 2002/076976 and 2004/039796, which are hereby incorporated by reference). In certain aspects of the present invention, a combination of one or two or more of the ROCK inhibitors can also be used.

Rho-specific inhibitors, such as *Clostridium botulinum* C3 exoenzyme, and/or Myosin II-specific inhibitors may also be used as a ROCK inhibitor in certain aspects of the invention.

VI. Culturing of Reprogrammed Cells

The starting cell and the end, reprogrammed cell generally have differing requirements for culture medium and conditions. To allow for this while also allowing that reprogramming of the cell is taking place, it is usual to carry out at least an initial stage of culture, after introduction of the reprogramming factors, in the presence of medium and under culture conditions known to be suitable for growth of the starting cell. This is followed by a subsequent period of culture in the presence of a reprogramming medium and under conditions known to be suitable for pluripotent cells—on feeders with serum or use chemically-defined medium or feeder-free conditions. Suitable feeders include primary or immortalized fibroblast lines, typically inactivated so they do not overgrow the growth of the cells being reprogrammed. After a sufficient time for reprogramming, the reprogrammed cells may be further cultured for expansion of iPS cells either before or after selection of iPS cells in an expansion medium. Such an expansion medium may comprise one or more signaling inhibitors as described above or comprise a culture medium essentially free of these inhibitors.

The initial stage of culture is preferably for a period of up to 6 days, more preferably up to 4 days and in particular embodiments, described below for not more than 3 days, and more particularly up to or about one day. The subsequent stage of culture in reprogramming medium comprising one or more signaling inhibitors is suitably for a period of at least or about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33 days, or any range derivable therein, and can be for a period of up to 70 days, preferably up to 56 days, or until detection of iPS cells. In a specific embodiment described below used to generate reprogrammed human cells, the initial stage of culture was for a period of about 1 day and the subsequent stage was for about 9 to 28 days by culture in a reprogramming condition the presence of a reprogramming medium comprising a MEK inhibitor, a TGF-β receptor inhibitor, and a GSK3 inhibitor. The reprogramming condition may be essentially free of feeder cells. In further aspects, the reprogramming medium may be chemically defined. To improve reprogramming, the reprogramming medium may further comprise high concentration of FGF and may be essentially free of TGFβ.

The combination of a MEK inhibitor, a TGF-β receptor inhibitor, and a GSK3 inhibitor may facilitate reprogramming process, including increasing reprogramming efficiency and shortening reprogramming time. LIF is an example of an activator of gp130 signaling, another being IL-6 in combination with soluble IL-6 receptor, and promotes growth and survival of the cell as it is in the process of being reprogrammed. During reprogramming, cells may be cultured in the presence of LIF; using LIF may help reprogrammed cells in certain aspects of the present invention to improve cell survival and clonogenicity.

A. Stem Cell Culture Conditions in General

The culturing conditions according to the present invention will be appropriately defined depending on the medium and stem cells used. The medium according to certain aspects of the present invention can be prepared using a medium used for culturing animal cells as its basal medium, such as any of TeSR, BME, BGJb, CMRL 1066, Glasgow MEM, Improved MEM Zinc Option, IMDM, Medium 199, Eagle MEM, αMEM, DMEM, Ham, RPMI 1640, and Fischer's media, as well as any combinations thereof, but the medium is not particularly limited thereto as far as it can be used for culturing animal cells.

The medium according to the present invention can be a serum-containing or serum-free medium. The serum-free medium refers to media with no unprocessed or unpurified serum, and accordingly can include media with purified blood-derived components or animal tissue-derived components (such as growth factors). From the aspect of preventing contamination with heterogeneous animal-derived components, serum can be derived from the same animal as that of the stem cell(s).

The medium according to the present invention may contain or may not contain any alternatives to serum. The alternatives to serum can include materials which appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3'-thiolgiycerol, or equivalents thereto. The alternatives to serum can be prepared by the method disclosed in International Publication No. 98/30679, for example. Alternatively, any commercially available materials can be used for more convenience. The commercially available materials include knockout Serum Replacement (KSR), Chemically-defined Lipid concentrated (Gibco), and Glutamax (Gibco).

The medium of the present invention can also contain fatty acids or lipids, amino acids (such as non-essential amino acids), vitamin(s), growth factors, cytokines, antioxidant substances, 2-mercaptoethanol, pyruvic acid, buffering agents, and inorganic salts. The concentration of 2-mercaptoethanol can be, for example, about 0.05 to 1.0 mM, and particularly about 0.1 to 0.5 mM, but the concentration is particularly not limited thereto as long as it is appropriate for culturing the stem cell(s).

A culture vessel used for culturing the stem cell(s) can include, but is particularly not limited to: flask, flask for tissue culture, dish, petri dish, dish for tissue culture, multi dish, micro plate, micro-well plate, multi plate, multi-well plate, micro slide, chamber slide, tube, tray, Cell STACK® Chambers, culture bag, and roller bottle, as long as it is capable of culturing the stem cells therein. The stem cells may be cultured in a volume of at least or about 0.2, 0.5, 1, 2, 5, 10, 20, 30, 40, 50 ml, 100 ml, 150 ml, 200 ml, 250 ml, 300 ml, 350 ml, 400 ml, 450 ml, 500 ml, 550 ml, 600 ml, 800 ml, 1000 ml, 1500 ml, or any range derivable therein, depending on the needs of the culture. In a certain embodiment, the culture vessel may be a bioreactor, which may refer to any device or system that supports a biologically active environment. The bioreactor may have a volume of at least or about 2, 4, 5, 6, 8, 10, 15, 20, 25, 50, 75, 100, 150, 200, 500 liters, 1, 2, 4, 6, 8, 10, 15 cubic meters, or any range derivable therein.

The culture vessel can be cellular adhesive or non-adhesive and selected depending on the purpose. The cellular adhesive culture vessel can be coated with any of substrates for cell adhesion such as extracellular matrix (ECM) to improve the adhesiveness of the vessel surface to the cells. The substrate for cell adhesion can be any material intended to attach stem cells or feeder cells (if used). The substrate for cell adhesion includes collagen, gelatin, poly-L-lysine, poly-D-lysine, vitronectin, laminin, and fibronectin and mixtures thereof for example Matrigel™, and lysed cell membrane preparations (Klimanskaya et al., 2005).

Other culturing conditions can be appropriately defined. For example, the culturing temperature can be about 30 to 40° C., for example, at least or about 31, 32, 33, 34, 35, 36, 37, 38, 39° C. but particularly not limited to them. The $CO_2$ concentration can be about 1 to 10%, for example, about 2 to 5%, or any range derivable therein. The oxygen tension can be at least or about 1, 5, 8, 10, 20%, or any range derivable therein.

The methods of the present invention in certain aspects can be used for adhesion culture of stem cells, for example. In this case, the cells can be cultured in the presence of feeder cells. In the case where the feeder cells are used in the methods of the present invention, stromal cells such as fetal fibroblasts can be used as feeder cells (for example, refer to; Hogan et al., Manipulating the Mouse Embryo, A Laboratory Manual (1994); Gene Targeting, A Practical Approach (1993); Martin (1981); Evans and Kaufman (1981); Jainchill et al., (1969); Nakano et al. (1996); Kodama et al. (1982); and International Publication Nos. 01/088100 and 2005/080554).

The methods of the present invention in certain aspects can be also used for a suspension culture of stem cells, including suspension culture on carriers (Fernandes et al., 2004) or gel/biopolymer encapsulation (United States Publication 2007/0116680). The term suspension culture of the stem cells means that the stem cells are cultured under non-adherent condition with respect to the culture vessel or feeder cells (if used) in a medium. The suspension culture of stem cells includes a dissociation culture of stem cells and an aggregate suspension culture of stem cells. The term dissociation culture of stem cells means that suspended stem cells is cultured, and the dissociation culture of stem cells include those of single stem cell or those of small cell aggregates composed of a plurality of stem cells (for example, about 2 to 400 cells). When the aforementioned dissociation culture is continued, the cultured, dissociated cells form a larger aggregate of stem cells, and thereafter an aggregate suspension culture can be performed. The aggregate suspension culture includes an embryoid culture method (see Keller et al., 1995), and a SFEB method (Watanabe et al., 2005; International Publication No. 2005/123902).

B. Culturing of Pluripotent Stem Cells

Depending on culture conditions, pluripotent stem cells can produce colonies of differentiated cells or undifferentiated cells. The term "differentiate" means the progression of a cell down a developmental pathway. The term "differentiated" is a relative term describing a cell's progression down a developmental pathway in comparison with another cell. For example, a pluripotent cell can give rise to any cell of the body, while a more differentiated cell such as a hematopoetic cell will give rise to fewer cell types.

Cultures of pluripotent stem cells are described as "undifferentiated" when a substantial proportion of stem cells and their derivatives in the population display morphological characteristics of undifferentiated cells, clearly distinguishing them from differentiated cells of embryo or adult origin. Undifferentiated ES or iPS cells are recognized by those skilled in the art, and typically appear in the two dimensions of a microscopic view in colonies of cells with high nuclear/cytoplasmic ratios and prominent nucleoli. It is understood that colonies of undifferentiated cells can have neighboring cells that are differentiated.

ES cells can be maintained in an undifferentiated state by culturing the cells in the presence of serum and a feeder layer, typically mouse embryonic fibroblasts. Other methods for maintaining stem cells in an undifferentiated state are also known. For example, mouse ES cells can be maintained in an undifferentiated state by culturing in the presence of LIF without a feeder layer. However, unlike mouse ES cells, pre-existing human ES cells do not respond to LIF. Human ES cells can be maintained in an undifferentiated state by culturing ES cells on a feeder layer of fibroblasts in the presence of basic fibroblast growth factor (Amit et al., 2000), or by culturing on a protein matrix, such as Matrigel™ or laminin, without a feeder layer and in the presence of fibroblast-conditioned medium plus basic fibroblast growth factor (Xu et al., 2001; U.S. Pat. No. 6,833,269).

Methods for preparing and culturing ES cells can be found in standard textbooks and reviews in cell biology, tissue culture, and embryology, including teratocarcinomas and embryonic stem cells: A practical approach (1987); Guide to Techniques in Mouse Development (1993); Embryonic Stem Cell Differentiation in vitro (1993); Properties and uses of Embryonic Stem Cells: Prospects for Application to Human Biology and Gene Therapy (1998), all incorporated herein by reference. Standard methods used in tissue culture generally are described in Animal Cell Culture (1987); Gene Transfer Vectors for Mammalian Cells (1987); and Current Protocols in Molecular Biology and Short Protocols in Molecular Biology (1987 & 1995).

After somatic cells are introduced or contacted with reprogramming factors, these cells may be cultured in a medium sufficient to maintain the pluripotency and the undifferentiated state. Culturing of induced pluripotent stem (iPS) cells generated in this invention can use various medium and techniques developed to culture primate pluripotent stem cells, more specially, embryonic stem cells, as described in U.S. Pat. Publication 20070238170 and U.S. Pat. Publication 20030211603, and U.S. Pat. Publication 20080171385, which are hereby incorporated by reference. It is appreciated that additional methods for the culture and maintenance of pluripotent stem cells, as would be known to one of skill, may be used with the present invention.

In certain embodiments, undefined conditions may be used; for example, pluripotent cells may be cultured on fibroblast feeder cells or a medium that has been exposed to fibroblast feeder cells in order to maintain the stem cells in an undifferentiated state.

Alternately, pluripotent cells may be cultured and maintained in an essentially undifferentiated state using defined, feeder-independent culture system, such as a TeSR medium (Ludwig et al., 2006a; Ludwig et al., 2006b). Feeder-independent culture systems and media may be used to culture and maintain pluripotent cells. These approaches allow derived human iPS cells as well as human embryonic stem cells to remain in an essentially undifferentiated state without the need for mouse fibroblast "feeder layers." As described herein, various modifications may be made to these methods in order to reduce costs as desired.

Various matrix components may be used in culturing and maintaining human pluripotent stem cells. For example, Matrigel™, collagen IV, fibronectin, laminin, and vitronectin in combination may be used to coat a culturing surface as a means of providing a solid support for pluripotent cell growth, as described in Ludwig et al. (2006a; 2006b), which are incorporated by reference in their entirety. Particularly, Matrigel™ may be used to provide a substrate for cell culture and maintenance of human pluripotent stem cells. Matrigel™ is a gelatinous protein mixture secreted by mouse tumor cells and is commercially available from BD Biosciences (New Jersey, USA). This mixture resembles the complex extracellular environment found in many tissues and is used by cell biologists as a substrate for cell culture.

C. Cell Passaging

Certain aspects of the present invention can further involve a step of dissociating stem cells. Stem cell dissociation can be performed using any known procedures. These procedures include treatments with a chelating agent (such as EDTA), an enzyme (such as trypsin, collagenase), or the like, and operations such as mechanical dissociation (such as pipetting). The stem cell(s) can be treated with the ROCK inhibitor before and/or after dissociation. For example, the stem cell(s) can be treated only after dissociation.

In some further embodiments of pluripotent stem cell culturing, once a culture container is full, the colony may be split into aggregated cells or even single cells by any method suitable for dissociation, which cell are then placed into new culture containers for passaging. Cell passaging is a technique that enables to keep cells alive and growing under cultured conditions for extended periods of time. Cells usually would be passed when they are about 70%-100% confluent.

Single-cell dissociation of pluripotent stem cells followed by single cell passaging may be used in the present methods with several advantages, like facilitating cell expansion, cell sorting, and defined seeding for differentiation and enabling automatization of culture procedures and clonal expansion. For example, progeny cell clonally derivable from a single cell may be homogenous in genetic structure and/or synchronized in cell cycle, which may increase targeted differentiation. Exemplary methods for single cell passaging may be as described in U.S. Pat. App. 20080171385, which is incorporated herein by reference.

In certain embodiments, pluripotent stem cells may be dissociated into single individual cells, or a combination of single individual cells and small cell clusters comprising 2, 3, 4, 5, 6, 7, 8, 9, 10 cells or more. The dissociation may be achieved by mechanical force, or by a cell dissociation agent, such as NaCitrate, or an enzyme, for example, trypsin, trypsin-EDTA, TrypLE Select, or the like.

Based on the source of pluripotent stem cells and the need for expansion, the dissociated cells may be transferred individually or in small clusters to new culture containers in a splitting ratio such as at least or about 1:2, 1:4, 1:5, 1:6, 1:8, 1:10, 1:20, 1:40, 1:50, 1:100, 1:150, 1:200, or any range derivable therein. Suspension cell line split ratios may be done on volume of culture cell suspension. The passage interval may be at least or about every 1, 2, 3, 4, 5, 6, 7, 8, 9, 10, 11, 12, 13, 14, 15, 16, 17, 18, 19, 20 days or any range derivable therein. For example, the achievable split ratios for the different enzymatic passaging protocols may be 1:2 every 3-7 days, 1:3 every 4-7 days, and 1:5 to 1:10 approximately every 7 days, 1:50 to 1:100 every 7 days. When high split ratios are used, the passage interval may be extended to at least 12-14 days or any time period without cell loss due to excessive spontaneous differentiation or cell death.

In certain aspects, single cell passaging may be in the presence of a small molecule effective for increasing cloning efficiency and cell survival, such as a ROCK inhibitor as described above. Such a ROCK inhibitor, e.g., Y-27632, HA-1077, H-1152, or blebbistatin, may be used at an effective concentration, for example, at least or about 0.02, 0.05, 0.1, 0.2, 0.5, 1, 2, 3, 4, 5, 10, 15, 20, 25, 30, 35, 40, 45, 50 to about 100 µM, or any range derivable therein.

VII. Selection of iPS Cells

In certain aspects of the invention, after one or more extrachromosomal genetic elements are introduced into somatic cells, cells may be cultured for expansion (optionally selected for the presence of vector elements like positive selection or screenable marker to concentrate transfected cells) and these genetic elements will express reprogramming factors in these cells and replicate and partition along with cell division. These expressed reprogramming factors will reprogram somatic cell genome to establish a self-sustaining pluripotent state, and in the meantime or after removal of positive selection of the presence of vectors, exogenous genetic elements will be lost gradually. These induced pluripotent stem cells could be selected from progeny derived from these somatic cells based on embryonic stem cell characteristics because they are expected to be substantially identical to pluripotent embryonic stem cells. An additional negative selection step could be also employed to accelerate or help selection of iPS cells essentially free of exogenous genetic elements by testing the absence of reprogramming vector DNA or using selection markers.

A. Selection for Embryonic Stem Cell Characteristics

The successfully generated iPSCs from previous studies were remarkably similar to naturally-isolated pluripotent stem cells (such as mouse and human embryonic stem cells, mESCs and hESCs, respectively) in the following respects, thus confirming the identity, authenticity, and pluripotency of iPSCs to naturally-isolated pluripotent stem cells. Thus, induced pluripotent stem cells generated from the methods disclosed in this invention could be selected based on one or more of following embryonic stem cell characteristics.

i. Cellular Biological Properties

Morphology: iPSCs are morphologically similar to ESCs. Each cell may have round shape, large nucleolus and scant cytoplasm. Colonies of iPSCs could be also similar to that of ESCs. Human iPSCs form sharp-edged, flat, tightly-packed colonies similar to hESCs and mouse iPSCs form the colonies similar to mESCs, less flatter and more aggregated colonies than that of hESCs. In certain embodiments, the present method may generate large human iPS cells, which may have a diameter of at least or about 1.5, 1.6, 1.7, 1.8, 1.9, 2.0, 2.1, 2.2, 2.3, 2.4, 2.5 mm, or any range derivable therein, and be easily discernable from non-iPS cells.

Growth properties: Doubling time and mitotic activity are cornerstones of ESCs, as stem cells must self-renew as part of their definition. iPSCs could be mitotically active, actively self-renewing, proliferating, and dividing at a rate equal to ESCs.

Stem Cell Markers: iPSCs may express cell surface antigenic markers expressed on ESCs. Human iPSCs expressed the markers specific to hESC, including, but not limited to, SSEA-3, SSEA-4, TRA-1-60, TRA-1-81, TRA-2-49/6E, and Nanog. Mouse iPSCs expressed SSEA-1 but not SSEA-3 nor SSEA-4, similarly to mESCs.

Stem Cell Genes: iPSCs may express genes expressed in undifferentiated ESCs, including Oct-3/4, Sox2, Nanog, GDF3, REX1, FGF4, ESG1, DPPA2, DPPA4, and hTERT.

Telomerase Activity: Telomerases are necessary to sustain cell division unrestricted by the Hayflick limit of ~50 cell divisions. Human ESCs express high telomerase activity to sustain self-renewal and proliferation, and iPSCs also demonstrate high telomerase activity and express hTERT (human telomerase reverse transcriptase), a necessary component in the telomerase protein complex.

Pluripotency: iPSCs will be capable of differentiation in a fashion similar to ESCs into fully differentiated tissues.

Neural Differentiation: iPSCs could be differentiated into neurons, expressing βIII-tubulin, tyrosine hydroxylase, AADC, DAT, ChAT, LMX1B, and MAP2. The presence of catecholamine-associated enzymes may indicate that iPSCs, like hESCs, may be differentiable into dopaminergic neurons. Stem cell-associated genes will be downregulated after differentiation.

Cardiac Differentiation: iPSCs could be differentiated into cardiomyocytes that spontaneously began beating. Cardiomyocytes expressed TnTc, MEF2C, MYL2A, MYHCβ, and NKX2.5. Stem cell-associated genes will be downregulated after differentiation.

Teratoma Formation: iPSCs injected into immunodeficient mice may spontaneously formed teratomas after certain time, such as nine weeks. Teratomas are tumors of multiple lineages containing tissue derived from the three germ layers endoderm, mesoderm and ectoderm; this is unlike other tumors, which typically are of only one cell type. Teratoma formation is a landmark test for pluripotency.

Embryoid Body: Human ESCs in culture spontaneously form ball-like embryo-like structures termed "embryoid bodies," which consist of a core of mitotically active and differentiating hESCs and a periphery of fully differentiated cells from all three germ layers. iPSCs may also form embryoid bodies and have peripheral differentiated cells.

Blastocyst Injection: Human ESCs naturally reside within the inner cell mass (embryoblast) of blastocysts, and in the embryoblast, differentiate into the embryo while the blastocyst's shell (trophoblast) differentiates into extraembryonic tissues. The hollow trophoblast is unable to form a living embryo, and thus it is necessary for the embryonic stem cells within the embryoblast to differentiate and form the embryo. iPSCs injected by micropipette into a trophoblast to generate a blastocyst transferred to recipient females may result in chimeric living mouse pups: mice with iPSC derivatives incorporated all across their bodies with 10%-90 and chimerism.

ii. Epigenetic Reprogramming

Promoter Demethylation: Methylation is the transfer of a methyl group to a DNA base, typically the transfer of a methyl group to a cytosine molecule in a CpG site (adjacent cytosine/guanine sequence). Widespread methylation of a gene interferes with expression by preventing the activity of expression proteins or recruiting enzymes that interfere with expression. Thus, methylation of a gene effectively silences it by preventing transcription. Promoters of pluripotency-associated genes, including Oct-3/4, Rex1, and Nanog, may be demethylated in iPSCs, showing their promoter activity and the active promotion and expression of pluripotency-associated genes in iPSCs.

Histone Demethylation: Histones are compacting proteins that are structurally localized to DNA sequences that can effect their activity through various chromatin-related modifications. H3 histones associated with Oct-3/4, Sox2, and Nanog may be demethylated to activate the expression of Oct-3/4, Sox2, and Nanog.

B. Selection for Residue Free Feature

A reprogramming vector such as oriP-based vector in this invention could replicate extra-chromosomally and lose it presence in host cells after generations. However, an additional selection step for progeny cells essentially free of exogenous vector elements may facilitate this process. For example, a sample of progeny cell may be extracted to test the presence or loss of exogenous vector elements as known in the art (Leight and Sugden, 2001).

A reprogramming vector may further comprise a selection marker, more specifically, a negative selection marker, such as a gene encoding a thymidine kinase to select for progeny cells essentially free of such a selection marker. The human herpes simplex virus thymidine kinase type 1 gene (HSVtk) acts as a conditional lethal marker in mammalian cells. The HSVtk-encoded enzyme is able to phosphorylate certain nucleoside analogs (e.g., ganciclovir, an antiherpetic drug), thus converting them to toxic DNA replication inhibitors. An alternative or a complementary approach is to test the absence of exogenous genetic elements in progeny cells, using conventional methods, such as RT-PCR, PCR, FISH (Fluorescent in situ hybridization), gene array, or hybridization (e.g., Southern blot).

VIII. Vector Construction and Delivery

In certain embodiments, reprogramming vectors could be constructed to comprise additional elements in addition to nucleic acid sequences encoding reprogramming factors as described above to express these reprogramming factors in cells. One feature of these methods are use of extra-chromosomally replicating vectors, which will not be integrated into the host cell genome and may be lost during generations of replication. Details of components of these vectors and delivery methods are disclosed below.

A. Vector

The use of plasmid- or liposome-based extra-chromosomal vectors, e.g., oriP-based vectors, and/or vectors encoding a derivative of EBNA-1 permit large fragments of DNA to be introduced to a cell and maintained extra-chromosomally, replicated once per cell cycle, partitioned to daughter cells efficiently, and elicit substantially no immune response. In particular, EBNA-1, the viral protein responsible for the replication of the oriP-based expression vector, does not elicit a cellular immune response because it has developed an efficient mechanism to bypass the processing required for presentation of its antigens on MHC class I molecules (Levitskaya et al., 1997). Further, EBNA-1 can act in trans to enhance expression of the cloned gene, inducing expression of a cloned gene up to 100-fold in some cell lines (Langle-Rouault et al., 1998; Evans et al., 1997). Finally, the manufacture of such oriP-based expression vectors is inexpensive.

Other extra-chromosomal vectors include other lymphotrophic herpes virus-based vectors. Lymphotrophic herpes virus is a herpes virus that replicates in a lymphoblast (e.g., a human B lymphoblast) and becomes a plasmid for a part of its natural life-cycle. Herpes simplex virus (HSV) is not a "lymphotrophic" herpes virus. Exemplary lymphotrophic herpes viruses include, but are not limited to EBV, Kaposi's sarcoma herpes virus (KSHV); Herpes virus saimiri (HS) and Marek's disease virus (MDV). Also other sources of episome-based vectors are contemplated, such as yeast ARS, adenovirus, SV40, or BPV.

One of skill in the art would be well equipped to construct a vector through standard recombinant techniques (see, for example, Maniatis et al., 1988 and Ausubel et al., 1994, both incorporated herein by reference).

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide.

Such components also might include markers, such as detectable and/or selection markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

B. Regulatory Elements

Eukaryotic expression cassettes included in the vectors preferably contain (in a 5'-to-3' direction) an eukaryotic transcriptional promoter operably linked to a protein-coding sequence, splice signals including intervening sequences, and a transcriptional termination/polyadenylation sequence.

i. Promoter/Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

Promoters suitable for use in EBNA-1-encoding vector of the invention are those that direct the expression of the expression cassettes encoding the EBNA-1 protein to result in sufficient steady-state levels of EBNA-1 protein to stably maintain EBV oriP-containing vectors. Promoters may be also used for efficient expression of expression cassettes encoding reprogramming factors.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself to help fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, the World Wide Web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e.g., beta actin promoter (Ng, 1989, Quitsche et al., 1989), GADPH promoter (Alexander et al., 1988, Ercolani et al., 1988), metallothionein promoter (Karin et al., 1989; Richards et al., 1984); and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at Genbank, accession no. X05244, nucleotide 283-341) or a mouse mammary tumor promoter (available from the ATCC, Cat. No. ATCC 45007). A specific example could be a phosphoglycerate kinase (PGK) promoter.

ii. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

iii. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

iv. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

v. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

vi. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

vii. Origins of Replication

In order to propagate a vector in a host cell, it may contain one or more origins of replication sites (often termed "ori"), for example, a nucleic acid sequence corresponding to oriP of EBV as described above, which is a specific nucleic acid sequence at which replication is initiated. Alternatively a replication origin of other extra-chromosomally replicating virus as described above or an autonomously replicating sequence (ARS) can be employed.

viii. Selection and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, blasticidin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art.

C. Vector Delivery

Introduction of a reprogramming vector into somatic cells with the current invention may use any suitable methods for nucleic acid delivery for transformation of a cell., as described herein or as would be known to one of ordinary skill in the art. Such methods include, but are not limited to, direct delivery of DNA such as by ex vivo transfection (Wilson et al., 1989, Nabel et al., 1989); by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

i. Liposome-Mediated Transfection

In a certain embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a nucleic acid complexed with Lipofectamine (Gibco BRL) or Superfect (Qiagen). The amount of liposomes used may vary upon the nature of the liposome as well as the cell used, for example, about 5 to about 20 µg vector DNA per 1 to 10 million of cells may be contemplated.

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

ii. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. Recipient cells can be made more susceptible to transformation by mechanical wounding. Also the amount of vectors used may vary upon the nature of the cells used, for example, about 5 to about 20 µg vector DNA per 1 to 10 million of cells may be contemplated.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

iii. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

iv. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

v. Sonication Loading

Additional embodiments of the present invention include the introduction of a nucleic acid by direct sonic loading. LTK⁻ fibroblasts have been transfected with the thymidine kinase gene by sonication loading (Fechheimer et al., 1987).

vi. Receptor Mediated Transfection

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

vii Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Episomal Reprogramming of Human Foreskin Fibroblasts with Small Chemical Compounds Through screening known chemical compounds that affect iPS cell derivation, the inventors have identified several compounds that significantly improved the episomal reprogramming efficiency of human foreskin fibroblasts. BIX01294 (B) is a selective inhibitor of G9a histone methyltransferase. In combination with BayK8644, it was initially identified as small molecules that could enable reprogramming of mouse embryonic fibroblasts transduced with Oct4 and Klf4 alone (Shi et al., 2008). PD0325901 (P) is an inhibitor of mitogen-activated protein kinase kinase (MAPK/ERK kinase or MEK). CHIR99021 (C) is the most selective inhibitor of GSK3β, while A-83-01 (A) is a potent inhibitor of the TGF-β type I receptor ALK5, the Activin/Nodal receptor ALK4, and the nodal receptor ALK7. The combination of PD0325901 and CHIR99021 (2i) has allowed the efficient derivation of mouse ES cells from recalcitrant strains (Ying et al., 2008). In the 2i condition, the leukemia inhibitory factor (LIF), which was routinely used for mouse ES cell culture, though dispensable, promoted the clonogenicity and derivation of mouse ES cells (Ying et al., 2008). This 2i/LIF condition was shown to promote the reprogramming of mouse neural stem cells to true pluripotency (Silva et al., 2008). Interestingly, even though authentic rat ES cells could be readily derived from early embryos in this 2i/LIF condition (Buehr et al., 2008; Li et al., 2008), the addition of A-83-01 was shown to be required to sustain the long-term culture of rat iPS cells (Li et al., 2009). The combination of PD0325901, CHIR99021, A-83-01 and LIF was also shown to be able to select and stabilize atypical mouse ES cell-like human iPS cells from lentivirus-mediated reprogramming culture (Li et al., 2009); however, no effects of the combination of these inhibitors on reprogramming, especially episomal reprogramming, have been documented.

For cell culturing, human ES cells and iPS cells were maintained on irradiated mouse embryonic fibroblasts (MEFs) in DMEM/F12 culture medium supplemented with 20% KnockOut serum replacer, 0.1 mM non-essential amino acids, 1 mM Glutamax (all from Invitrogen, Carlsbad, Calif.), 0.1 mM β-mercaptoethanol and 100 ng/ml zebrafish basic fibroblast growth factor (zbFGF) (Amit et al., 2000; Ludwig et al., 2006a; Thomson et al., 1998). The feeder-free culture on Matrigel™ (BD Biosciences, Bedford, Mass.) with conditioned medium was carried out as previously described (Xu et al., 2001) except with 100 ng/ml zbFGF. Human newborn foreskin fibroblasts (Cat# CRL2097™, ATCC, Manassas, Va.) and adult fibroblasts from a 42-year old skin biopsy were cultured in DMEM (Invitrogen) supplemented with 10% defined fetal bovine serum (FBS, Hyclone Laboratories, Logan, Utah), 0.1 mM non-essential amino acids, 2 mM Glutamax (all from Invitrogen), 0.1 mM β-mercaptoethanol and 4 ng/ml zbFGF. mTeSR™1 was obtained from Stem Cell Technologies Inc. (Vancouver, Canada). N2B27 medium was prepared as the following: DMEM/F12 culture medium supplemented with 1×N2 supplement, 1×B-27 supplement, 0.1 mM non-essential amino acids, 1 mM Glutamax (all from Invitrogen), 0.1 mM β-mercaptoethanol.

For episomal reprogramming of human somatic cells, human foreskin fibroblasts, episomal vectors (FIG. 1A, 7.3 µg of pEP4EO2SCK2MEN2L and 3.2 µg of pEP4EO2SET2K) (Yu et al., 2009) were cotransfected into $1 \times 10^6$ cells via nucleofection (NHDF-VPD-1001 with program U-20, Amaxa, Walkersville, Md.). Transfected foreskin fibroblasts from each nucleofection were directly plated to 3×10-cm MEF-seeded dishes in fibroblast culture medium. For adult skin fibroblasts, 7.3 µg of pEP4EO2SCK2MEN2L and 6.4 µg of pEP4EO2SET2K were cotransfected into $1 \times 10^6$ cells via nucleofection (NHDF-VPD-1001 with program U-20, Amaxa). Transfected adult skin fibroblasts from each nucleofection were directly plated to 1×10-cm MEF-seeded dish in fibroblast culture medium due to lower cell survival. The next day, the fibroblast culture medium was replaced with either fresh fibroblast culture medium or various reprogramming medium (e.g., human ES cell culture medium previously conditioned with MEFs-CM, human ES cell culture medium, mTeSR™1, N2B27) supplemented with or without zbFGF (100 ng/ml), with or without the following compounds: H—HA-100 (10 µM); B—BIX01294 (1 µM); P—PD0325901 (0.5 µM); C-CHIR99021 (3 µM); A-A-83-01 (0.5 µM) and L-hLIF (10 ng/ml). To obtain human ES cell-like iPS cells, reprogramming medium was replaced with either CM supplemented with 100 ng/ml zbFGF or mTeSR™1 on day 13-20 post transfection. To obtain a distinct type of iPS (piPSC for partially reprogrammed iPSCs) cells, reprogramming medium was replaced with CM or N2B27 medium supplemented with PCAL. Alkaline phosphatase staining (Cat# SCR004, Millipore, Billerica, Mass.) was carried out between day 18 and day 24 post transfection to check the reprogramming efficiency.

Figure 1B:
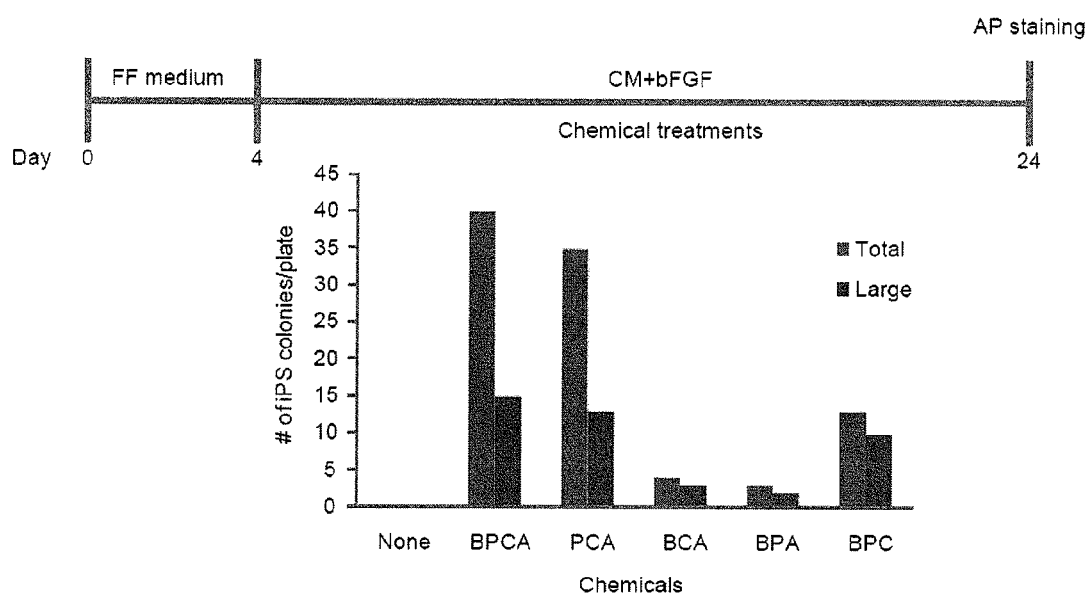
Figure 1C:
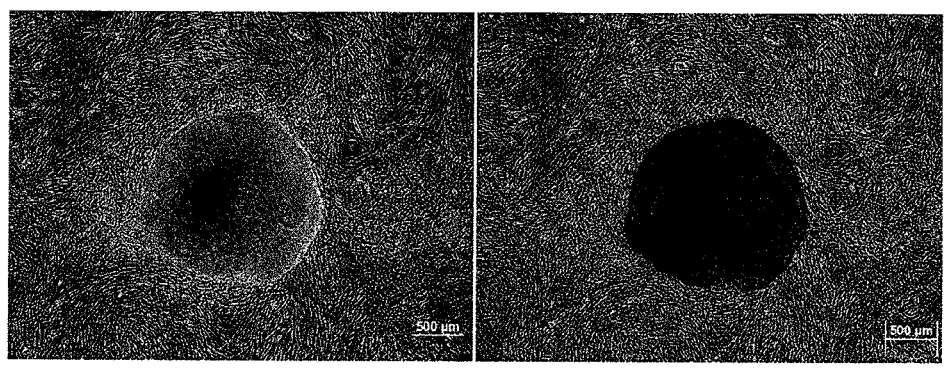
Figure 2A:
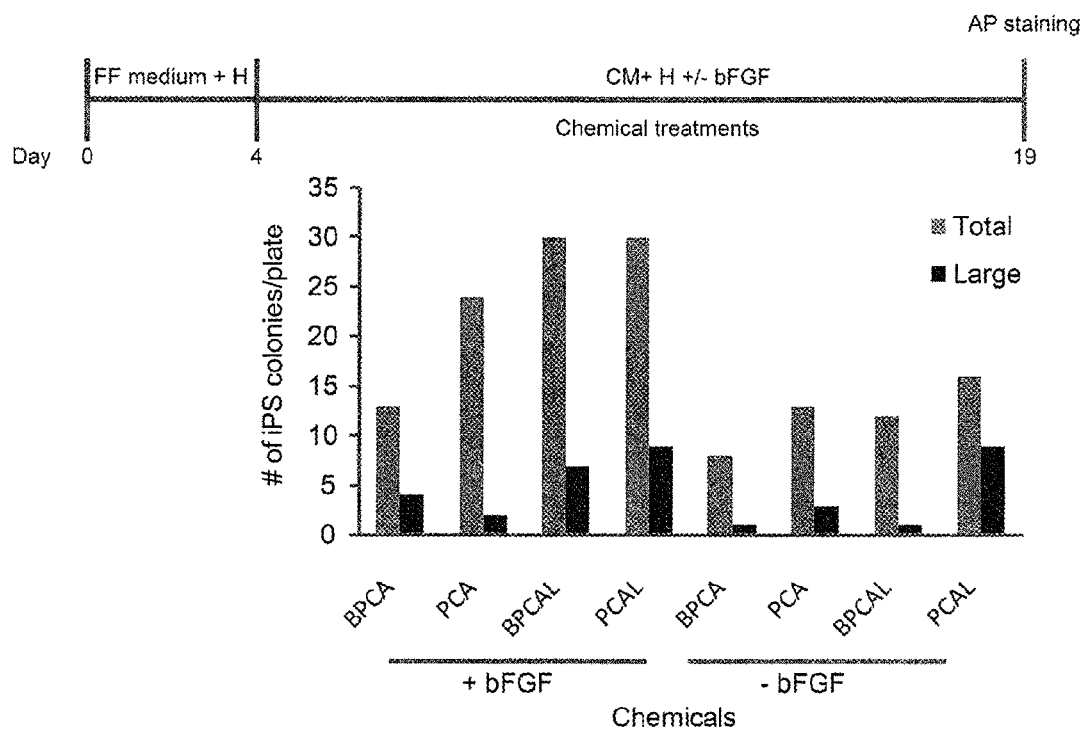
FIGS. 2A-2B. Improving episomal reprogramming of human foreskin fibroblasts with small chemical compounds.

BIX01294, though on its own, could improve reprogramming by episomal vectors (FIG. 1A), showed no or only slight benefit in combination of PD0325901, CHIR99021 and A-83-01 (FIGS. 1B and 2A). Different from mouse neural stem cell reprogramming (Silva et al., 2008), where PD0325901 and CHIR99021 alone were sufficient, all three chemical compounds (PD0325901, CHIR99021 and A-83-01) were needed to achieve the best reprogramming efficiency (FIG. 1B). iPS cell colonies obtained could be readily discernible from non-iPS cell colonies in the presence of all three chemical compounds (FIG. 1C). This would allow the maintenance of iPS cell clonality during picking and expansion, a great improvement from the previous protocol (Yu et al., 2009) where passaging of primary reprogramming culture was required to identify iPS cells from non-iPS cells. HA-100 was shown to improve human ES cell cloning efficiency. It was included in subsets of experiments. The addition of human LIF (hLIF, or L) further facilitated the episomal reprogramming with PD0325901, CHIR99021 and A-83-01 (FIG. 2A). Moreover, with LIF addition, the first appearance of iPS cells was approximately 3-4 days earlier (~day 14 post transfection), and more large iPS cell colonies were present (FIG. 2A).

Figure 2B:
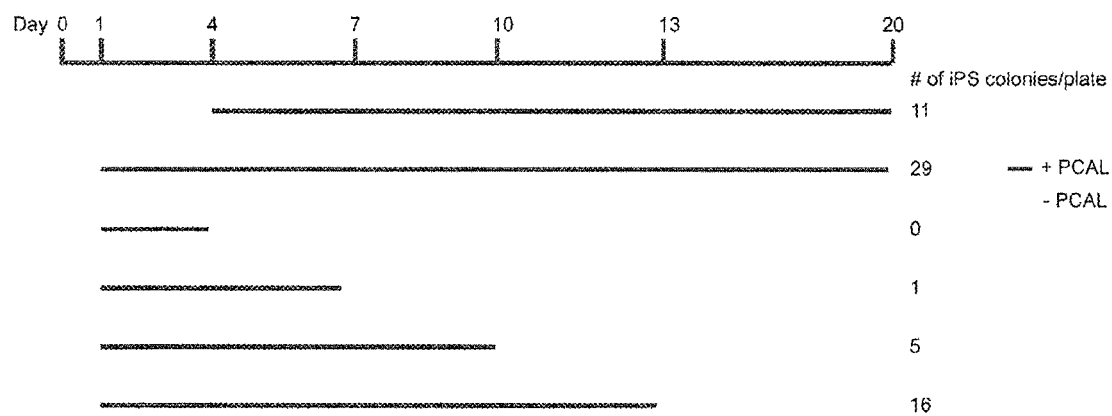
Figure 4A:
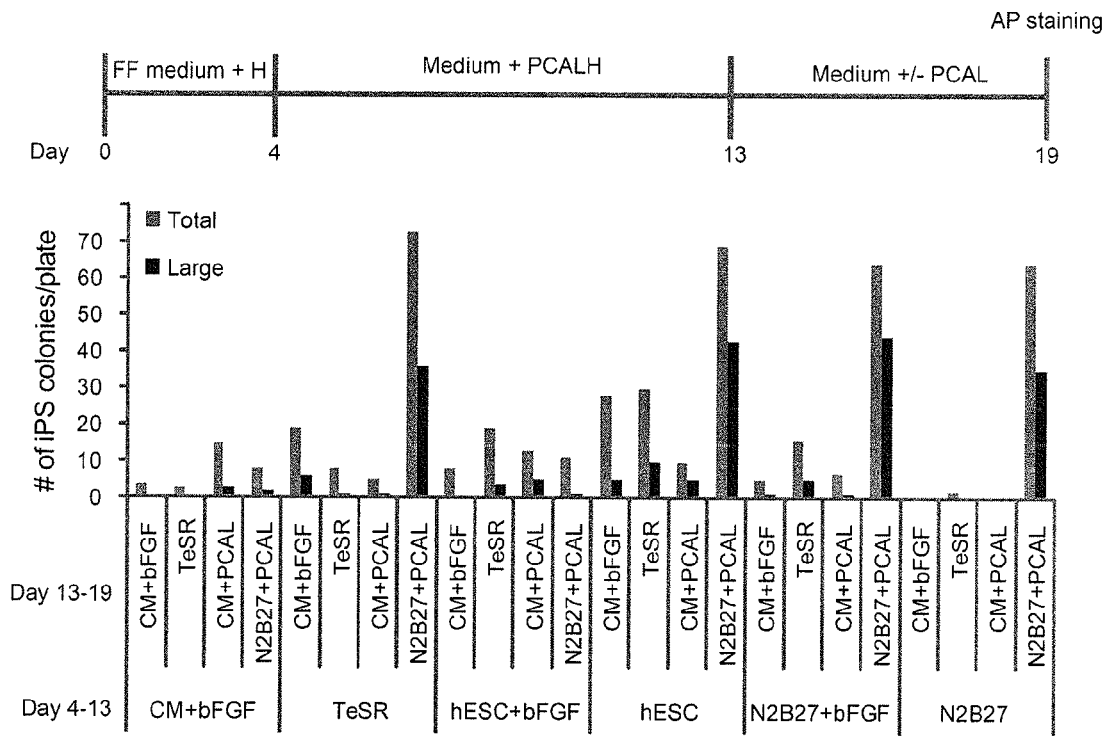
FIGS. 4A-4B. Episomal reprogramming in defined medium supplemented with chemical compounds.

Since PD0325901 efficiently inhibits MEK activity, a downstream target of bFGF signaling, the effect of bFGF on reprogramming was also examined. As shown in FIG. 2A, high concentration of bFGF (100 ng/ml) was beneficial under this particular reprogramming condition. This effect most likely resulted from non-MEK mediated effects of high bFGF level. The effect of high bFGF level appeared to depend on specific reprogramming culture medium. For example, bFGF showed beneficial effects when conditioned human ES cell culture medium (CM) and serum-free defined N2B27 medium were used (FIGS. 2A and 4A), while the opposite effect was observed when unconditioned human ES cell culture medium was tested (FIG. 4A). As shown in FIG. 2B, early addition of chemical compounds increased reprogramming efficiency, and longer chemical treatment was needed to achieve the best reprogramming efficiency.

Figure 3A:
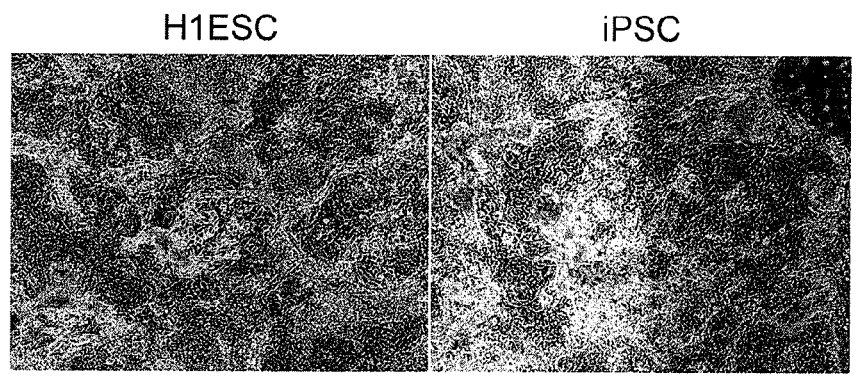
FIGS. 3A-3D. Distinct iPS cells can be obtained from episomal reprogramming culture treated with chemical compounds.

The proliferation of human ES cells and human ES cell-like iPS cells requires the activation of FGF and TGFβ/Activin signaling pathways, similar to mouse EpiSCs derived from post-implantation mouse epiblasts. PD0325901 inhibits MEK, a downstream target of FGF signaling, and A-83-01 inhibits TGFβ/Activin signaling. The observation that both drugs increased reprogramming was rather surprising. As shown in FIG. 3A, both human ES cells and human ES cell-like iPS cells underwent efficient differentiation in the presence of the reprogramming chemical cocktail (PD0325901, CHIR99021, A-83-01 and hLIF). To confirm the identity of iPS cells derived in the presence of the chemical cocktail, iPS cells were picked for expansion in normal human ES cell culture conditions. Initial tests yielded many differentiated colonies with small clusters of undifferentiated cells, which was very different from iPS cells derived in the absence of the chemical cocktail, where most colonies remained undifferentiated. This result suggests that most iPS cells derived in the presence of the chemical cocktail were different from normal human ES cell-like iPS cells.

In the presence of the chemical cocktail, iPS cells could be picked and expanded on mouse embryonic fibroblast feeder (FIG. 3C), though with much differentiation, suggesting the need for culture optimization. Removal of the chemical cocktail by culturing these iPS cells under normal human ES cell culture condition resulted in significant differentiation, many of which formed rosette structures (FIG. 3D), suggesting that these cells are capable of efficient in vitro neural differentiation in contrast to most human iPS cells previously derived. These data and the observation that hLIF improved reprogramming suggest that this type of human iPS cells are distinct from normal human ES cell-like iPS cells, and was later found to be an intermediate stage of reprogrammed cells.

Figure 3B:
Figure 3C:
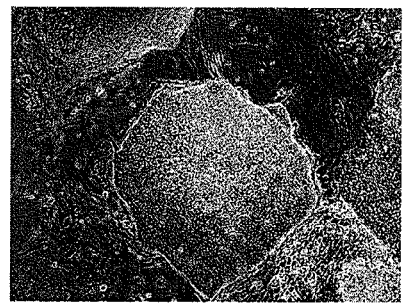
Figure 3D:
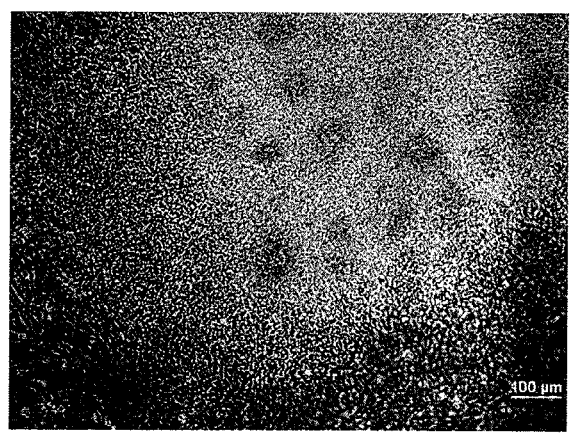

The presence of small undifferentiated cell clusters when chemically derived iPS cells were picked and expanded under normal human ES cell culture condition raised a possibility that normal human ES cell-like iPS cells could also be derived from chemical treated reprogramming culture. Indeed, when the chemical cocktail was removed from reprogramming culture following a minimum of ten-day treatment, normal human ES cell-like iPS cells were readily expanded under normal human ES cell culture conditions (FIG. 3B). The origin of these iPS cells remains an interesting question. They can either be expanded from pre-existing normal human ES cell-like iPS cells, or they can be derived from piPS cells as the piPS cells could readily give rise to normal human ES cell-like iPS cells under normal human ES cell culture conditions.

Reprogramming of human somatic cells was generally carried out on MEF feeders with human ES cell culture medium previously conditioned with MEFs (CM). The quality of MEFs varies significantly between different batches, which greatly impact the consistency of reprogramming efficiency. And the preparation of MEF and CM can be quite labor-intensive. Additionally, both MEF feeders and CM support the growth of a wide variety of cell types, which could pose significant restricts on reprogramming efficiency, as proliferation of non-iPS cells during reprogramming can negatively affect reprogramming. To overcome this problem, different culture medium were tested. As shown in FIG. 4A, TeSR, unconditioned human ES cell culture medium without bFGF supplement and N2B27 medium supported robust episomal reprogramming, higher than CM supplemented with bFGF.

Figure 4B:
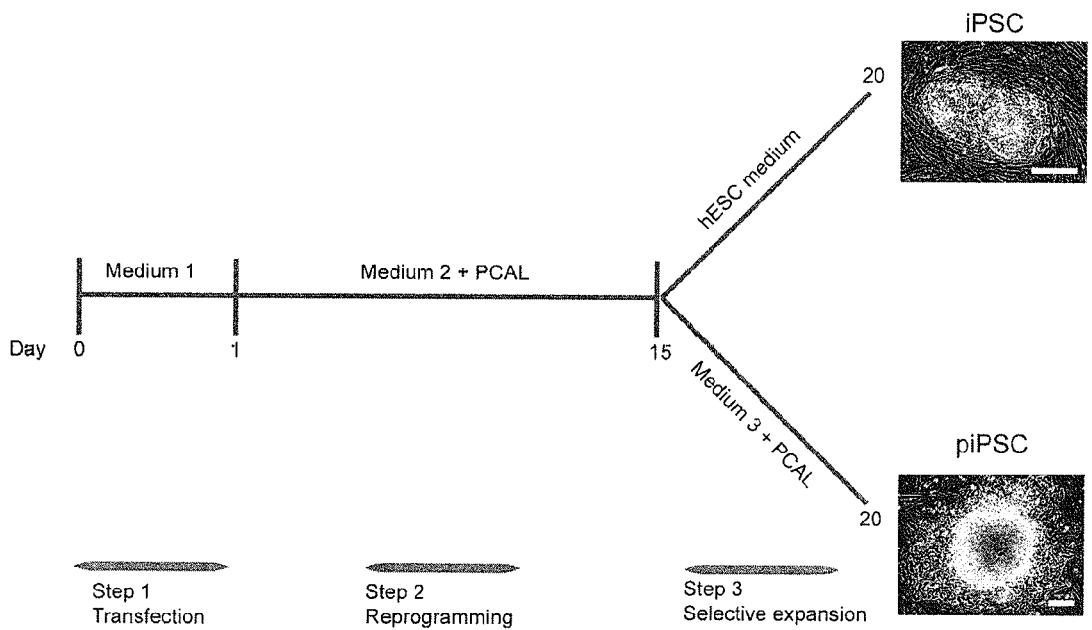

Moreover, different reprogramming medium (step 2, FIG. 4B) gave rise to two types of iPS cells with different efficiency. Depending on which reprogramming medium was used, the efficiency of obtaining two types of iPS cells differed as shown in FIG. 4A. For example, when hESC medium (+PCALH) was used in reprogramming, human ES cell-like iPS cells can be readily obtained from the reprogramming culture using either CM+bFGF or TeSR expansion medium, and piPS cells when using N2B27+PCAL expansion medium. However, no or rare human ES cell-like iPS cells could be obtained when N2B27 medium (+PCALH) was used as reprogramming medium.

This suggests that the combination of reprogramming medium (step 2, FIG. 4B) and expansion medium (step 3, FIG. 4B) will likely impact the level of iPS cell heterogeneity in the reprogramming culture. Optimal medium combinations for the derivation of each iPS cell type can be selected to minimize iPS cell clone to clone variation.

Example 2

Feeder-Free Episomal Reprogramming with Small Molecules

Human iPSCs, similar to human embryonic stem cells (ESCs), are capable of unlimited proliferation and have the potential to differentiate into all cell types of the body. These cells, thus, have applications in basic biology, disease modeling, drug development, and transplantation therapies. By expressing a defined set of reprogramming factors, iPSCs have been generated from many cell types of different species (Takahashi et al., 2007; Yu et al., 2007; Takahashi and Yamanaka, 2006; Liu et al., 2008; Esteban et al., 2009; Loh et al., 2009; Sun et al., 2009; Shimada et al., 2010). Initial methods for iPSC generation employed genome-integrating retroviral or lentiviral vectors (Yu et al., 2007; Takahashi and Yamanaka, 2006). These approaches could produce tumorigenic insertional mutations, and residual or reactivation of transgene expression during iPSC differentiation could affect lineage choice and the functionality of iPSC derivatives (Yu et al., 2007; Okita et al., 2007). To overcome these problems, various methods were developed to derive footprint-free iPSCs, including repeated treatments with reprogramming factors (plasmids, minicircle DNA, non-integrating adenoviral vectors and proteins), transposons and RNA viral vectors (Okita et al., 2008; Stadtfeld et al., 2008; Fusaki et al., 2009; Kaji et al., 2009; Woltjen et al., 2009; Zhou et al., 2009; Jia et al., 2010). However, these methods suffer one or more of the following limitations: the unacceptable low reprogramming efficiency; the labor-intensive removal of reprogramming factors from iPSCs; the requirement for viral packaging or feeder cells. Thus, there is a need to develop a simple and efficient feeder-free method to enable the routine derivation of footprint-free iPSCs from many human donor samples and eventually the derivation of clinical-grade human iPSCs.

Footprint-free human iPSCs were previously generated using oriP/EBNA-1 (Epstein-Barr nuclear antigen-1) episomal vectors to deliver reprogramming genes (OCT4, SOX2, NANOG, LIN28, c-MYC, KLF4 and SV40LT) (Yu et al., 2009). Compared to other methods, this approach has several advantages. First, the oriP/EBNA-1 vectors have a wide host cell range, enabling the application of this method to many human cell types. Second, it does not require viral packaging. Third, no repeated treatments with reprogramming factors are needed. A single transfection of episomal vectors is sufficient for the derivation of human iPSCs. Moreover, higher transfection efficiency can be achieved with these vectors due to the oriP/EBNA-1-mediated nuclear import and retention of vector DNA (Middleton and Sugden, 1994). Fourth, the oriP/EBNA-1 vectors replicate once-per-cell cycle and are generally present at low copy number per cell, thus minimizing DNA rearrangement and genome integration (Yates and Guan, 1991). Last, the removal of episomal vectors from human iPSCs can be accomplished by simple cell culture without any additional manipulation, due to the silencing of the viral promoter driving EBNA-1 expression in iPSCs, and the inherent instability of oriP/EBNA-1 episomal state—stably established episomes are lost from cells at a rate of ~5% per cell generation due to defects in vector synthesis and partitioning (Nanbo et al., 2007). Despite these advantages, our original oriP/EBNA-1 episomal approach gave a low reprogramming efficiency (~3 iPSC colonies from ~$1 \times 10^6$ input human foreskin fibroblasts), and used mouse embryonic fibroblast (MEF) feeder cells, which seriously limit the industrial and therapeutic applications of this method.

Figure 5A:
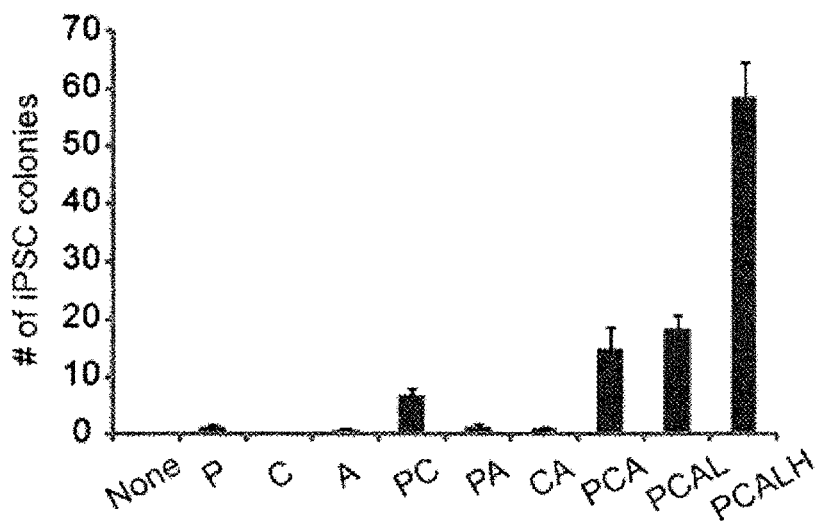
FIGS. 5A-5C. Improving episomal reprogramming efficiency with small molecules.
Figure 5B:
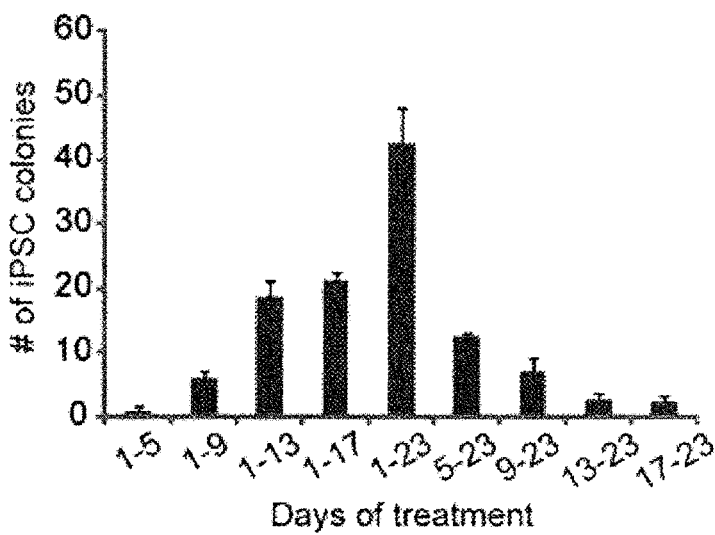

To overcome these limitations, we first screened small molecules for improved episomal reprogramming efficiency. The oriP/EBNA-1 vectors can establish stable episomes in only 1-10% of transfected cells (Leight and Sugden, 2001). During the first two weeks post-transfection, transfected cells lose oriP/EBNA-1 vectors at >25% per cell generation, which is accompanied by transgene silencing likely mediated through DNA methylation (Kameda et al., 2006). The loss of transgene expression during the first two weeks post-transfection, either due to vector loss or transgene silencing, is mainly responsible for the low episomal reprogramming efficiency. Thus, small molecules that could accelerate reprogramming process, or reduce transgene silencing, or increase the efficiency of stable episome establishment are expected to improve reprogramming. By testing small molecules previously shown to promote reprogramming, we found that the episomal reprogramming efficiency could be greatly enhanced with the addition of a MEK inhibitor PD0325901, a GSK3β inhibitor CHIR99021, and a TGF-β/Activin/Nodal receptor inhibitor A-83-01 (FIG. 5A). Previous studies showed that TGF-β signaling inhibitors together with the MEK inhibitor PD0325901 resulted in >100-fold increase in the viral reprogramming efficiency (Lin et al., 2009). As shown in FIG. 1a, the TGF-β signaling inhibitor A-83-01, either alone or together with the MEK inhibitor PD0325901, had minimal effect on episomal reprogramming. All three inhibitors PD0325901, CHIR99021, and A-83-01 were required to achieve the maximal increase in reprogramming efficiency. Human leukemia inhibitory factor (hLIF), though did not significantly improve episomal reprogramming efficiency, increased the proliferation of reprogramming intermediates. The ROCK inhibitor HA-100, though had minimal effect on its own, further increased the episomal reprogramming efficiency in the presence of PD0325901, CHIR99021, A-83-01 and hLIF. The effect of HA-100 might not be mediated through its function in promoting cell survival of individualized human iPSCs, since it could not be replaced with other inhibitors that have similar functions, e.g. H-1152 and blebbistatin (Watanabe et al., 2007; Chen et al., 2010). The increase in the episomal reprogramming efficiency correlated with the duration of small molecule treatment (FIG. 5B). Treatment between day 1 and 5 post-transfection, particularly, appeared to be important for their maximal effect.

Figure 5C:
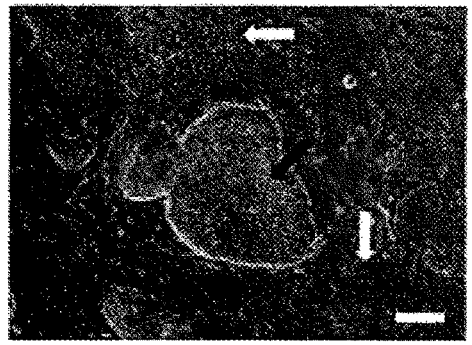

Human ESCs show similar gene expression and culture requirements as mouse epiblast-derived stem cells (EpiSCs), and differ from mouse ESCs derived from earlier blastocyst stage. Previous studies demonstrated the ability of PD0325901, CHIR99021, A-83-01 and hLIF to expand mouse ESC-like human iPSCs from reprogramming cultures that were not previously exposed to these inhibitors (Li et al., 2009). These mouse ESC-like human iPSCs readily differentiated following withdrawal of these small molecules. Human ESCs, on the contrary, differentiated rapidly in the presence of these small molecules. Surprisingly, the human episomal iPSCs obtained in the continuous presence of small molecules exhibited good proliferation with minimal differentiation under conditions for human ESCs (without small molecules), but underwent extensive differentiation when picked and expanded in the same condition used for their derivation, i.e. in the presence of small molecules (FIG. 5C), suggesting that these iPSCs were likely in a pluripotent state similar to human ESCs, not mouse ESCs. The seemingly conflicting results could be explained by the presence of activities that mitigated the effectiveness of small molecules in the MEF-conditioned human ESC medium used for reprogramming (e.g., bFGF and ligands for TGF-β signaling), which might enable the generation of human ESC-like pluripotent state in the presence of small molecules.

Figure 6A:
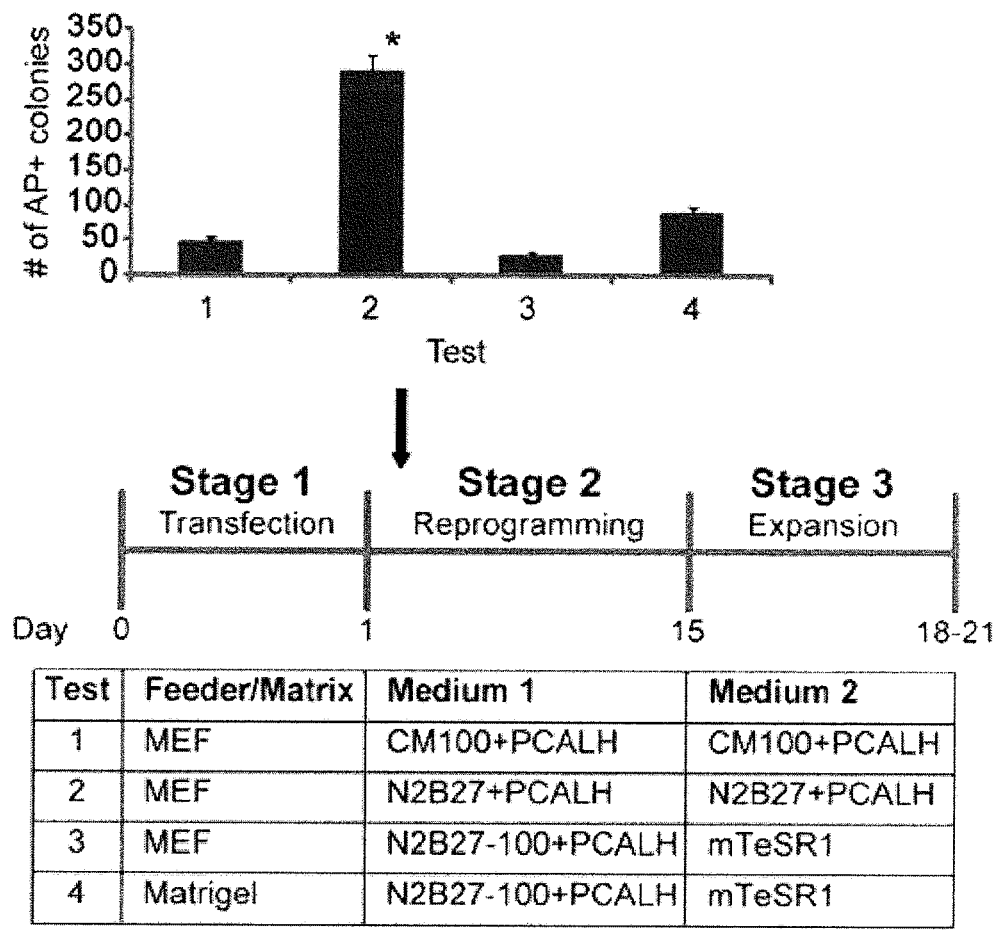
FIGS. 6A-6D. Developing feeder-free conditions for episomal reprogramming.
Figure 6B:
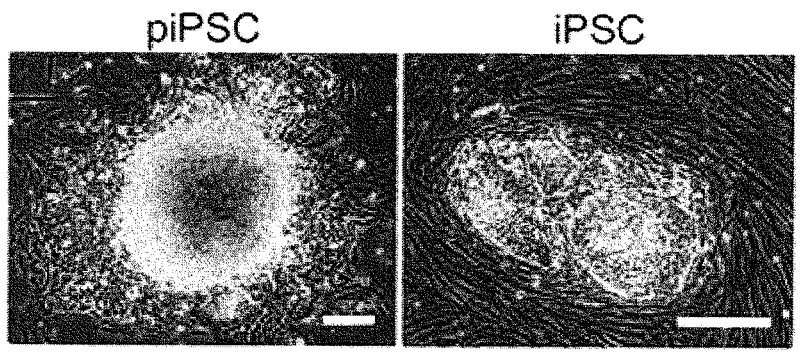
Figure 6C:
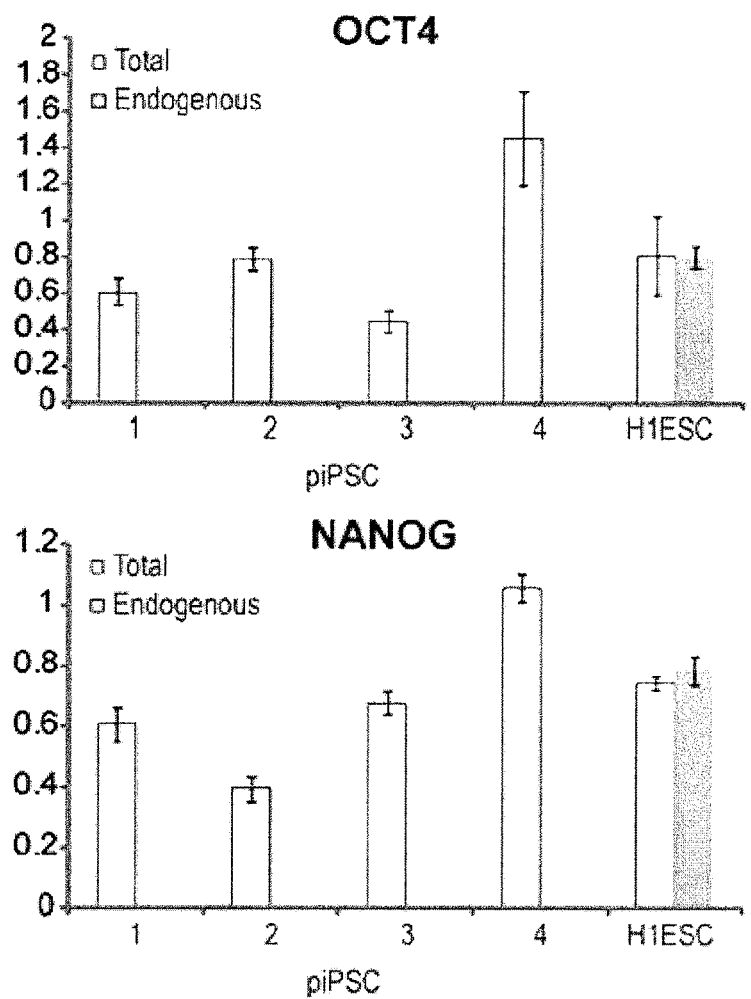
Figure 10A:
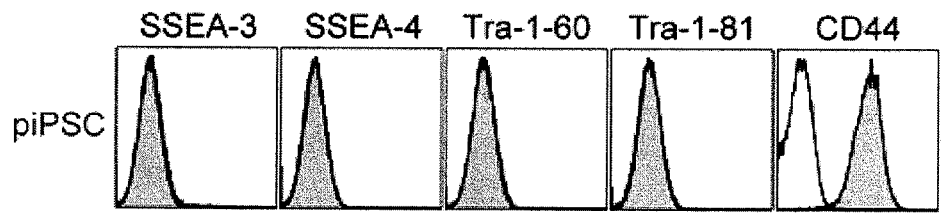
FIGS. 10A-10C. Developing feeder-free conditions for episomal reprogramming.
Figure 10B:
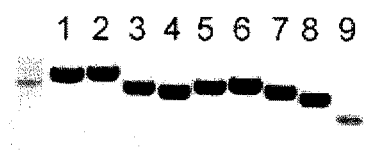

Since the KnockOut™ serum replacement used in the human ESC medium contains unknown factors that might interfere with reprogramming, to find out whether we can efficiently generate mouse ESC-like iPSCs by using culture media lacking small molecule-mitigating activities, and to identify defined reprogramming conditions, experiments were set out to find defined media that could support episomal reprogramming. Specifically, the defined N2B27 medium was tested, which has a simple formulation and was able to support the proliferation of human ESCs when supplemented with cytokines (Liu et al., 2006). As shown in FIG. 6A, the N2B27 medium supplemented with small molecules gave rise to nearly 6-fold higher number of colonies stained positive for alkaline phosphatase (a human pluripotent stem cell marker) (test 2 vs. test 1). These colonies (piPSC for partially reprogrammed iPSCs) had a mouse ESC-like domed morphology, which differs from the flattened morphology typical of human ESC-like iPSC colonies (FIG. 6B). They could be picked and expanded for more than 7 passages in the N2B27 medium supplemented with small molecules. Flow cytometry analysis of these cells, however, failed to detect the expression of human pluripotent stem cell-specific antigens (SSEA-3, SSEA-4, Tra-1-60 and Tra-1-81), while the expression of a fibroblast marker CD44 was present (FIG. 10A). Quantitative RT-PCR analysis also failed to detect any expression of the endogenous OCT4 and NANOG, two essential markers for human pluripotent stem cells (FIG. 6C). These results suggested that the colonies were partially reprogrammed iPSCs, not human ESC-like iPSCs as those derived with the MEF-conditioned human ESC medium (test 1) or mouse ESC-like iPSCs as those virally derived in the presence of PD0325901, CHIR99021 and LIF, thus illustrating the important influence of reprogramming culture conditions on the pluripotent state of iPSCs (Hanna et al., 2010; Buecker et al., 2010). Interestingly, the piPSCs contained abundant episomal vectors and maintained high-level transgene expression even after multiple passages in the N2B27 medium supplemented with small molecules (FIG. 6C and FIG. 10B), suggesting the likely involvement of small molecules in the retention of episomal vectors and transgene expression. Removal of small molecules led to occasional appearance of human ESC-like iPSCs amid extensive differentiation after two weeks' culture of piPSCs in the defined human ESC medium mTeSR1. Thus, though the current reprogramming conditions failed to yield mouse ESC-like human episomal iPSCs, modifications could be made in the reprogramming protocol to enable the derivation of human ESC-like iPSCs in the N2B27 medium.

Figure 6D:
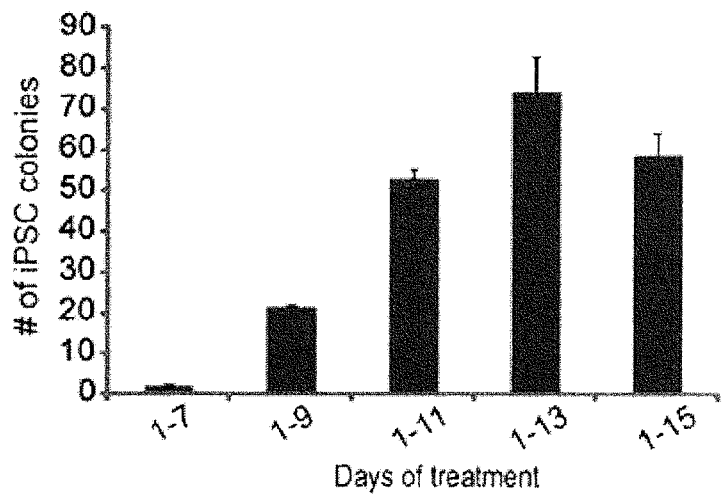
Figure 10C:
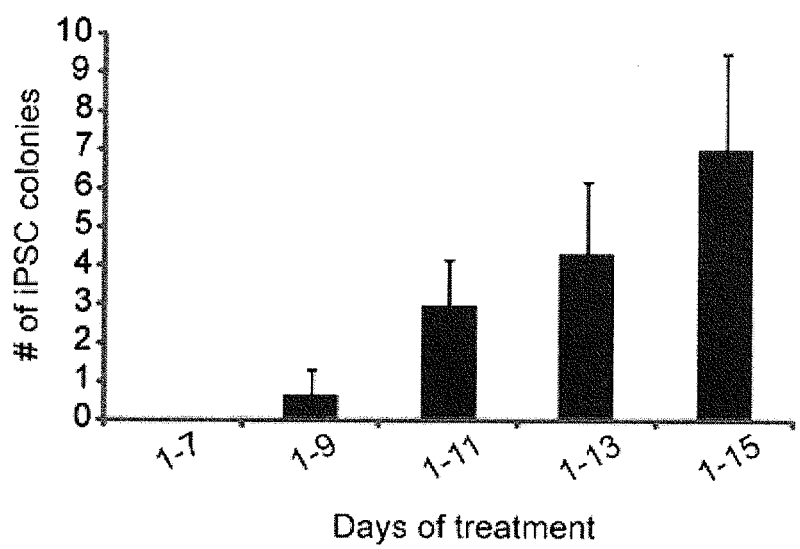

To this end, the inventors divided the reprogramming process into three stages: transfection (stage 1), reprogramming (stage 2), and expansion (stage 3) where mTeSR1 was used (FIG. 6A). When the N2B27 medium supplemented with small molecules was used at stage 2 to support reprogramming, only rare conversion of piPSCs to human ESC-like iPSCs could be observed, suggesting that the transgene expression during expansion in mTeSR1 was insufficient to reactivate the expression of the endogenous pluripotent genes in most piPSCs. Thus the inventors examined whether it was possible to improve episomal reprogramming by adding additional cytokines in the N2B27 medium supplemented with small molecules (stage 2). Of factors that are implicated in the proliferation of human ESCs, bFGF and TGF-β/Activin/Nodal signaling are of particular importance. As inhibition of TGF-β/Activin/Nodal signaling by A-83-01 facilitated reprogramming (FIG. 5A), the inventors tested the effect of bFGF on episomal reprogramming. Indeed, addition of high concentration bFGF to the N2B27 medium yielded reasonable number of human ESC-like iPSC colonies (test 3) (FIG. 6A). This result was consistent with previous observations that high concentration bFGF supported human ESC growth through multiple pathways besides MEK. Importantly, Matrigel™ was able to replace MEF feeder cells with even higher reprogramming efficiency (test 4) (FIG. 6A). Time-course experiments showed a requirement for an optimal time window of small molecule treatment (FIG. 6D). Not surprisingly, replacement of the N2B27 medium with the TGF-β-containing mTeSR1 at stage 2 significantly decreased the episomal reprogramming efficiency (FIG. 10C). Thus, using small molecules and defined media, we have established a feeder free episomal reprogramming method with significantly improved efficiency (>220 iPSC colonies from $1\times10^6$ input human foreskin fibroblasts, >70-fold increase) (FIG. 6D).

Figure 7A:
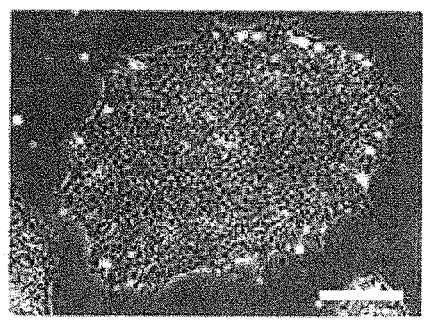
FIGS. 7A-7F. Characterization of iPSCs derived under feeder-free conditions with defined media.
Figure 7B:
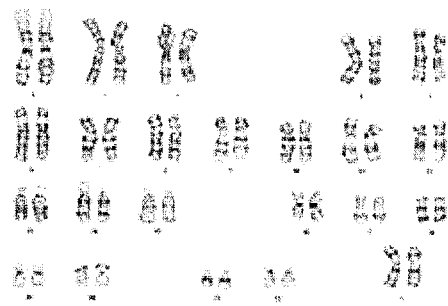
Figure 7C:
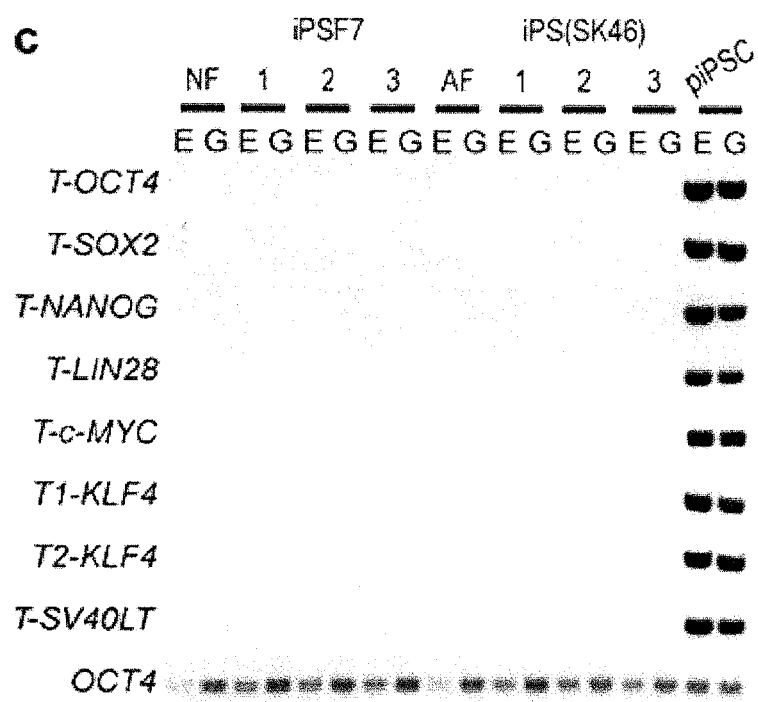
Figure 7D:
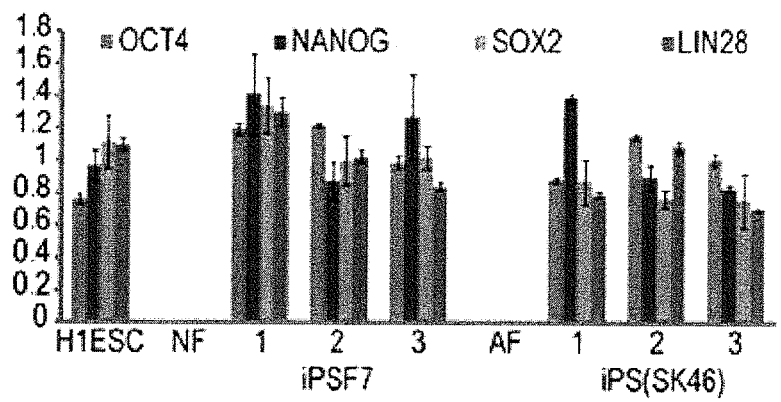
Figure 7E:
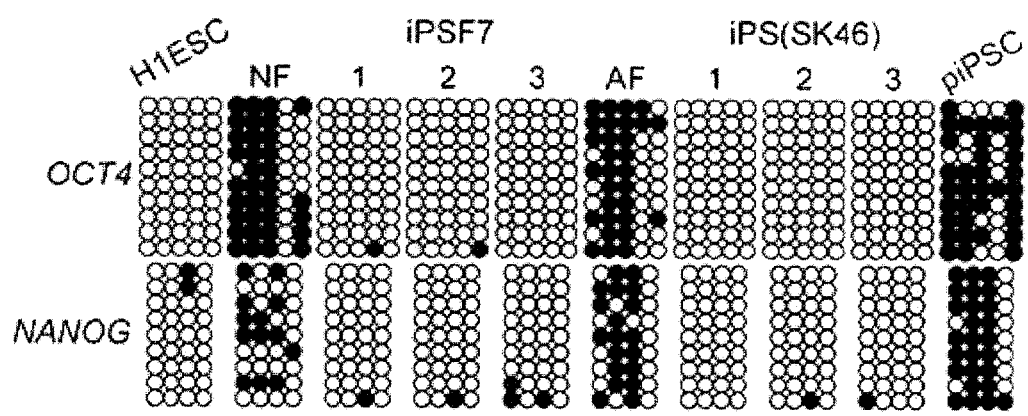
Figure 7F:
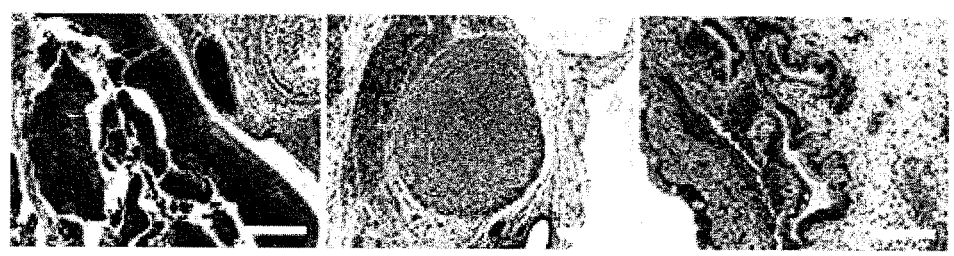
Figure 11A:
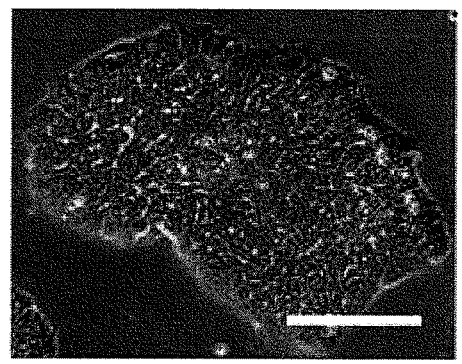
FIGS. 11A-11E. Characterization of iPSCs derived under feeder-free conditions with defined media.
Figure 11B:
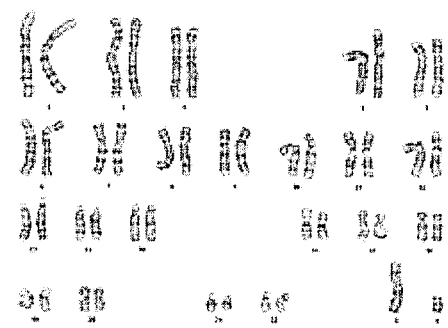
Figure 11C:
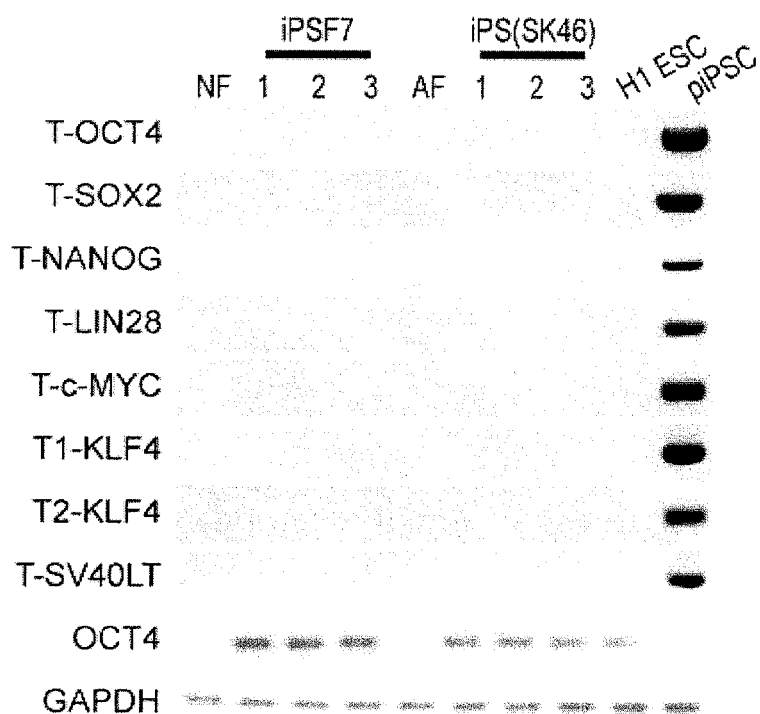
Figure 11D:
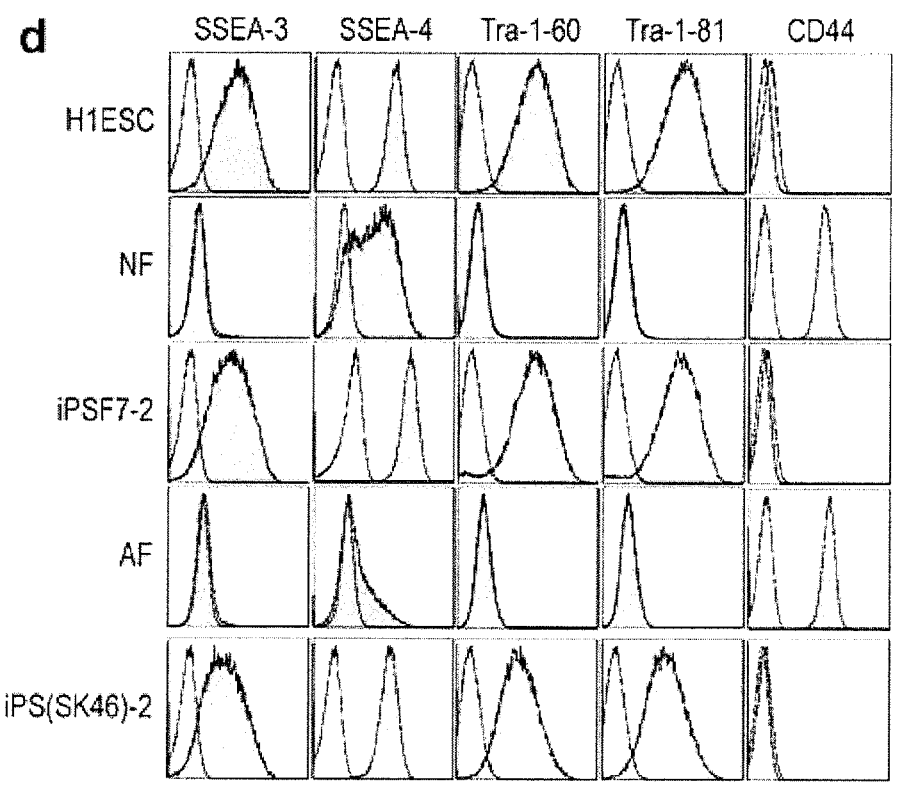
Figure 11E:
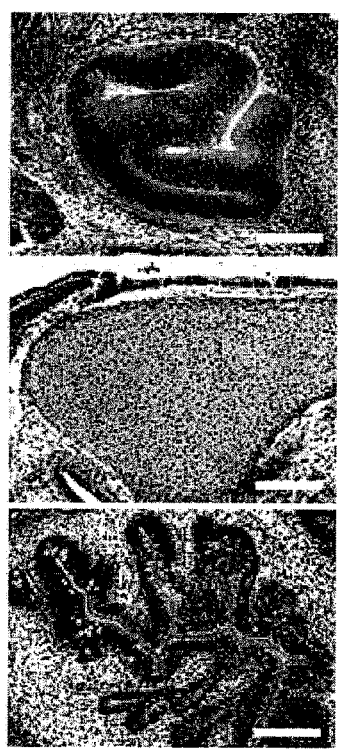
Figure 12:
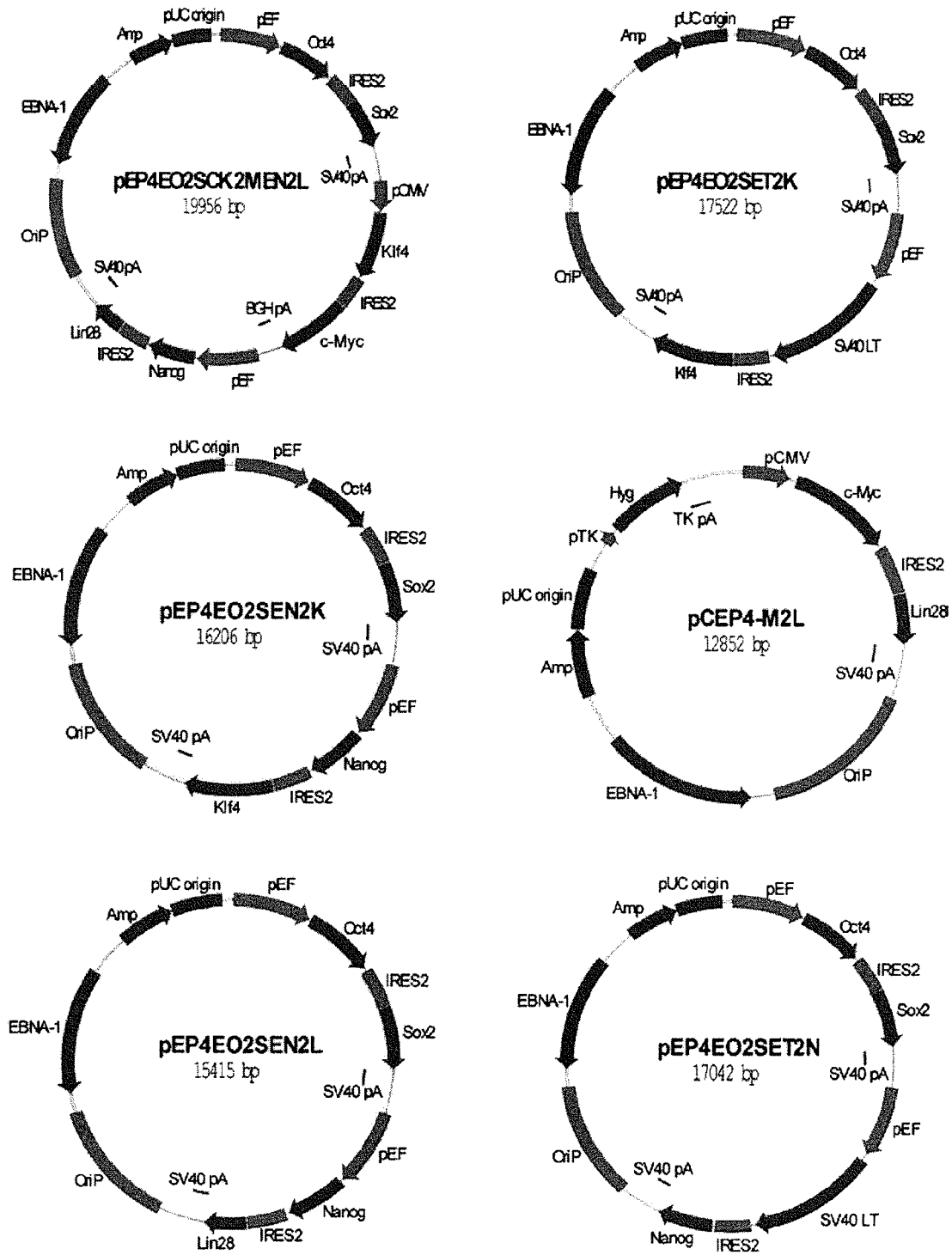
FIG. 12. Episomal reprogramming vectors. A detailing of the genetic components of the episomal reprogramming vectors. pEF: the eukaryotic elongation factor 1α promoter; pCMV: the cytomegalovirus immediate-early promoter; IRES2: internal ribosome entry site; SV40 pA: Simian vacuolating virus 40 polyadenylation signal; oriP: EBV origin of replication; EBNA-1: EBV nuclear antigen 1; Amp: ampicillin bacterial resistance selection cassette; pUC origin: bacterial origin of replication; Oct4: octamer4 transcription factor; Sox2: Sox2 transcription factor; c-Myc: c-Myc transcription factor; Klf4: Kreuppel-like factor transcriptional modulator; SV40LT: SV40 large T gene; Nanog: NANOG transcription factor; Lin28: Lin28 mRNA binding protein.

With the newly developed feeder-free reprogramming condition, we have successfully derived human ESC-like iPSCs from adult skin fibroblasts. When picked and expanded in mTeSR1, these iPSCs showed typical human ESC morphology (e.g. compact colonies, high nucleus-to-cytoplasm ratios and prominent nucleoli), and had normal karyotypes (FIGS. 7A-7F and FIGS. 11A-11E). Most iPSC colonies showed no transgene expression or genomic integration, and had completely lost episomal vectors after multiple passages (>14) as demonstrated by PCR and RT-PCR analysis (FIG. 7C and FIG. 11C). They expressed typical human ESC-specific antigens (SSEA-3, SSEA-4, Tra-1-60 and Tra-1-81), down-regulated the expression of the fibroblast marker CD44 (FIG. 11D), and reactivated the expression of the endogenous pluripotent genes (OCT4, NANOG, SOX2 and LIN28) (FIG. 7D). Both the OCT4 and NANOG promoters were demethylated in these iPSCs, similar to human ESCs and in contrast to the parental fibroblasts and piPSCs (FIG. 7E). When injected into immunocompromised mice, they formed teratomas consisting of derivatives of all three germ layers, demonstrating the pluripotency of these iPSCs (FIG. 7F and FIG. 11E).

Figures 8A, 8B, 8C:
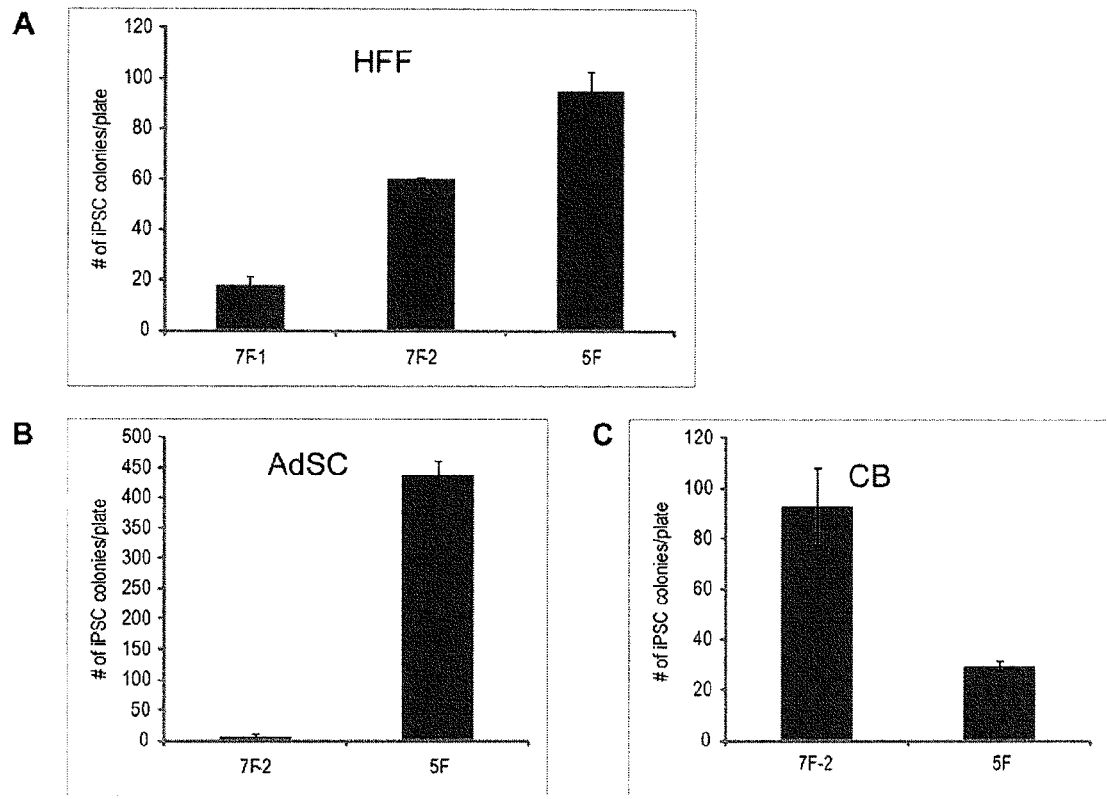
FIGS. 8A-8C. Effects of different episomal reprogramming vector combinations on iPSC derivation from different somatic cell types in the presence of small molecules.

The effect of small molecules on feeder-free episomal reprogramming is not cell type-specific, but rather applies to different somatic cell types (FIGS. 8A-8C). Additionally, this data illustrate the importance of identifying the right combination of episomal vectors (different reprogramming transgene combination and different transgene expression level) in order to achieve the optimal reprogramming efficiency for each cell type.

Figure 9:
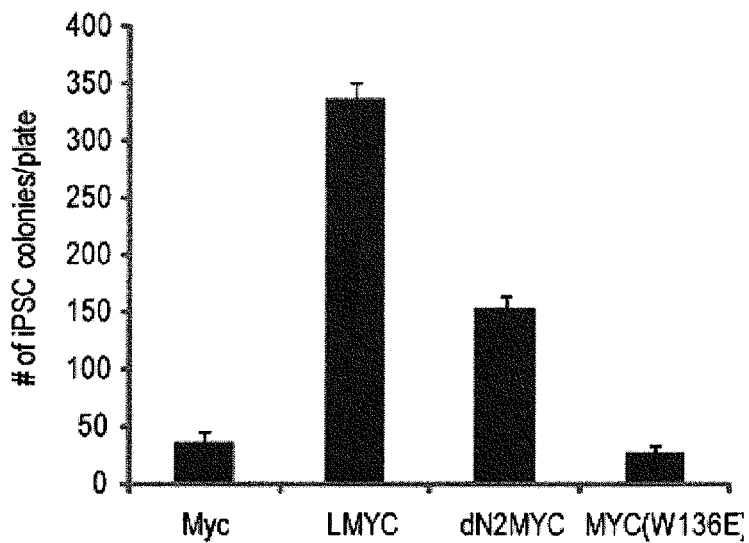
FIG. 9. Improved episomal reprogramming with transformation-deficient MYC in the presence of small molecules. Episomal vector combination 7F-2 was used for iPSC derivation. c-Myc in vector pCEP4-M2L was replaced with transformation deficient MYC: LMYC(NM_001033081), MYC with 41 amino acid deleted at the N-terminus (dN2MYC), or MYC with mutation at amino acid 136 (W136E) (Nakagawa et al., 2010). Transfected human foreskin fibroblasts (HFFs, p9) were plated to Matrigel™-coated 10-cm dishes in foreskin fibroblast culture medium. N2B27-100 medium supplemented with PD0325901 (P, 0.5 μM), CHIR99021(C, 3 μM), A-83-01(A, 0.5 μM), hLIF (L, 1000 U/ml) and HA-100 (H, 10 μM) (PCALH) was used to support reprogramming between day 2 and 13 post-transfection, followed by mTeSR1 between day 14 and 20 post-transfection. The number of iPSC colonies was from ~0.33×10$^6$ input cells. Data shown are mean±standard error (s.e.m.) (n=3).

Significant improved episomal reprogramming efficiency was achieved with transformation difficient MYC (FIG. 9), e.g., LMYC yielded ~1000 iPSC colonies per 1×10⁶ input human foreskin fibroblasts.

To summarize, using a combined genetic and chemical approach, we have successfully established a nonviral feeder-free episomal reprogramming method with much improved efficiency. Though developed with fibroblasts, this method is applicable to cell types of tissues that are easily obtainable from living human donors such as adipose tissue and peripheral blood. As different cell types appear to have preference for specific combinations and expression levels of reprogramming factors, it might be necessary to test different episomal reprogramming vectors for optimal efficiency. Additional features can be introduced into episomal vectors to further improve reprogramming efficiency. For example, the current episomal vectors have elements necessary for bacterial propagation, which contain many CpG islands known to contribute to transgene silencing (Chen et al., 2004). It is possible to minimize transgene silencing by removing the bacterial vector component using site-specific recombination to produce minicircle oriP/EBNA-1 episomal vectors. Nevertheless, the new method is simple and efficient enough for the routine derivation of footprint-free iPSCs from a large number of human donor samples, and with a defined matrix that supports donor cell attachment and iPSC growth, this method can be easily adapted to the production of clinical-grade human iPSCs.

Cell Culture.

Human ESCs and iPSCs were maintained on irradiated MEFs in DMEM/F12 culture medium supplemented with 20% KnockOut™ serum replacement, 0.1 mM non-essential amino acids, 1 mM GlutaMAX (all from Invitrogen, Carlsbad, Calif.), 0.1 mM β-mercaptoethanol (Sigma, St. Louis, Mo.) and 100 ng/ml zebrafish basic fibroblast growth factor (zbFGF) (Yu et al., 2009). MEF-conditioned human ESC medium was prepared as previously described (Xu et al., 2001). Human newborn foreskin fibroblasts (Cat# CRL-2097™, ATCC, Manassas, Mass.) and adult skin fibroblasts (Cat# CRL-2106™, ATCC) were cultured in DMEM (Invitrogen) supplemented with 10% heat-inactivated fetal bovine serum (FBS, HyClone Laboratories, Loan, Utah), 0.1 mM non-essential amino acids, 1 mM GlutaMAX, 0.1 mM β-mercaptoethanol and 4 ng/ml zbFGF.

The feeder-free culture of human ESCs and iPSCs on Matrigel™ (BD Biosciences, Bedford, Mass.) in mTeSR™1 (STEMCELL Technologies, Vancouver, BC, Canada) was carried out as previously described with modifications in the passaging procedure (Ludwig et al., 2006c). Briefly EDTA splitting method was employed. When human ESCs and iPSCs reach confluence, cells were washed once with PBS free of $Ca^{2+}$ and $Mg^{2+}$, and incubated with 0.5 mM EDTA for 8 minutes at 37° C. (2 ml/well of 6-well plate). After incubation, the EDTA solution was removed and fresh mTeSR1 (2 ml/well of 6-well plate) was added dropwise to each well for cell detachment. Most cells came off the plate with gentle shaking. Dissociated cells were then immediately aliquoted into freshly prepared Matrigel™ plates prefilled with mTeSR1. To improve cell attachment and survival, the ROCK inhibitor HA-100 (10 µM, Santa Cruz Biotechnology, Santa Cruz, Calif.) was added to mTeSR1 for 1 day during passaging. With this method, human ESCs and iPSCs were passaged every 3 to 4 days at a splitting ratio of 1:8 for optimal growth.

Reprogramming Human Fibroblasts.

Episomal reprogramming vectors containing expression cassettes for human OCT4, SOX2, NANOG, LIN28, c-MYC, KLF4 and SV40LT transgenes were as previously described (Yu et al., 2009). Specifically, vector pEP4EO2SCK2MEN2L and pEP4EO2SET2K (combination 4) were used for reprogramming optimization. About 7.3 µg of vector pEP4EO2SCK2MEN2L and 3.2 µg of pEP4EO2SET2K were co-transfected into human neonatal foreskin fibroblasts via nucleofection (NHDF-VPD-1001 with U-20 program, Amaxa, Walkersville, Md.). Transfected fibroblasts (~1.0×10⁶ cells per nucleofection) were plated directly to 3×10-cm MEF-seeded dishes or 3×10-cm Matrigel™-coated dishes in fibroblast culture medium. The next day after transfection, fibroblast medium was replaced with MEF-conditioned human ESC medium supplemented with 100 ng/ml zbFGF (CM100), or chemically defined N2B27 medium (N2B27), or N2B27 medium supplemented with 100 ng/ml zbFGF (N2B27-100), or mTeSR1. The N2B27 medium consists of DMEM/F12 culture medium supplemented with N-2 supplement (1×, Invitrogen), B-27 supplement (1×, Invitrogen), 0.1 mM non-essential amino acids, 1 mM GlutaMAX, and 0.1 mM β-mercaptoethanol. Where applied, small molecules PD0325901 (P, 0.5 µM), CHIR99021(C, 3 µM), A-83-01(A, 0.5 µM) (all from Stemgent, San Diego, Calif.), hLIF (L, 1000 U/ml, Millipore, Billerica, Mass.) and HA-100 (H, 10 µM) were added to reprogramming culture. Culture medium was refreshed every two days. Alkaline phosphatase staining (Cat# SCR004, Millipore) was performed in subsets of reprogramming experiments to facilitate the identification of iPSCs. Feeder-free episomal reprogramming of human adult skin fibroblasts using defined culture media was carried out similarly to that of foreskin fibroblasts with minimal changes in the protocol—transfected adult fibroblasts were plated to one instead of three 10-cm Matrigel™ dish due to lower cell survival following nucleofection. To characterize the iPSCs derived under the feeder-free condition, colonies with typical iPSC morphology were picked directly onto Matrigel™-coated 12-well plates in mTeSR1. EDTA splitting method was employed to facilitate iPSC expansion while minimizing the carry-over of differentiated cells during passaging. Complete loss of episomal reprogramming vectors was generally achieved around passage 14 for all iPSC clones derived from both human foreskin fibroblasts and adult skin fibroblasts.

RT-PCR Expression Analysis, PCR Analysis of Episomal Vectors, Bisulfite-Sequencing Analysis, Flow Cytometry Analysis and Karyotyping.

PCR, RT-PCR, flow cytometry analysis were performed as previously described (Yu et al., 2007; Yu et al., 2009). The methylation status of OCT4 and NANOG promoters were analyzed using bisulfite sequencing with MethylCode™ Bisulfite Conversion Kit (Invitrogen) (Yu et al., 2009). All primers were in Table 1 and antibodies were in Table 2. Standard G-banding chromosome analysis was carried out in the Cytogenetics Lab at WiCell Research Institute (Madison, Wis.).

TABLE 1

Primers for PCR, RT-PCR and bisulfite-sequencing PCR.

| Genes | Size (bp) | Symmbol | SEQ ID NO | Sequences (5' to 3') | |
|---|---|---|---|---|---|
| For quantitative RT-PCR | | | | | |
| OCT4 | 161 | OCT4-F1 | 1 | CAGTGCCCGA AACCCACAC | Total |
| | | OCT4-R1 | 2 | GGAGACCCAG CAGCCTCAAA | |

TABLE 1-continued

Primers for PCR, RT-PCR and bisulfite-sequencing PCR.

| Genes | Size (bp) | Symmbol | SEQ ID NO | Sequences (5' to 3') | |
|---|---|---|---|---|---|
| | 113 | OCT4-F2 | 3 | AGTTTGTGCCAGGGTTTTTG | Endogenous |
| | | OCT4-R2 | 4 | ACTTCACCTTCCCTCCAACC | |
| NANOG | 111 | NANOG-F1 | 5 | CAGAAGGCCTCAGCACCTAC | Total |
| | | NANOG-R1 | 6 | ATTGTTCCAGGTCTGGTTGC | |
| | 194 | NANOG-F2 | 7 | TTTGGAAGCTGCTGGGGAAG | Endogenous |
| | | NANOG-R2 | 8 | GATGGGAGGAGGGGAGAGGA | |
| SOX2 | 189 | SOX2-F2 | 9 | AGTCTCCAAGCGACGAAAAA | Endogenous |
| | | SOX2-R2 | 10 | TTTCACGTTTGCAACTGTCC | |
| LIN28 | 104 | LIN28-F2 | 11 | AGTGGCCTGGATAGGGAAGT | Endogenous |
| | | LIN28-R2 | 12 | CTTGGCTCCATGAATCTGGT | |
| GAPDH | 152 | GAPDH-F | 13 | GTGGACCTGACCTGCCGTCT | Endogenous |
| | | GAPDH-R | 14 | GGAGGAGTGGGTGTCGCTGT | |

For regular RT-PCR

| T-OCT4 | 657 | Oct4-SF1 | 15 | AGTGAGAGGCAACCTGGAGA | Exogenous |
| | | IRES2-SR | 16 | AGGAACTGCTTCCTTCACGA | |
| T-NANOG | 732 | Nanog-F1 | 17 | CAGAAGGCCTCAGCACCTAC | Exogenous |
| | | IRES2-SR | 18 | AGGAACTGCTTCCTTCACGA | |
| T1-KLF4 | 442 | Klf4-SF1 | 19 | CCCACACAGGTGAGAAACCT | Exogenous |
| | | IRES2-SR | 20 | AGGAACTGCTTCCTTCACGA | |
| T2-KLF4 | 253 | IRES2-SF | 21 | TGGCTCTCCTCAAGCGTATT | Exogenous |
| | | Klf4-SR | 22 | GTGGAGAAAGATGGGAGCAG | |
| T-SV40LT | 491 | SV40T-SF1 | 23 | TGGGGAGAAGAACATGGAAG | Exogenous |
| | | IRES2-SR | 24 | AGGAACTGCTTCCTTCACGA | |
| T-SOX2 | 498 | IRES2-SF | 25 | TGGCTCTCCTCAAGCGTATT | Exogenous |
| | | Sox2-SR | 26 | GCTTAGCCTCGTCGATGAAC | |
| T-LIN28 | 245 | IRES2-SF | 27 | TGGCTCTCCTCAAGCGTATT | Exogenous |
| | | Lin28-SR | 28 | GCAAACTGCTGGTTGGACAC | |
| T-c-MYC | 298 | IRES2-SF | 29 | TGGCTCTCCTCAAGCGTATT | Exogenous |
| | | Myc-SR | 30 | CACCGAGTCGTAGTCGAGGT | |
| OCT4 | 113 | OCT4-F2 | 31 | AGTTTGTGCCAGGGTTTTTG | Endogenous |
| | | OCT4-R2 | 32 | ACTTCACCTTCCCTCCAACC | |
| GAPDH | 152 | GAPDH-F | 33 | GTGGACCTGACCTGCCGTCT | Endogenous |
| | | GAPDH-R | 34 | GGAGGAGTGGGTGTCGCTGT | |

For PCR

| T-OCT4 | 657 | Oct4-SF1 | 35 | AGTGAGAGGCAACCTGGAGA | Exogenous |
| | | IRES2-SR | 36 | AGGAACTGCTTCCTTCACGA | |
| T-NANOG | 732 | Nanog-F1 | 37 | CAGAAGGCCTCAGCACCTAC | Exogenous |
| | | IRES2-SR | 38 | AGGAACTGCTTCCTTCACGA | |
| T1-KLF4 | 442 | Klf4-SF1 | 39 | CCCACACAGGTGAGAAACCT | Exogenous |
| | | IRES2-SR | 40 | AGGAACTGCTTCCTTCACGA | |
| T2-KLF4 | 401 | Klf4-SF1 | 41 | CCCACACAGGTGAGAAACCT | Exogenous |
| | | SV40pA-R | 42 | CCCCCTGAACCTGAAACATA | |
| T-SV40LT | 491 | SV40T-SF1 | 43 | TGGGGAGAAGAACATGGAAG | Exogenous |
| | | IRES2-SR | 44 | AGGAACTGCTTCCTTCACGA | |
| T-SOX2 | 534 | Sox2-SF1 | 45 | ACCAGCTCGCAGACCTACAT | Exogenous |
| | | SV40pA-R | 46 | CCCCCTGAACCTGAAACATA | |
| T-LIN28 | 447 | LIN28-SF1 | 47 | AAGCGCAGATCAAAAGGAGA | Exogenous |
| | | SV40pA-R | 48 | CCCCCTGAACCTGAAACATA | |
| T-c-MYC | 352 | Myc-SF1 | 49 | TCAAGAGGCGAACACACAAC | Exogenous |
| | | BGH-SR | 50 | CAACAGATGGCTGGCAACTA | |
| OCT4 | 113 | Oct4-F2 | 51 | AGTTTGTGCCAGGGTTTTTG | Endogenous |
| | | Oct4-R2 | 52 | ACTTCACCTTCCCTCCAACC | |

For bisulfte-sequencing PCR

| OCT4 | 221 | Oct4-mF3 | 53 | ATTTGTTTTTTGGGTAGTTAAAGGT | Endogenous |
| | | Oct4-mR3 | 54 | CCAACTATCTTCATCTTAATAACATCC | |
| NANOG | 164 | Nanog-mF3 | 55 | TTAATTTATTGGGATTATAGGGGTG | Endogenous |
| | | Nanog-mR3 | 56 | AAACCTAAAAACAAACCCAACAAC | |
| | 295 | Nanog-mF4 | 57 | GGTTGGTTTTAAATTTTTGATTTTAG | Endogenous |
| | | Nanog-mR4 | 58 | ACCAATCTCACCAAAACCATTATAA | |

TABLE 2

Antibodies for flow cytometry analysis.

| Antigen | Fluorochrome | Clone | Isotype | Company |
|---|---|---|---|---|
| SSEA-3 | PE | MC631 | Rat IgM | BD Biosciences |
| SSEA-4 | PE | MC813-70 | Mouse IgG3 | BD Biosciences |
| TRA-1-60 | FITC | TRA-1-60 | Mouse IgM | BD Biosciences |
| TRA-1-81 | FITC | TRA-1-81 | Mouse IgM | BD Biosciences |
| CD44 | APC | G44-26 | Mouse IgG2b | BD Biosciences |

Teratoma Formation.

To examine the in vivo developmental pluripotency of human iPSCs derived under the feeder-free condition, iPSCs grown on Matrigel™ in mTeSR1 were transferred to MEF feeder cells for one passage. Cells were collected with collagenase treatment, and injected into hind limb muscles of 6-week-old immunocompromised SCID-beige mice (approximately one 10-cm dish with 50 to 80% confluence per mouse) (Harlan, Madison, Wis.). After six to eight weeks, teratomas were dissected and fixed in 10% formalin (Fisher, Pittsburgh, Pa.). Samples were embedded in paraffin and processed with hematoxylin and eosin staining in the Experimental Pathology Department of McArdle Laboratory for Cancer Research, University of Wisconsin-Madison, Wis.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,683,202
U.S. Pat. No. 5,302,523
U.S. Pat. No. 5,322,783
U.S. Pat. No. 5,384,253
U.S. Pat. No. 5,464,765
U.S. Pat. No. 5,478,838
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,610,042
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,925,565
U.S. Pat. No. 5,928,906
U.S. Pat. No. 5,935,819
U.S. Pat. No. 5,945,100
U.S. Pat. No. 5,981,274
U.S. Pat. No. 5,994,624
U.S. Pat. No. 6,833,269
U.S. application Ser. No. 12/478,154
U.S. Patent Publn. 2002/0076976
U.S. Patent Publn. 2003/0059913
U.S. Patent Publn. 2003/0062225
U.S. Patent Publn. 2003/0062227
U.S. Patent Publn. 2003/0087919
U.S. Patent Publn. 2003/0125344
U.S. Patent Publn. 2003/0211603
U.S. Patent Publn. 2004/0002507
U.S. Patent Publn. 2004/0002508
U.S. Patent Publn. 2004/0014755
U.S. Patent Publn. 2004/0039796
U.S. Patent Publn. 2005/0192304
U.S. Patent Publn. 2005/0209261
U.S. Patent Publn. 2005/123902
U.S. Patent Publn. 2007/0116680
U.S. Patent Publn. 2007/0238170
U.S. Patent Publn. 2008/004287
U.S. Patent Publn. 2008/0171385
A practical approach, 1987.
Adams, *J. Virol.*, 61(5):1743-1746, 1987.
Aiyar et al., *EMBO J.*, 17(21):6394-6403, 1998.
Alexander et al., *Proc. Nat. Acad. Sci. USA*, 85:5092-5096, 1988.
Altmann et al., *Proc. Natl. Acad. Sci. USA*, 103(38):14188-14193, 2006.
Amit et al., *Dev Biol.*, 227(2):271-8, 2000.
Animal Cell Culture, 1987.
Aravind and Landsman, *Nucleic Acids Res.*, 26(19):4413-4421, 1998.
Ausubel et al., Current Protocols in Molecular Biology, Greene Publishing Associates and Wiley Interscience, N.Y., 1994.
Baer et al., *Biochemistry*, 39:7041-7049, 2000.
Baer et al., *Nature*, 310(5974):207-211, 1984.
Bain et al., *Biochem. J.*, 408(3):297-315, 2007.
Bennett et al, *J. Biol. Chem.*, 277:34, 2002.
Bertrand et al., *J. Mol Biol.*, 333(2):393-407, 2003.
Bingham, *Cell*, 90(3):385-387, 1997.
Bochkarev et al., *Cell*, 84(5):791-800, 1996.
Bode et al., *Biol. Chem.*, 381:801-813, 2000.
Bode et al., *Gene Ther. Mol. Biol.*, 6:33-46, 2001.
Bode et al., *Science*, 255(5041):195-197, 1992.
Buecker et al., *Cell Stem Cell*, 6:535-546, 2010.
Buehr et al., *Cell*, 135:1287, 2008.
Carbonelli et al., *FEMS Microbiol. Lett.*, 177(1):75-82, 1999.
Chandler et al., *Proc. Natl. Acad. Sci. USA*, 94(8):3596-601, 1997.
Chang, et al., *Frontiers in Bioscience*, 12:4393-4401, 2007.
Chaudhuri et al., *Proc. Natl. Acad. Sci. USA*, 98(18):10085-10089, 2001.
Chen and Okayama, *Mol. Cell Biol.*, 7(8):2745-2752, 1987.
Chen et al., *Cell Stem Cell*, 7:240-248, 2010.
Chen et al., *Gene Ther.*, 11:856-864, 2004.
Chin et al., *Molecular Brain Res.*, 137(1-2):193-201, 2005.
Chow et al., *Cytometry Commun. Clinical Cytometry*, 46:72-78, 2001.
Cocea, *Biotechniques*, 23(5):814-816, 1997.
Current Protocols in Molecular Biology and Short Protocols in Molecular Biology, 1987; 1995.
DaCosta et al., *Molec. Pharmacol.*, 65(3):744-752, 2004.
Davies et al., *Biochem J.*, 351:95-105, 2000.
de Gouville et al., *Drug News Perspective*, 19(2):85-90, 2006.
Dhar et al., *Cell*, 106(3):287-296, 2001.
Downey et al., *J. Biol. Chem.*, 271(35):21005-21011, 1996.
Embryonic Stem Cell Differentiation in vitro, 1993.
English et al., *Trends in Pharmac. Sci.*, 23(1):40-45, 2002.
Ercolani et al., *J. Biol. Chem.*, 263:15335-15341, 1988.
Ermakova et al., *J. Biol. Chem.*, 271(51):33009-33017, 1996.
Esteban et al., *J. Biol. Chem.*, 284:17634-17640, 2009.
European Appln. EPO 0273085
Evans and Kaufman, *Nature*, 292:154-156, 1981.
Evans, et al., *In: Cancer Principles and Practice of Oncology*, Devita et al. (Eds.), Lippincot-Raven, NY, 1054-1087, 1997.

Fechheimer et al., *Proc Natl. Acad. Sci. USA,* 84:8463-8467, 1987.
Fernandes et al., *Nature Cell Biology,* 6:1082-1093, 2004.
Fischer et al., *J. Virol.,* 71:5148-5146, 1997.
Fraley et al., *Proc. Natl. Acad. Sci. USA,* 76:3348-3352, 1979.
Frame et al, *Biochemical J.,* 359:1-16, 2001.
Frappier and O'Donnell, *Proc. Natl. Acad. Sci. USA,* 88(23): 10875-10879, 1991.
Fusaki et al., *Proc. Jpn. Acad. Ser. B Phys. Biol. Sci.,* 85:348-362, 2009.
Gahn and Schildkraut, *Cell,* 58(3):527-535, 1989.
Gahn and Sugden, *J. Virol.,* 69(4):2633-2636, 1995.
Garrick et al., *Nat. Genet.,* 18:56-59, 1998.
Gellibert, et al., *J. Med. Chem.,* 49(7):2210-2221, 2006.
Gene Targeting, A Practical Approach, 1993.
Gene Transfer Vectors for Mammalian Cells, 1987.
Ghosh and Bachhawat, In: *Liver Diseases, Targeted Diagnosis and Therapy Using Specific Receptors and Ligands,* Wu et al. (Eds.), Marcel Dekker, NY, 87-104, 1991.
Gopal, *Mol. Cell Biol.,* 5:1188-1190, 1985.
Gould et al, *Intl. J. Neuropsychopharmacology,* 7:387-390, 2004.
Gould et al, *Pharmacological Res.,* 48:49-53, 2003.
Graham and Van Der Eb, *Virology,* 52:456-467, 1973.
Guide to Techniques in Mouse Development (1993)
Hanna et al., *Proc. Natl. Acad. Sci. USA,* 107:9222-9227, 2010.
Harb et al., *PLoS One,* 3(8):e3001, 2008.
Harland and Weintraub, *J. Cell Biol.,* 101(3):1094-1099, 1985.
Hegde et al., *Nature,* 359(6395):505-512, 1992.
Hogan et al., In: *Manipulating the Mouse Embryo*: A Laboratory Manual, 2nd Ed., Cold Spring Harbor Laboratory Press, 1994.
Hung et al., *Proc. Natl. Acad. Sci. USA,* 98(4):1865-1870, 2001.
Inman et al., *Molec. Pharmacol.,* 62(1):65-74, 2002.
Jainchill et al., *J. Virol.,* 4(5):549-53, 1969.
Jenke et al., *Proc. Natl. Acad. Sci. USA,* 101 (31), 11322-11327, 2004.
Jia et al., *Nat. Methods,* 7:197-199, 2010.
Julien et al., *Virology,* 326(2):317-328, 2004.
Kaeppler et al., *Plant Cell Reports,* 9:415-418, 1990.
Kaji et al., *Nature,* 458:771-775, 2009.
Kameda et al., *Biochem. Biophys. Res. Commun.,* 349:1269-1277, 2006.
Kaminska et al., *Acta Biochimica Polonica,* 52(2):329-337, 2005.
Kanda et al., *Mol. Cell. Biol.,* 21(10):3576-3588, 2001.
Kaneda et al., *Science,* 243:375-378, 1989.
Karin et al. *Cell,* 36:371-379, 1989.
Kato et al, *J. Biol. Chem.,* 266:3361-3364, 1991.
Keller et al., *Curr. Opin. Cell Biol.,* 7(6):862-9, 1995.
Kennedy and Sugden, *Mol. Cell. Biol.,* 23(19):6901-6908, 2003.
Kennedy et al., *Proc. Natl. Acad. Sci. USA,* 100:14269-14274, 2003.
Kim et al., *Cell Stem Cell,* 4:472, 2009.
Kim et al., *J. Biol. Chem.,* 275(40):31245-31254, 2000.
Kim et al., *Virology,* 239(2):340-351, 1997.
Kim et al., *Xenobiotica,* 38(3):325-339, 2008.
Kirchmaier and Sugden, *J. Virol.,* 69(2):1280-1283, 1995.
Kirchmaier and Sugden, *J. Virol.,* 72(6):4657-4666, 1998.
Klein et al., *Neoplasia,* 8:1-8, 2006.
Klein et al., *Nature,* 327:70-73, 1987.
Klimanskaya et al., *Lancet.,* 365(9471):1636-41, 2005.
Kodama et al. *J. Cell Physiol.,* 112(1):89-95, 1982.
Langle-Rouault et al., *J. Virol.,* 72(7):6181-6185, 1998.
Leight and Sugden, *Mol. Cell Bio.,* 21:4149-61, 2001.
Levenson et al., *Hum. Gene Ther.,* 9(8):1233-1236, 1998.
Levitskaya et al., *Nature,* 375(6533):685-688, 1995.
Levitskaya et al., *Proc. Natl. Acad. Sci. USA,* 94(23):12616-12621, 1997.
Li et al., *Cell Stem Cell,* 4:16, 2009.
Li et al., *Cell Stem Cell,* 4:16-19, 2009.
Li et al., *Cell,* 135:1299, 2008.
Lin et al., *Nat. Methods,* 6:805-808, 2009.
Lindner and Sugden, *Plasmid,* 58:1-12, 2007.
Lindner et. al. *J. Virol.,* 82(12):5693-702, 2008.
Liu et al., *Biochem. Biophys. Res. Commun.,* 346:131-139, 2006.
Liu et al., *Cell Stem Cell* 3, 587-590, 2008.
Loh et al., *Blood,* 113:5476-5479, 2009.
Lowry et al., *Proc. Natl. Acad. Sci. USA,* 105:2883, 2008.
Ludwig et al., *Nat. Biotechnol.,* 24(2):185-187, 2006b.
Ludwig et al., *Nat. Methods,* 3(8):637-46, 2006a.
Ludwig et al., *Nat. Methods,* 3:637-646, 2006c.
Macejak and Sarnow, *Nature,* 353:90-94, 1991.
Mackey and Sugden, *Mol. Cell. Biol.,* 19(5):3349-3359, 1999.
Mackey et al., *J. Virol.,* 69(10):6199-6208, 1995.
Maniatis, et al., Molecular Cloning, A Laboratory Manual, Cold Spring Harbor Press, Cold Spring Harbor, N.Y., 1988.
Manzini et al., *Proc. Natl. Acad. Sci. USA,* 103(47):17672-17677, 2006.
Marechal et al., *J. Virol.,* 73(5):4385-4392, 1999.
Martin, et al., *Nature Immunology,* 6:111-184, 2005.
Martin, *Proc. Natl. Acad. Sci. USA,* 78(12):7634-8, 1981.
Mattingly et al, *J. Pharmacol. Experimen. Therap.,* 316:456-465, 2006.
Middleton and Sugden, *J. Virol.,* 66(1):489-495, 1992.
Middleton and Sugden, *J. Virol.,* 68:4067-4071, 1994.
Nabel et al., *Science,* 244(4910):1342-1344, 1989.
Nakagawa et al. *Proc. Natl. Acad. Sci. USA,* 107(32):14152-7, 2010. Nakano et al., *Science,* 272(5262):722-4, 1996.
Nanbo et al., *EMBO J.,* 26:4252-62, 2007.
Ng, *Nuc. Acid Res.,* 17:601-615, 1989.
Nicolau and Sene, *Biochim. Biophys. Acta,* 721:185-190, 1982.
Nicolau et al., *Methods Enzymol.,* 149:157-176, 1987.
Niller et al., *J. Biol. Chem.,* 270(20:12864-12868, 1995.
Noble et al, *Proc. Natl. Acad. Science, USA,* 102:6990-6995, 2005.
Okita et al., *Nature,* 448:313, 2007.
Okita et al., *Nature,* 448:313-317, 2007.
Okita et al., *Science,* 322:949, 2008.
Okita et al., *Science,* 322:949-953, 2008.
Park et al., *Nature,* 451:141, 2008.
PCT Appln. WO 2007/113505
PCT Appln. WO 2008/006583
PCT Appln. WO 2008/094597
PCT Appln. WO 94/09699
PCT Appln. WO 95/06128
PCT Publn. PCT 2005/080554
PCT Publn. WO 01/088100
PCT Publn. WO 98/30679
Pelletier and Sonenberg, *Nature,* 334(6180):320-325, 1988.
Perales et al., *Proc. Natl. Acad. Sci. USA,* 91:4086-4090, 1994.
Piechaczek et al., *Nucleic Acids Res.,* 27(2):426-428, 1999.
Potrykus et al., *Mol. Gen. Genet.,* 199(2):169-177, 1985.
Potter et al., *Proc. Natl. Acad. Sci. USA,* 81:7161-7165, 1984.
Properties and uses of Embryonic Stem Cells: Prospects for Application to Human Biology and Gene Therapy (1998)

Quitsche et al., *J. Biol. Chem.*, 264:9539-9545, 1989.
Rawlins et al., *Cell*, 42((3):859-868, 1985.
Reisman and Sugden, *Mol. Cell. Biol.*, 6(11):3838-3846, 1986.
Reisman et al., *Mol. Cell. Biol.*, 5(8):1822-1832, 1985.
Richards et al., *Cell*, 37:263-272, 1984.
Rinehart et al., *J. Clinical Oncol.*, 22:4456-4462, 2004.
Ring et al., *Diabetes*, 52:588-595, 2003.
Rippe, et al., *Mol. Cell Biol.*, 10:689-695, 1990.
Ritzi et al., *J. Cell Sci.*, 116(Pt 19):3971-3984, 2003.
Sambrook et al., In: *Molecular cloning: a laboratory manual*, 2nd Ed., Cold Spring Harbor Laboratory Press, Cold Spring Harbor, N.Y., 1989.
Schaarschmidt et al., *EMBO J.*, 23(1):191-201, 2004.
Schaffer et al.; *Gene*, 302(1-2):73-81, 2003.
Schepers et al., *EMBO J.*, 20(16):4588-4602, 2001.
Sears et al., *J. Virol.*, 77(21):11767-11780, 2003.
Sears et al., *J. Virol.*, 78(21):11487-11505, 2004.
Shi et al., *Cell Stem Cell*, 3:568, 2008.
Shimada et al., *Mol. Reprod. Dev*, 77:2, 2010.
Shire et al., *J. Virol.*, 73(4):2587-2595, 1999.
Silva et al., *PLoS Biol.*, 6:e253, 2008.
Stadtfeld et al., *Cell Stem Cell*, 2:230-240, 2008.
Stadtfeld et al., *Science*, 322:945, 2008.
Stadtfeld et al., *Science*, 322:945-949, 2008.
Su et al., *Proc. Natl. Acad. Sci. USA*, 88(23):10870-19874, 1991.
Sugden and Warren, *J. Virol.*, 63(6):2644-2649, 1989.
Sun et al., *Proc. Natl. Acad. Sci. USA*, 106:15720-15725, 2009.
Suzuki et al., *Cancer Res.*, 67(5):2351-2359, 2007.
Takahashi et al., *Cell*, 126(4):663-676, 2006.
Takahashi et al., *Cell*, 131:861, 2007.
Thomson et al., *Science*, 282:1145, 1998.
Tojo, et al., *Cancer Science*, 96(11):791-800, 2005,
Tur-Kaspa et al., *Mol. Cell Biol.*, 6:716-718, 1986.
Wagman, *Current Pharmaceutical Design*, 10:1105-1137, 2004.
Wagner et al., *Proc. Natl. Acad. Sci. USA* 87(9):3410-3414, 1990.
Wang et al., *Mol. Cell. Biol.*, 26(3):1124-1134, 2006.
Watanabe et al., *Nat. Biotechnol.*, 25:681-686, 2007.
Watanabe et al., *Nat. Neurosci.*, 8(3):288-96, 2005.
Wernig et al., *Nature*, 448(7151):318-24, 2007.
Wilson et al., *Science*, 244:1344-1346, 1989.
Woltjen et al., *Nature*, 458:766, 2009.
Woltjen et al., *Nature*, 458:766-770, 2009.
Wong et al., *Gene*, 10:87-94, 1980.
Wrzesinski et al., *Clinical Cancer Res.*, 13(18):5262-5270, 2007.
Wu and Wu, *Adv. Drug Delivery Rev.*, 12:159-167, 1993.
Wu and Wu, *Biochemistry*, 27: 887-892, 1988.
Wu and Wu, *J. Biol. Chem.*, 262:4429-4432, 1987.
Wu et al., *J. Virol.*, 76(5):2480-2490, 2002.
Wysokenski and Yates, *J. Virol.*, 63(6):2657-2666, 1989.
Xu et al., *Nat. Biotechnol.*, 19:971, 2001.
Xu et al., *Nat. Biotechnol.*, 19:971-974, 2001.
Yamanaka et al., *Cell*, 131(5):861-72, 2007.
Yang and Russell, *Proc. Natl. Acad. Sci. USA*, 87:4144-4148, 1990.
Yates and Guan, *J. Virol.*, 65(1):483-488, 1991.
Yates and Guan, *J. Virol.*, 65:483-488, 1991.
Yates et al., *J. Virol.*, 74(10):4512-4522, 2000.
Yates et al., *Nature*, 313:812-815, 1985.
Yates et al., *Proc. Natl. Acad. Sci. USA*, 81:3806-3810, 1984.
Yates, *Cancer Cells*, (6)197-205, 1988.
Yin et al., *Science*, 301(5638):1371-1374, 2003.
Ying, *Nature*, 453:519-23, 2008.
Yu et al., *Science*, 318:1917, 2007.
Yu et al., *Science*, 324:797, 2009.
Yu et al., *Science*, 324:797-801, 2009.
Zhang et al., *Bioorganic Med. Chem. Letters;* 10:2825-2828, 2000.
Zhou and Freed, *Stem Cells*, 2009 (Ahead of Epub Print).
Zhou et al., *Cell Stem Cell*, 4:381-384, 2009.
Zhou et al., *EMBO J.*, 24(7):1406-1417, 2005.

What is claimed is:

1. A method for producing a population of human iPS cells, comprising:
   a) obtaining human somatic cells comprising an extra-chromosomal genetic element that expresses one or more reprogramming factors selected from Oct4, Sox2, Nanog, Lin28, c-Myc, KLF4 and SV40LT transgenes;
   b) culturing the somatic cells and progeny cells thereof in a reprogramming condition comprising externally added fibroblast growth factor (FGF), GSK-3 inhibitor and at least one further chemical selected from an MEK inhibitor and a TGF-β receptor inhibitor, thereby producing a population of iPS cells;
   c) culturing the iPS cells in chemically defined expansion condition having chemically defined expansion medium essentially free of externally added GSK-3 inhibitor, MEK inhibitor, and TGF-β receptor inhibitor; and
   d) further culturing the iPS cells sufficiently to remove the genetic elements and provide iPS cells that are essentially free of exogenous genetic components.

2. The method of claim 1, wherein the expansion medium comprises TeSR or mTeSR.

3. The method of claim 1, further comprising selecting the iPS cells.

4. The method of claim 3, wherein the iPS cells are selected based on one or more embryonic cell characteristics.

5. The method of claim 1, wherein the reprogramming condition further comprises externally added LIF.

6. The method of claim 1, wherein the reprogramming condition further comprises externally added Rho-associated kinase (ROCK) inhibitor or myosin II inhibitor.

7. The method of claim 6, wherein the ROCK signaling inhibitor is HA-100.

8. The method of claim 1, wherein the reprogramming condition is chemically defined and employs a chemically defined reprogramming medium.

9. The method of claim 8, wherein the chemically defined reprogramming medium comprises TeSR medium, human embryonic cell culture medium, or N2B27 medium.

10. The method of claim 8, wherein the chemically defined reprogramming medium comprises externally added FGF.

11. The method of claim 8, wherein the chemically defined reprogramming medium is essentially free of externally added TGFβ.

12. The method of claim 1, wherein the reprogramming condition is essentially free of feeder cells.

13. The method of claim 1, wherein the reprogramming condition comprises a matrix component.

14. The method of claim 13, wherein the matrix component is selected from the group consisting of collagen, gelatin, poly-L-lysine, poly-D-lysine, vitronectin, laminin, fibronectin and mixtures thereof.

15. The method of claim 1, wherein the somatic cell is a fibroblast, a keratinocyte, a hematopoietic cell, a mesenchymal cell, an adipose cell, an endothelial cell, a neural cell, a muscle cell, a mammary cell, a liver cell, a kidney cell, a skin cell, a digestive tract cell, a cumulus cell, a gland cell, or a pancreatic islet cell.

16. The method of claim 1, wherein the extra-chromosomal genetic element comprises DNA.

17. The method of claim 1, wherein the extra-chromosomal genetic element comprises RNA.

18. The method of claim 1, wherein the extra-chromosomal genetic element is further defined as an episomal vector.

19. The method of claim 18, wherein the episomal vector is essentially free of bacterial elements.

20. The method of claim 18, wherein the episomal vector comprises a replication origin and one or more expression cassettes for expression of reprogramming factors, wherein one or more of said expression cassettes further comprise a nucleotide sequence encoding a trans-acting factor that binds to the replication origin to replicate an extra-chromosomal template, and/or wherein the somatic cell expresses such a trans-acting factor.

21. The method of claim 20, wherein the replication origin is a replication origin of a lymphotrophic herpes virus and corresponds to oriP of Epstein Barr virus (EBV).

22. The method of claim 21, wherein the replication origin is a replication origin of EBV, Kaposi's sarcoma herpes virus (KSHV), Herpes virus saimiri (HS), or Marek's disease virus (MDV).

23. The method of claim 20, wherein the trans-acting factor is an EBV nuclear antigen 1 (EBNA-1).

24. The method of claim 1, wherein the reprogramming factors comprise a myc mutant or homolog that is deficient in transformation.

25. The method of claim 24, wherein the reprogramming factors comprise LMYC (NM_001033081), MYC with 41 amino acid deleted at the N-terminus (dN2MYC), or MYC with mutation at amino acid 136 (W136E).

26. The method of claim 1, wherein the cells are cultured in the reprogramming condition for at least five days.

27. The method of claim 26, wherein the cells are cultured in the reprogramming condition during a period of from one day to five days after introduction of the extra-chromosomal genetic element into the somatic cells.

28. The method of claim 27, wherein the cells are cultured in the reprogramming condition during a period including from one day to fifteen days after introduction of the extra-chromosomal genetic element into the somatic cells.

* * * * *